US011617765B2

(12) United States Patent
Tamada et al.

(10) Patent No.: US 11,617,765 B2
(45) Date of Patent: Apr. 4, 2023

(54) ENHANCER FOR T-CELLS OR B-CELLS HAVING MEMORY FUNCTION, MALIGNANT TUMOR RECURRENCE INHIBITOR, AND INDUCER FOR INDUCING MEMORY FUNCTION IN T-CELLS OR B-CELLS

(71) Applicants: YAMAGUCHI UNIVERSITY, Yamaguchi (JP); NATIONAL UNIVERSITY CORPORATION TOTTORI UNIVERSITY, Tottori (JP)

(72) Inventors: Koji Tamada, Yamaguchi (JP); Yukimi Sakoda, Yamaguchi (JP); Keishi Adachi, Yamaguchi (JP); Takafumi Nakamura, Tottori (JP)

(73) Assignees: Yamaguchi University, Yamaguchi (JP); National University Corporation Totori University, Tottori (JP)

( * ) Notice: Subject to any disclaimer, the term of this patent is extended or adjusted under 35 U.S.C. 154(b) by 195 days.

(21) Appl. No.: 16/754,645

(22) PCT Filed: Oct. 9, 2018

(86) PCT No.: PCT/JP2018/037608
§ 371 (c)(1),
(2) Date: Apr. 8, 2020

(87) PCT Pub. No.: WO2019/073973
PCT Pub. Date: Apr. 18, 2019

(65) Prior Publication Data
US 2020/0352997 A1 Nov. 12, 2020

(30) Foreign Application Priority Data
Oct. 10, 2017 (JP) .............................. JP2017-196718

(51) Int. Cl.
*A61K 35/17* (2015.01)
*A61P 35/00* (2006.01)

(52) U.S. Cl.
CPC .............. *A61K 35/17* (2013.01); *A61P 35/00* (2018.01)

(58) Field of Classification Search
None
See application file for complete search history.

(56) References Cited

U.S. PATENT DOCUMENTS

| 2017/0291953 A1 | 10/2017 | Tamada et al. |
| 2019/0099446 A1 | 4/2019 | Tamada et al. |

FOREIGN PATENT DOCUMENTS

| WO | WO-2013/123061 A1 | 8/2013 |
| WO | WO-2016/056228 A1 | 4/2016 |
| WO | WO-2017/159736 A1 | 9/2017 |

OTHER PUBLICATIONS

Topfer, "Tumor Evasion from T Cell Surveillance," J Biomed Biotechnol. #918471, pp. 1-19 (Year: 2011).*
Bartlett et al., "Oncolytic viruses as therapeutic cancer vaccines," Molecular Cancer, 12:103 pp. 1-16 (Year: 2013).*
Chiocca et al., "Oncolytic Viruses and Their Application to Cancer Immunotherapy," Cancer Immunol Res, 2(4) pp. 295-300 (Year: 2014).*
Lichty et al., "Going viral with cancer immunotherapy," Nat. Rev. Cancer, vol. 14, pp. 560-567 (Year: 2014).*
Machine Translation to English of WO2016/056228 (Year: 2016).*
Sakoda et al., "Symposium 4, New Paradigm of Cell and Molecular Machineries for Advanced Immune Therapy," Japanese Journal of Clinical Hematology, 55(6), pp. 651656, 2014, with partial English translation.
Adachi, et al., "IL-7 and CCL19 expression in CAR-T cells improves immune cell infiltration and CAR-T cell survival in the tumor", Nat Biotechnol, Mar. 5, 2018, vol. 36, No. 4, pp. 346-351.
Nakazawa, "Gene-modified T-cell Therapy Using Chimeric Antigen Receptor", The Shinshu Medical Journal, 61 (4): 197-203 (2013) (partial translation attached).
Sato-Hashimoto M. et al., "Signal Regulatory Protein αλπηα Regulates the Homeostasis of T Lymphocytes in the Spleen", J. Immunol., 2011, vol. 187, No. 1, 291-7.
Siegert, et al., "Positive and negative regulation of T cell responses by fibroblastic reticular cells within paracortical regions of lymphnodes", Front. Immunol., 2012, vol. 3, article 285.
International Search Report dated Jan. 8, 2019 by the International Searching Authority for International Application No. PCT/JP2018/037608, filed on Oct. 9, 2018 and published as WO 2019/073973 on Apr. 18, 2019 (Applicant-Yamaguchi University) (Translation—5 Pages).
Extended European Search Report for Application No. 18866437.9 dated May 28, 2021.
Zhang, et al. "Interleukin-7 Inhibits Tumor-Induced CD27-CD28-Supressor T Cells: Implications for Cancer Immunotherapy", Clinical Cancer Research, vol. 17, No. 15, Aug. 1, 2011, pp. 4975-4986.

(Continued)

*Primary Examiner* — Daniel C Garnett
(74) *Attorney, Agent, or Firm* — Morgan, Lewis & Bockius LLP

(57) ABSTRACT

An object of the present invention is to provide an enhancer for endogenous T-cells or B-cells having a memory function and a malignant tumor recurrence inhibitor in order to continue to reject malignant tumor over a long period of time. An enhancer for T-cells or B-cells having a memory function in an administration subject, comprising a nucleic acid delivery vehicle, a nucleic acid encoding interleukin-7 (IL-7), and a nucleic acid encoding chemokine (C-C motif) ligand 19 (CCL19), and an inducer for inducing a memory function in T-cells or B-cells in an administration subject, are prepared. Also, a malignant tumor recurrence inhibitor comprising a nucleic acid delivery vehicle, a nucleic acid encoding interleukin-7 (IL-7), and a nucleic acid encoding CCL19, is prepared.

18 Claims, 27 Drawing Sheets

Specification includes a Sequence Listing.

(56) References Cited

OTHER PUBLICATIONS

Cardell, Markus et al., "Combined CCL19/ IL-7 treatment eradicates tumors in murine models of lung cancer", Proceedings of the American Association for Cancer Research Annual Meeting, (20060000), vol. 47, ISSN 0197-016X, p. 1306, XP009519912 [A] 1-20 *, abstract No. 5557.
Lai et al., "General Synthesis and Gas-Sensing Properties of Multiple-Shell Metal Oxide Hollow Microspheres," Angewandte Chemie, 123: 2790-2793 (2011).
Masotti et al., "Comparison of different commercially available cationic liposome-DNA lipoplexes: Parameters influencing toxicity and transfection efficiency," Colloids and Surfaces B: Biointerfaces, 68: 136-144 (2009).
Horev et al., "Generalized verrucosis and HPV-3 susceptibility associated with CD4 T-cell lymphopenia caused by inherited human interleukin-7 deficiency," Journal of the American Academy of Dermatology, 72 (6): 1083-1084 (2015).
Felipe, "Polycistronic Viral Vectors," Current Gene Therapy, 2: 355-378 (2002).
Pakula et al., "Genetic Analysis of Protein Stability and Function," Annual Review of Genetics, 23: 289-310 (1989).
Muller et al., "Spliceosomal Peptide P140 for Immunotherapy of Systemic Lupus Erythematosus," Arthritis & Rheumatism, 58 (12): 3873-3883 (2008).

* cited by examiner

CD44, CD62L: Memory cell marker
CD90.1-positive cell (CD90.1+): Administered donor T-cell
CD90.2-positive cell (CD90.2+): endogenous T-cell of recipient

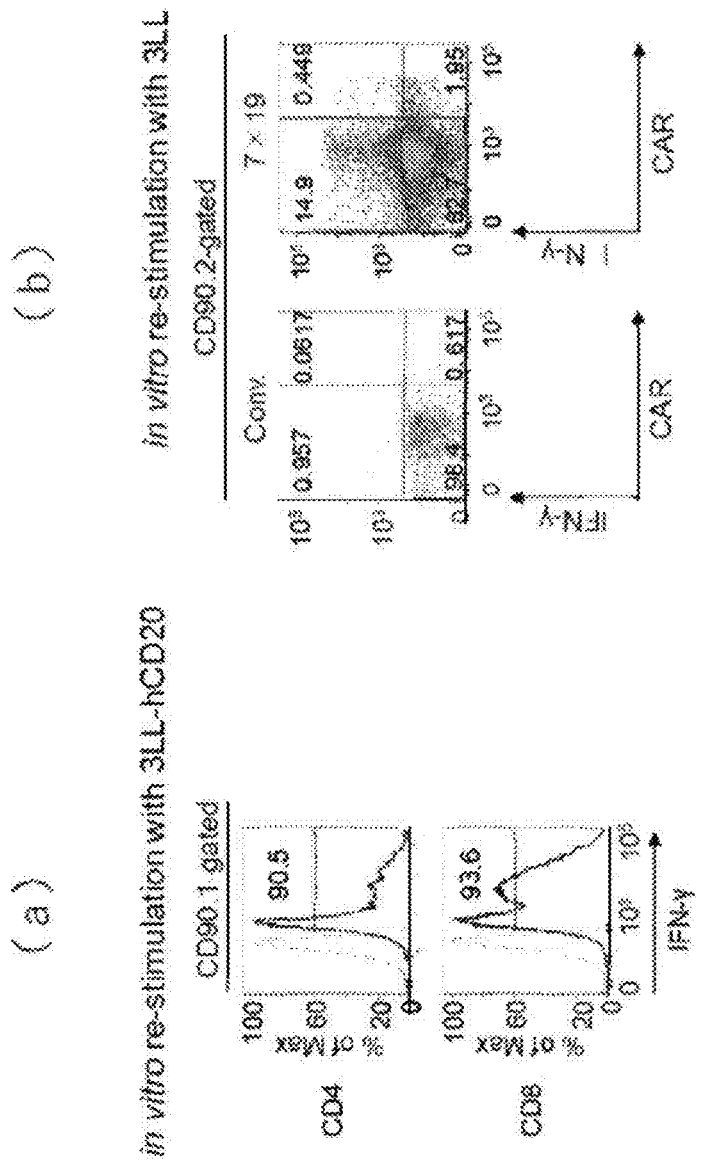

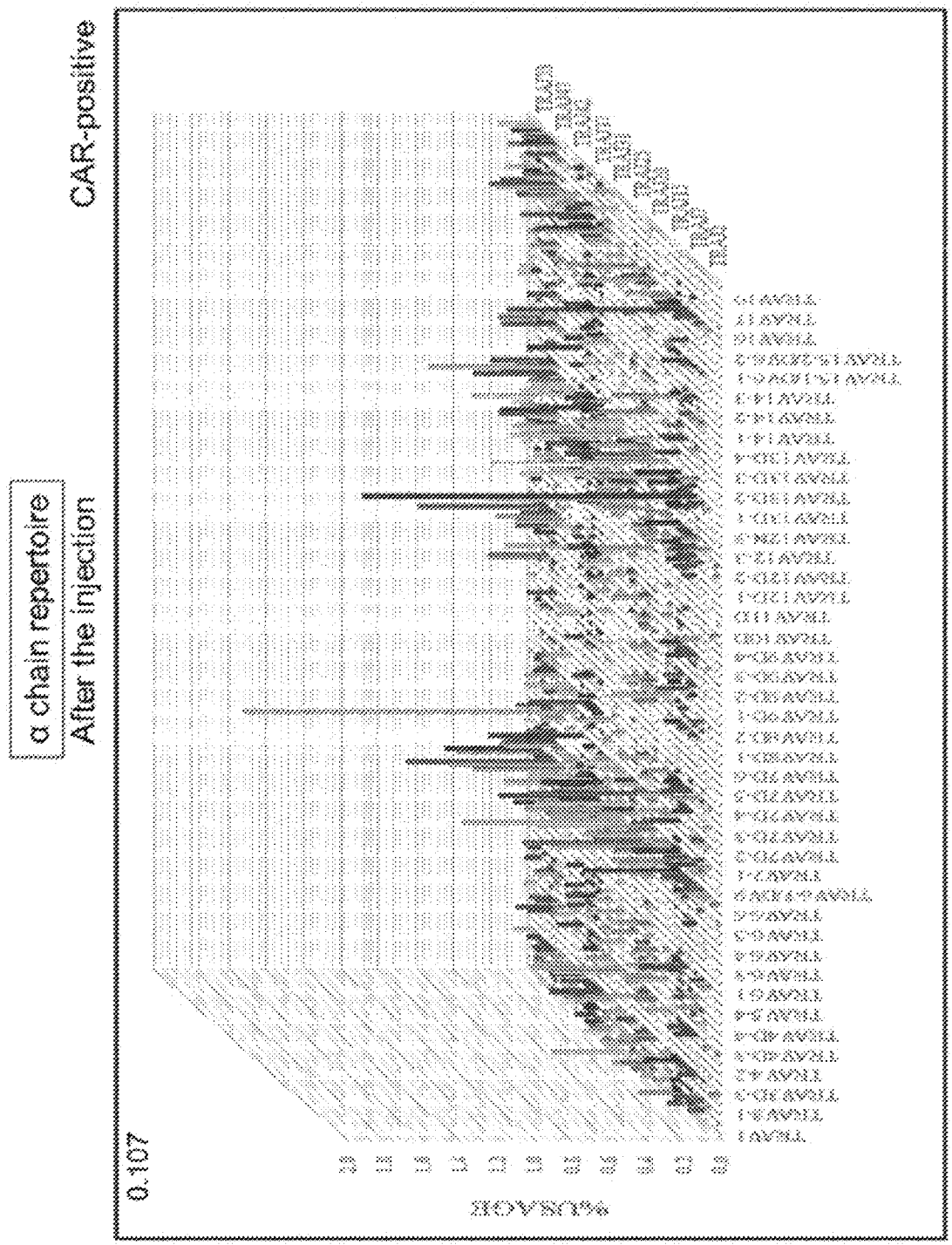

ENHANCER FOR T-CELLS OR B-CELLS HAVING MEMORY FUNCTION, MALIGNANT TUMOR RECURRENCE INHIBITOR, AND INDUCER FOR INDUCING MEMORY FUNCTION IN T-CELLS OR B-CELLS

CROSS REFERENCE TO RELATED APPLICATIONS

This application is a national stage filing under 35 U.S.C. § 371 of International Application No. PCT/JP2018/037608, filed on Oct. 9, 2018, which claims benefit of priority under 35 U.S.C. 119 to Japanese Patent Application No. 2017-196718, filed Oct. 10, 2017, the contents of both applications which are incorporated herein by reference in their entireties.

SEQUENCE LISTING

The instant application contains a Sequence Listing which has been submitted electronically in ASCII format and is hereby incorporated by reference in its entirety. The ASCII copy, created on Mar. 23, 2020, is named 38028.0061U1 SL.txt and is 11,953 bytes in size.

TECHNICAL FIELD

The present invention relates to an enhancer for T-cells or B-cells having a memory function in an administration subject, a malignant tumor recurrence inhibitor, and an inducer for inducing a memory function in T-cells or B-cells in an administration subject, comprising a nucleic acid delivery vehicle, a nucleic acid encoding interleukin-7 (IL-7), and a nucleic acid encoding chemokine (C-C motif) ligand 19 (CCL19).

BACKGROUND ART

Malignant tumor is a disease that affects many people worldwide. In general, chemotherapy, radiotherapy, or surgical therapy is widely practiced therefor. However, there have been various problems such as the occurrence of adverse reactions, a loss of some functions, and irremediableness of recurrence or metastasis. Accordingly, the development of immune cell therapy has been underway in recent years in order to keep patients' quality of life (QOL) high. This immune cell therapy is a therapy which involves collecting immune cells from a patient, treating the immune cells so as to enhance their immune function, amplifying the cells, and transferring the cells to the patient again. Specifically, a method is known which involves collecting T-cells from a patient, introducing a nucleic acid encoding CAR to the T-cells, amplifying the T-cells, and transferring the T-cells to the patient again (see non-patent document 1). This therapy is currently under clinical trial worldwide and has produced results that indicate efficacy for hematopoietic malignant tumor such as leukemia or lymphoma.

At least several hundreds of types of factors such as cytokines, chemokines, and signal regulatory proteins are known as immune function control factors for immune cells such as T-cells. Among them, interleukin-7 (IL-7) is a cytokine essential for the survival of T-cells and is known to be produced by non-hematopoietic cells such as stromal cells of the bone marrow, the thymus gland, and lymphoid organs or tissues. T-cells expressing a chimeric cytokine receptor of IL-7 and IL-7R alpha fused with each other (see patent document 1) are disclosed as T-cells exploiting the function of this IL-7. However, the chimeric cytokine receptor in these T-cells is expressed as one fusion protein in a manner limited to the membrane surface of the T-cells harboring the chimeric cytokine receptor, and merely transduces cytokine signals of IL-7R or the like to the self-cells in a ligand-independent manner. Thus, the chimeric cytokine receptor has failed to enhance the function of T-cells that do not harbor the receptor.

Other disclosures state that decreased expression of CCL19, CCL21, or IL-7 is responsible for the defective maintenance of a T-cell zone in the spleens of SIRP alpha mutant mice (see non-patent document 2) and that CCL19, CCL21, or IL-7 works to maintain the homeostasis of T-cells in secondary lymphoid tissues (spleen or lymph node) (see non-patent document 3). However, these non-patent documents 2 and 3 show action on nonactivated T-cells that constantly reside in the T-cell zones of secondary lymphoid tissues, and do not show direct relation to antitumor immune response. Furthermore, cells expressing CCL19, CCL21, or IL-7 in the non-patent documents 2 and 3 are cells of the reticuloendothelial system, not T-cells, residing in secondary lymphoid tissues.

Meanwhile, the present inventors have proposed immune cell therapy of markedly suppressing solid cancer by coexpressing IL-7 and CCL19 (see patent documents 2 and 3). This method can enhance the activation of endogenous immune cells or their ability to accumulate to tumor cells in a host (recipient). However, it is uncertain whether the immune cell therapy can prevent recurrence, etc. over a long period of time and continue to reject malignant tumor.

PRIOR ART DOCUMENTS

Patent Documents

Patent document 1: International Publication No. WO 2013/123061
Patent document 2: International Publication No. WO 2016/056228
Patent document 3: International Publication No. WO 2017/159736

Non-Patent Documents

Non-patent document 1: Yozo Nakazawa, The Shinshu Medical Journal, 61 (4): 197-203 (2013)
Non-patent document 2: SATO-HASHIMOTO M. et al., J. Immunol., 2011, vol. 187, no. 1, 291-7
Non-patent document 3: SIEGERT S. et al., Front. Immunol., 2012, vol. 3, article 285

SUMMARY OF THE INVENTION

Object to be Solved by the Invention

As mentioned above, immune cell therapy using CAR-expressing T-cells, TCR-expressing T-cells, or the like, coexpressing IL-7 and CCL19 has been developed, and the development of techniques of markedly improving the ability of immune cells to proliferate, the ability to survive, or the ability of host's immune cells to accumulate, and being adaptable to solid cancer on which conventional immune cell therapy has been found to have no sufficient therapeutic effect, are underway. However, malignant tumor often recurs. It is not clear whether or not the immune cell therapy continues to reject malignant tumor over a long period of time even if the malignant tumor can be temporarily treated. Furthermore, preventive measures against recurrence have not been discussed. Accordingly, an object of the present invention is to provide an enhancer for endogenous T-cells or B-cells having a memory function, a malignant tumor recurrence inhibitor, and an inducer for inducing a memory function in endogenous T-cells or B-cells in order to continue to reject malignant tumor over a long period of time.

Means to Solve the Object

The present inventors have studied the further possibilities of the previously developed T-cells expressing CAR, IL-7 and CCL19 and consequently found that: the administration of the T-cells to a subject induces a memory function not only in the administered T-cells but in endogenous T-cells in the subject (host) and increases the absolute number of cells having a memory function; and in a recurrence model experiment of malignant tumor, this administration suppresses malignant tumor formation in cells having no antigen that is recognized by CAR. The present inventors have further found that use of TCR instead of CAR or use of a virus instead of T-cells also produces similar effects. On the basis of these findings, the present invention has been completed.

Specifically, the present invention is as follows.
(1) An enhancer for T-cells or B-cells having a memory function in an administration subject, comprising a nucleic acid delivery vehicle, a nucleic acid encoding interleukin-7 (IL-7), and a nucleic acid encoding chemokine (C-C motif) ligand 19 (CCL19).
(2) The enhancer for T-cells or B-cells having a memory function in an administration subject according to (1), wherein the nucleic acid delivery vehicle is at least one member selected from an immune cell, a virus, an anaerobe, a liposome, a mesenchymal stem cell (MSC), and a nanoparticle.
(3) The enhancer for T-cells or B-cells having a memory function in an administration subject according to (1) or (2), wherein the nucleic acid delivery vehicle has an ability to accumulate to malignant tumor cells, or an ability to proliferate specifically in malignant tumor cells.
(4) The enhancer for T-cells or B-cells having a memory function in an administration subject according to any one of (1) to (3), wherein the nucleic acid delivery vehicle has a cytotoxicity against malignant tumor cells.
(5) The enhancer for T-cells or B-cells having a memory function in an administration subject according to any one of (1) to (4), wherein the nucleic acid delivery vehicle is an immune cell, and the immune cell has a cell surface molecule that recognizes a malignant tumor antigen.
(6) The enhancer for T-cells or B-cells having a memory function in an administration subject according to (5), wherein the cell surface molecule that recognizes a malignant tumor antigen is a chimeric antigen receptor (CAR) or a T-cell receptor (TCR).
(7) The enhancer for T-cells or B-cells having a memory function in an administration subject according to (5) or (6), wherein the immune cell is a T-cell.
(8) The enhancer for T-cells or B-cells having a memory function in an administration subject according to any one of (1) to (7), wherein the T-cells or B-cells having a memory function are central memory T-cells.
(9) A pharmaceutical composition comprising an enhancer for T-cells or B-cells having a memory function in an administration subject according to any one of (1) to (8) and a pharmaceutically acceptable additive.
(10) A malignant tumor recurrence inhibitor comprising a nucleic acid delivery vehicle, a nucleic acid encoding interleukin-7 (IL-7), and a nucleic acid encoding chemokine (C-C motif) ligand 19 (CCL19).
(11) The malignant tumor recurrence inhibitor according to (10), wherein the nucleic acid delivery vehicle is at least one member selected from an immune cell, a virus, an anaerobe, a liposome, a mesenchymal stem cell (MSC), and a nanoparticle.
(12) The malignant tumor recurrence inhibitor according to (10) or (11), wherein the nucleic acid delivery vehicle has an ability to accumulate to malignant tumor cells, or an ability to proliferate specifically in malignant tumor cells.
(13) The malignant tumor recurrence inhibitor according to any one of (10) to (12), wherein the nucleic acid delivery vehicle has a cytotoxicity against malignant tumor cells.
(14) The malignant tumor recurrence inhibitor according to any one of (10) to (13), wherein the nucleic acid delivery vehicle is an immune cell, and the immune cell has a cell surface molecule that recognizes a malignant tumor antigen.
(15) The malignant tumor recurrence inhibitor according to (14), wherein the nucleic acid delivery vehicle is an immune cell having a cell surface molecule that recognizes a malignant tumor cell antigen, and the malignant tumor recurrence is a malignant tumor recurrence ascribable to a malignant tumor cell having no malignant tumor antigen that is specifically recognized by the cell surface molecule.
(16) The malignant tumor recurrence inhibitor according to (14) or (15), wherein the cell surface molecule that recognizes a malignant tumor cell antigen is a chimeric antigen receptor (CAR) or a T-cell receptor (TCR).
(17) The malignant tumor recurrence inhibitor according to any one of (14) to (16), wherein the immune cell is a T-cell.
(18) The malignant tumor recurrence inhibitor according to (11), wherein the nucleic acid delivery vehicle is an oncolytic virus.
(19) A pharmaceutical composition comprising a malignant tumor recurrence inhibitor according to any one of (10) to (18) and a pharmaceutically acceptable additive.
(20) An inducer for inducing a memory function in T-cells or B-cells in an administration subject, comprising a nucleic acid delivery vehicle, a nucleic acid encoding interleukin-7 (IL-7), and a nucleic acid encoding chemokine (C-C motif) ligand 19 (CCL19).

Other aspects of the present invention are as follows.
1) Use of a nucleic acid delivery vehicle, a nucleic acid encoding interleukin-7 (IL-7), and a nucleic acid encoding chemokine (C-C motif) ligand 19 (CCL19) for the preparation of an enhancer for T-cells or B-cells having a memory function in an administration subject.
2) A method for enhancing T-cells or B-cells having a memory function, comprising administering a nucleic acid delivery vehicle, a nucleic acid encoding interleukin-7 (IL-7), and a nucleic acid encoding chemokine (C-C motif) ligand 19 (CCL19) to a subject.
3) Use of a nucleic acid delivery vehicle, a nucleic acid encoding interleukin-7 (IL-7), and a nucleic acid encoding chemokine (C-C motif) ligand 19 (CCL19) for the preparation of a malignant tumor recurrence inhibitor.
4) A method for inhibiting malignant tumor recurrence, comprising administering a nucleic acid delivery vehicle, a nucleic acid encoding interleukin-7 (IL-7), and a nucleic acid encoding chemokine (C-C motif) ligand 19 (CCL19) to a subject.
5) Use of a nucleic acid delivery vehicle, a nucleic acid encoding interleukin-7 (IL-7), and a nucleic acid encoding chemokine (C-C motif) ligand 19 (CCL19) for the preparation of an inducer for inducing a memory function in T-cells or B-cells in an administration subject.

6) A method for inducing a memory function in T-cells or B-cells, comprising administering a nucleic acid delivery vehicle, a nucleic acid encoding interleukin-7 (IL-7), and a nucleic acid encoding chemokine (C-C motif) ligand 19 (CCL19) to a subject.

7) The inducer for inducing a memory function in T-cells or B-cells in an administration subject according to (20), wherein the nucleic acid delivery vehicle is at least one member selected from an immune cell, a virus, an anaerobe, a liposome, a mesenchymal stem cell (MSC), and a nanoparticle.

8) The inducer for inducing a memory function in T-cells or B-cells in an administration subject according to (20) or 7), wherein the nucleic acid delivery vehicle has the ability to accumulate to malignant tumor cells, or the ability to proliferate specifically in malignant tumor cells.

9) The inducer for inducing a memory function in T-cells or B-cells in an administration subject according to (20), 7), or 8), wherein the nucleic acid delivery vehicle has a cytotoxicity against malignant tumor cells.

10) The inducer for inducing a memory function in T-cells or B-cells in an administration subject according to any one of (20) and 7) to 9), wherein the nucleic acid delivery vehicle is an immune cell, and the immune cell has a cell surface molecule that recognizes a malignant tumor antigen.

11) The inducer for inducing a memory function in T-cells or B-cells in an administration subject according to 10), wherein the cell surface molecule that recognizes a malignant tumor antigen is a chimeric antigen receptor (CAR) or a T-cell receptor (TCR).

12) The inducer for inducing a memory function in T-cells or B-cells in an administration subject according to 10) or 11), wherein the immune cell is a T-cell.

Effect of the Invention

Use of the enhancer for T-cells or B-cells having a memory function according to the present invention enables enhancement in T-cells or B-cells having a memory function in an administration subject. Furthermore, use of the malignant tumor recurrence inhibitor of the present invention enables inhibition of recurrence of malignant tumor after treatment. Use of the inducer for inducing a memory function in T-cells or B-cells according to the present invention enables induction of a memory function in T-cells or B-cells in an administration subject.

BRIEF DESCRIPTION OF DRAWINGS

FIG. 4 is a graph showing results about Example 3 in which administered donor T-cells and endogenous T-cells of a recipient were examined for their function of memory potential by the production of IFN-γ. FIG. 4(a) shows the ratio of IFN-γ-positive cells to CD90.1-positive donor T-cells. FIG. 4(b) shows results of detecting IFN-γ-positive cells in CD90.2-positive and endogenous CD8-positive T-cells by flow cytometry.

FIG. 5C is a graph showing results about Example 4 in which change in T-cell receptor (TCR) repertoire after treatment with CAR-IL-7/CCL19-expressing T-cells (α chain: after treatment, CAR-positive) was examined.

CCL19-expressing T-cells (7×19 CAR-T) and a group given conventional anti-human mesothelin CAR-expressing T-cells (conventional CAR-T) on day 1 were photographed for an exposure time of 30 seconds. The second individual counted from the left on day 129 was dead, so that its photograph is omitted.

Figure 10:
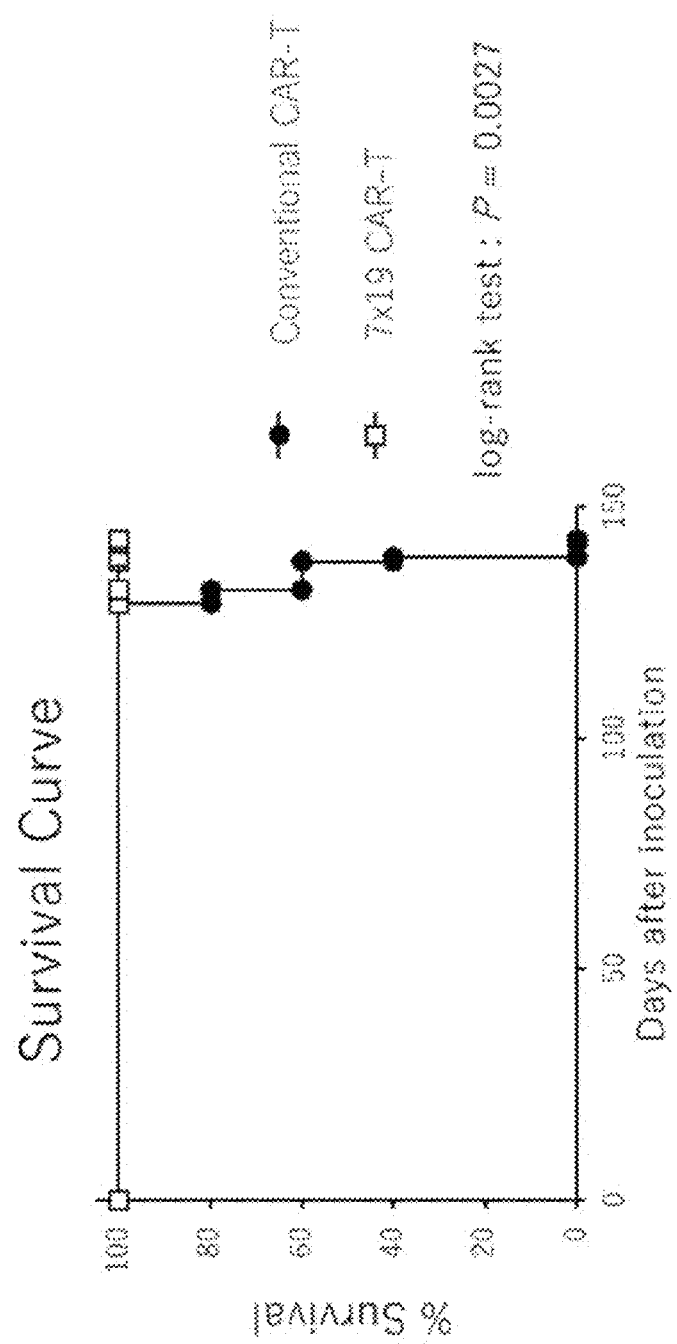

FIG. 10 is a graph showing the relationship between the number of days from administration of ACC-MESO1-GFP-Luc mentioned later and the survival rates of mice in Example 6.

Figure 11:
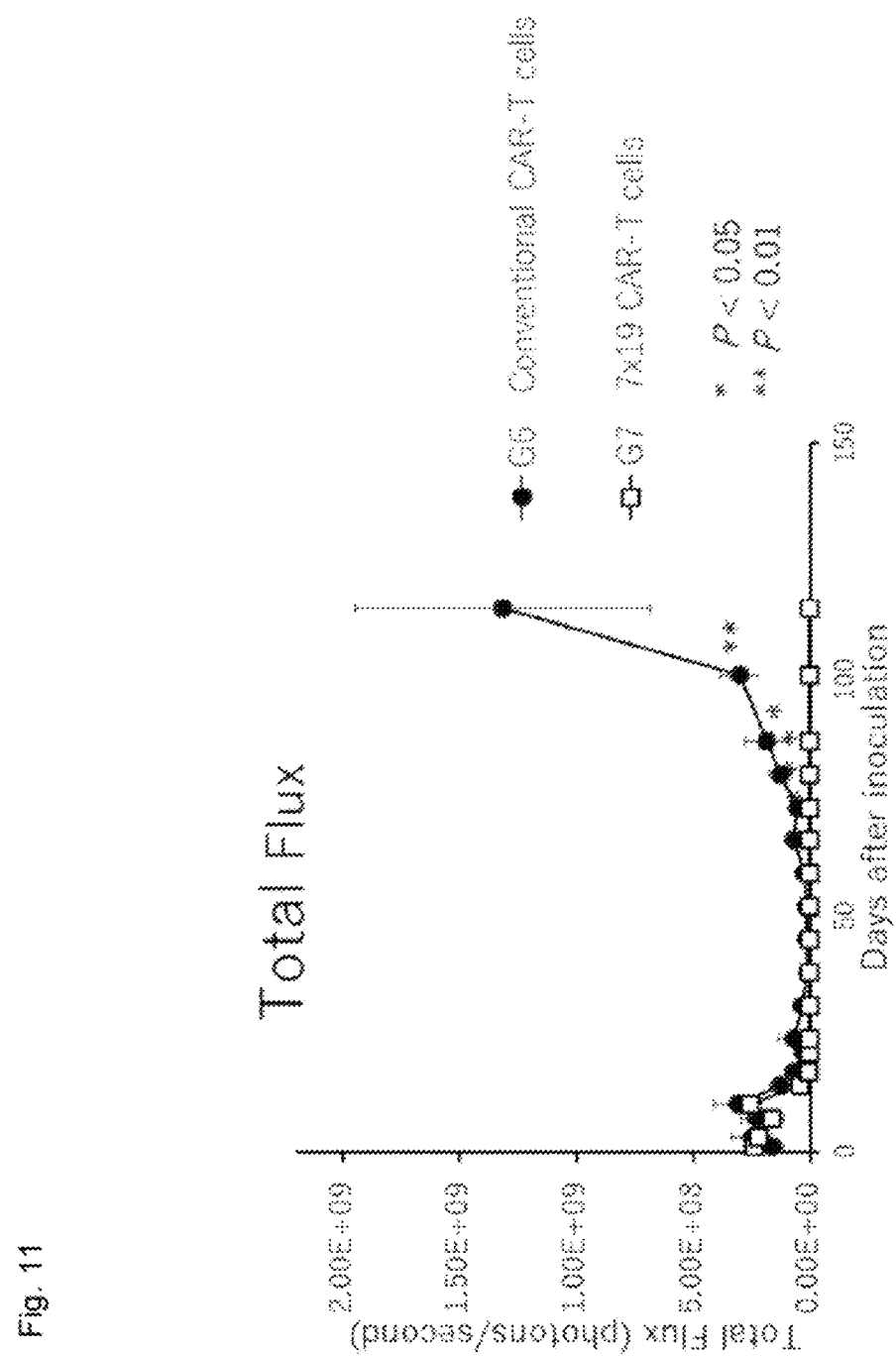

FIG. 11 is a graph showing the relationship between the number of days from administration of ACC-MESO1-GFP-Luc mentioned later and the total amount of fluorescence in Example 6.

Figure 12:
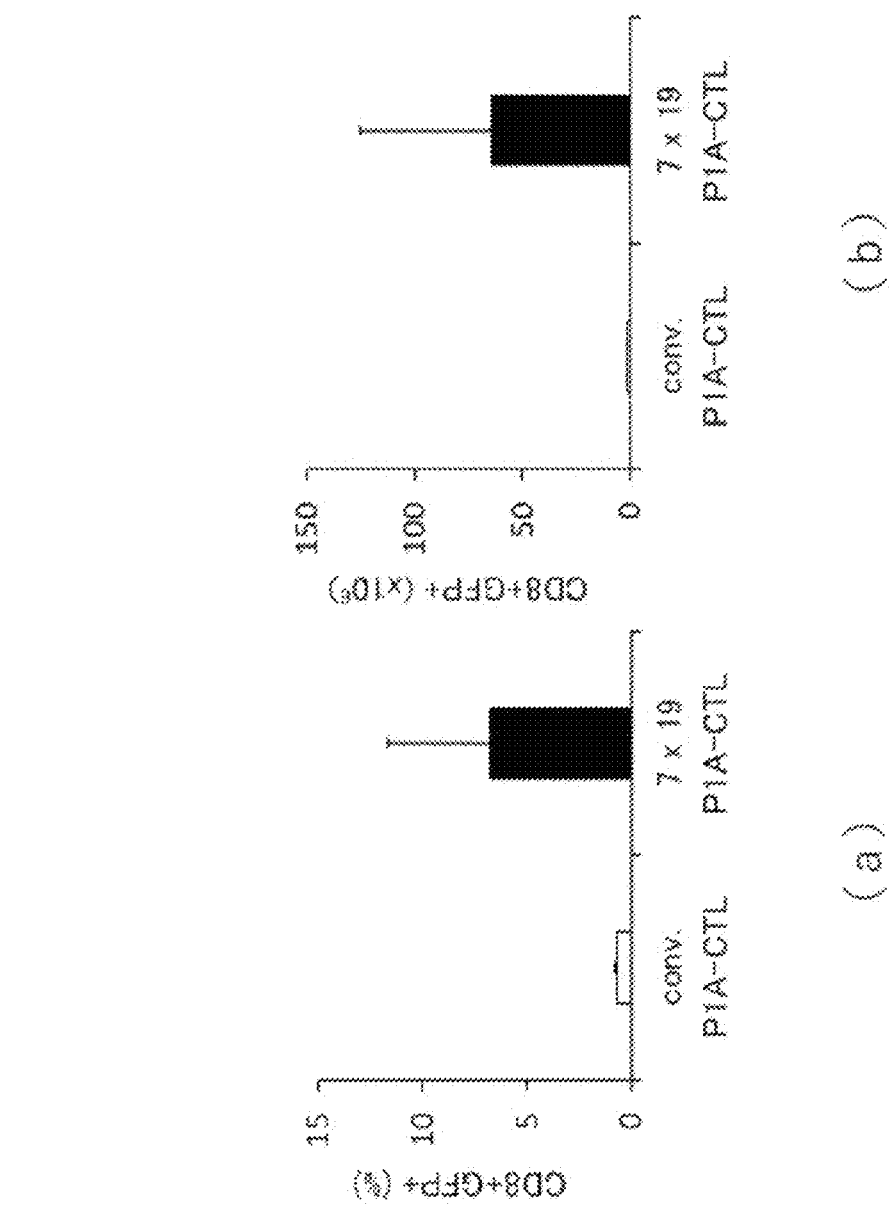

FIG. 12(a) is a diagram showing results about Example 7 in which the ratio of CD8$^+$GFP$^+$ cells to spleen cells was analyzed by flow cytometry. FIG. 12(b) is a diagram showing results about Example 7 in which the absolute number of CD8$^+$GFP$^+$ cells was analyzed by flow cytometry.

Figure 13:
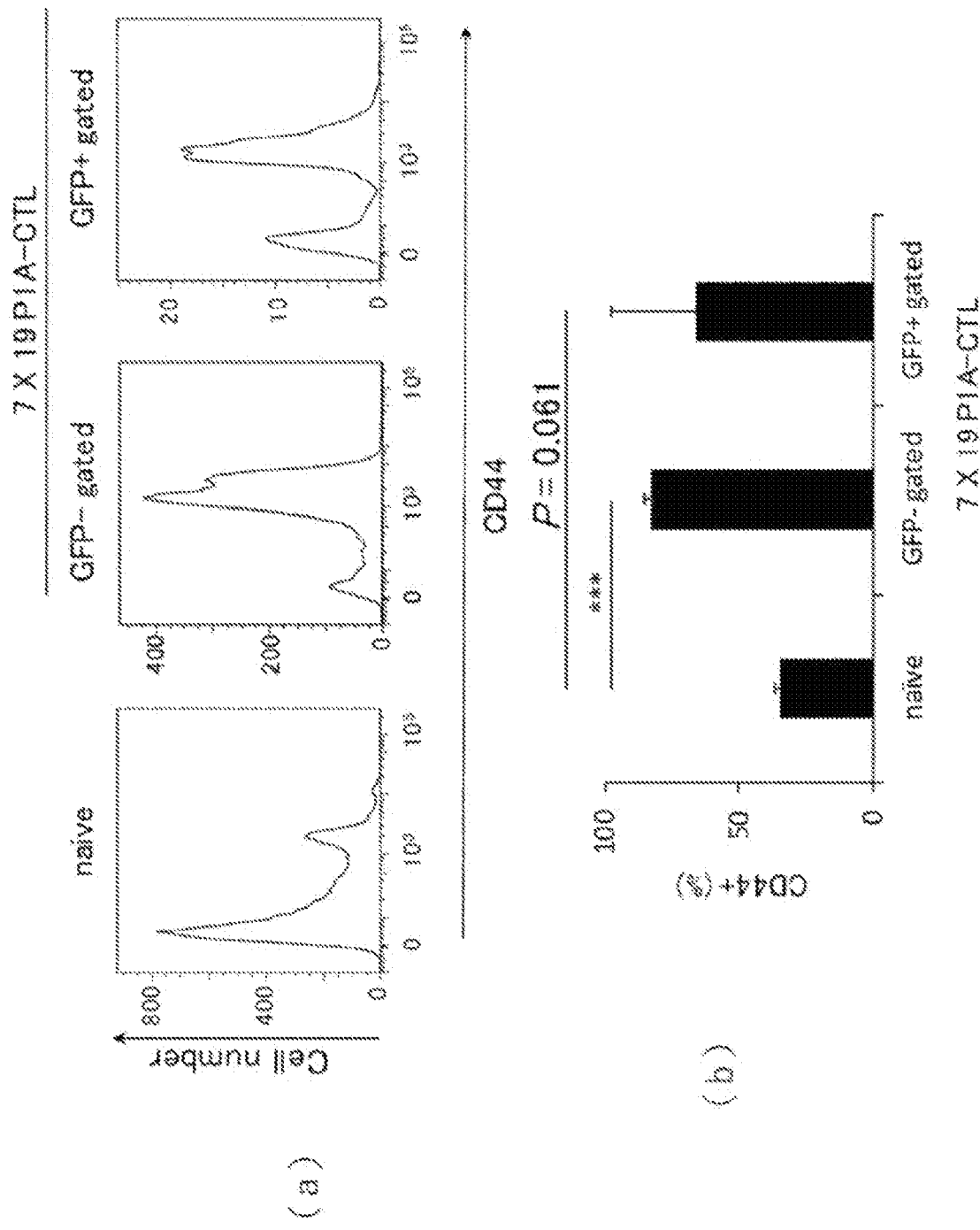

FIG. 13(a) is a diagram showing the number of CD44$^+$ cells in CD8$^+$ spleen cells of naive BDA/2 mice and CD8$^+$ GFP$^-$ or CD8$^+$GFP$^+$ spleen cells of mice treated with P1A-specific TCR/IL-7/CCL19/eGFP-expressing T-cells in Example 7. FIG. 13(b) is a diagram showing the ratio of the CD44$^+$ cells in FIG. 13(a).

Figure 14:
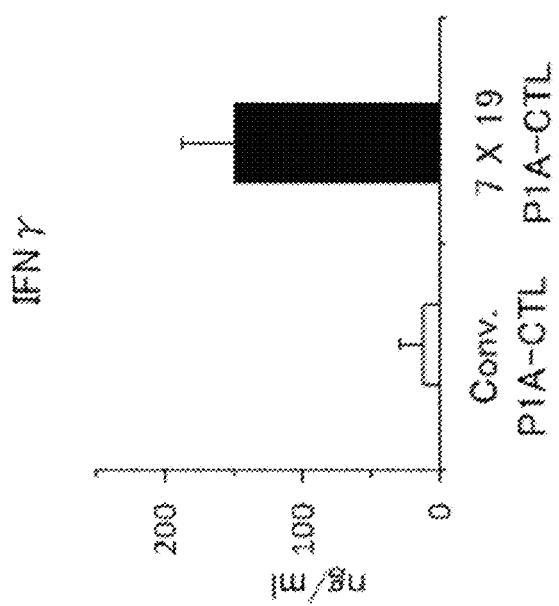

FIG. 14 is a diagram showing results about Example 7 in which after coculture for approximately 5 days with mucosal mast cells (MMC) treated with P815, the concentration of IFN-γ in a supernatant of the culture medium was detected by ELISA (enzyme-linked immunosorbent assay).

Figure 15:
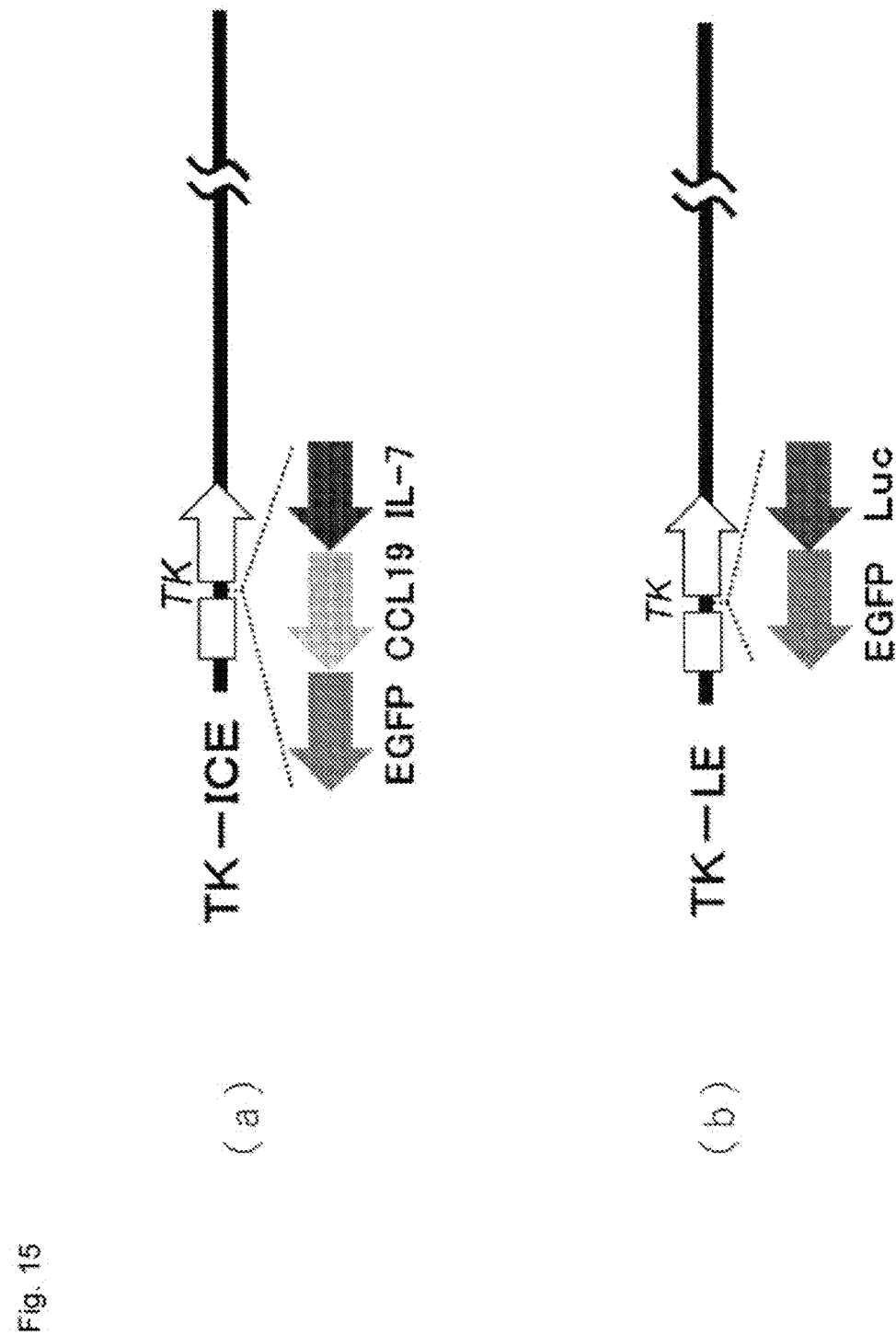

FIG. 15(a) is a diagram showing the structure of genetically recombinant vaccinia virus LC16mO TK-SP-mouse IL-7-F2A-mouse CCL19-F2A-eGFP (TK-ICE) in Example 8. FIG. 15(b) is a diagram showing the structure of genetically recombinant vaccinia virus LC16mO TK-SP-Luc-F2A-eGFP (TK-LE) in Example 8.

Figure 16:
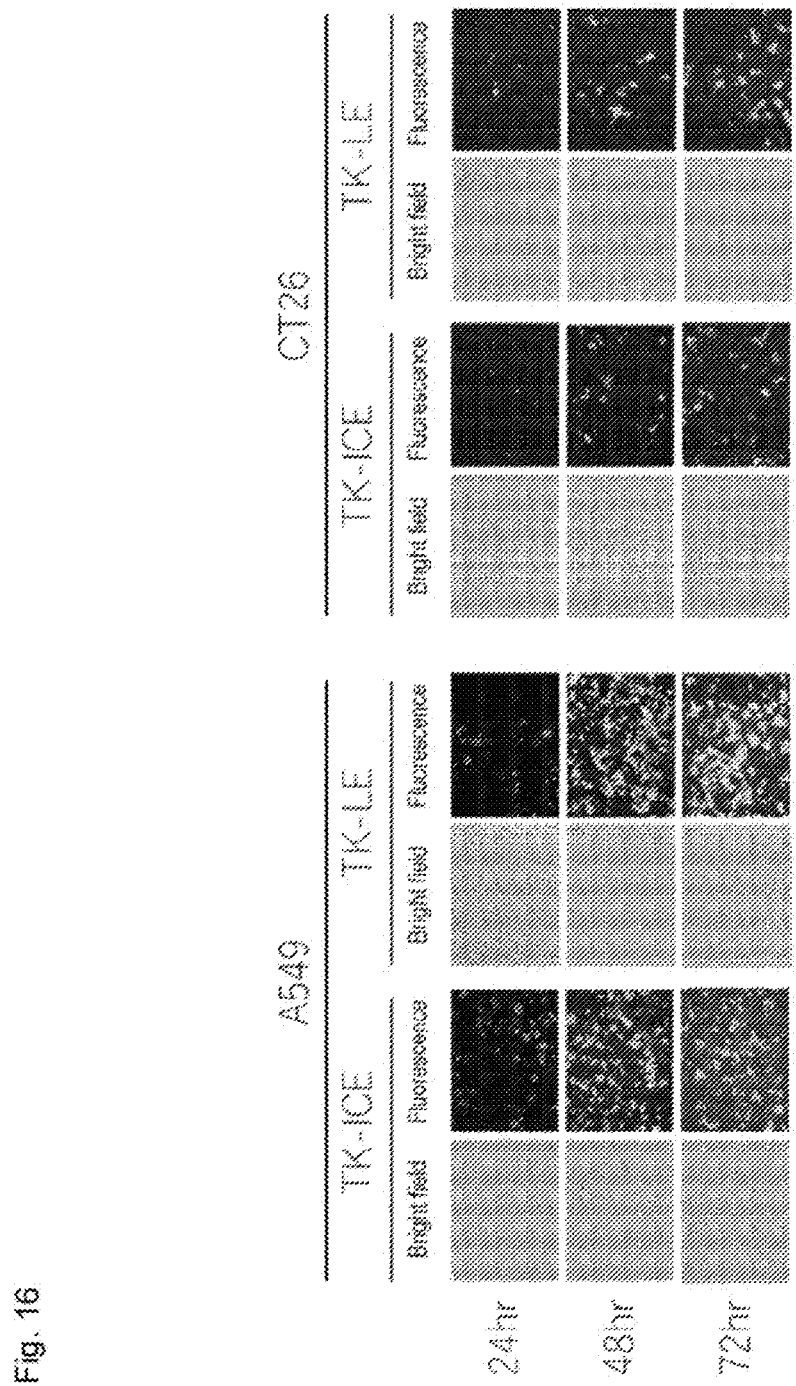

FIG. 16 is a diagram showing observation images of the relationship between the cytopathic effect of genetically recombinant vaccinia virus TK-ICE or TK-LE in A549 cells and CT26 cells infected with the vaccinia virus, and eGFP fluorescence emission in Example 8.

Figure 17:
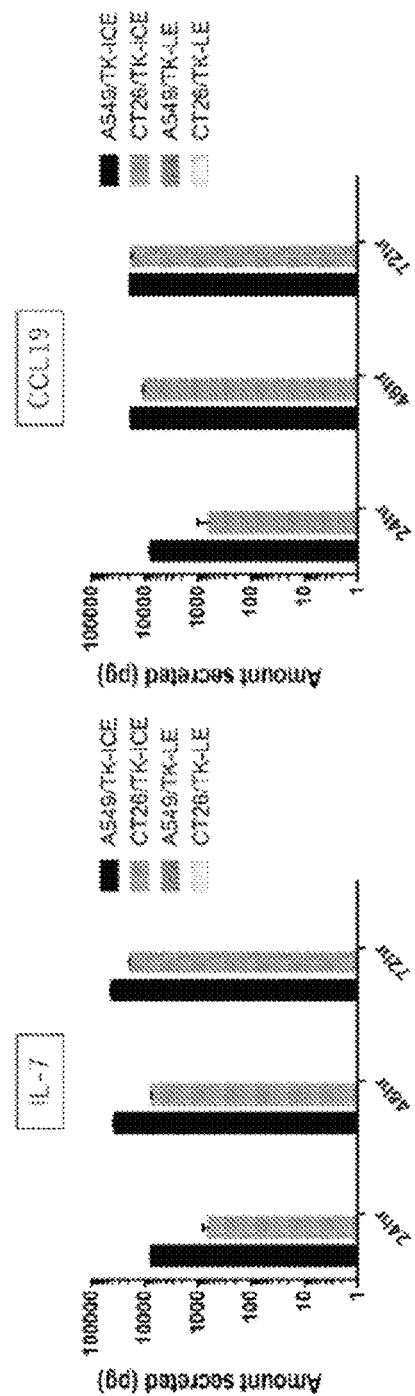

FIG. 17 is a diagram showing results of examining the amounts of IL-7 and CCL19 secreted in A549 cells or CT26 cells infected with genetically recombinant vaccinia virus TK-ICE or TK-LE in Example 8.

Figure 18:
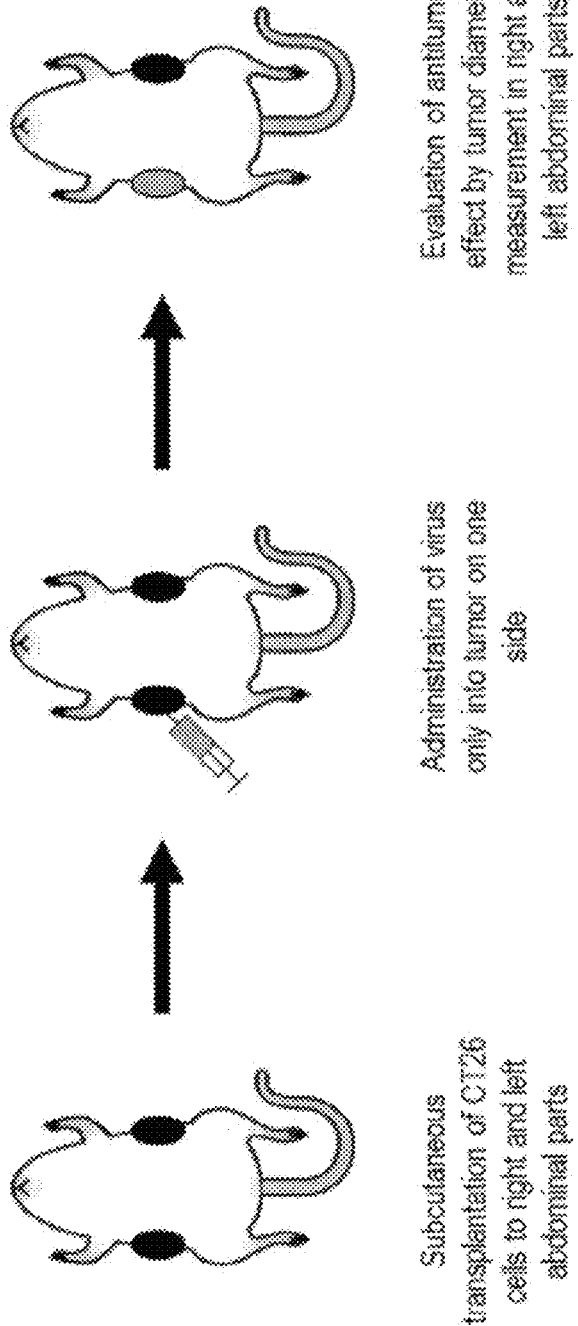

FIG. 18 is a diagram conceptually showing the subcutaneous transplantation of mouse large intestine cancer CT26 cells to right and left abdominal parts of a mouse in Example 8.

Figure 19:
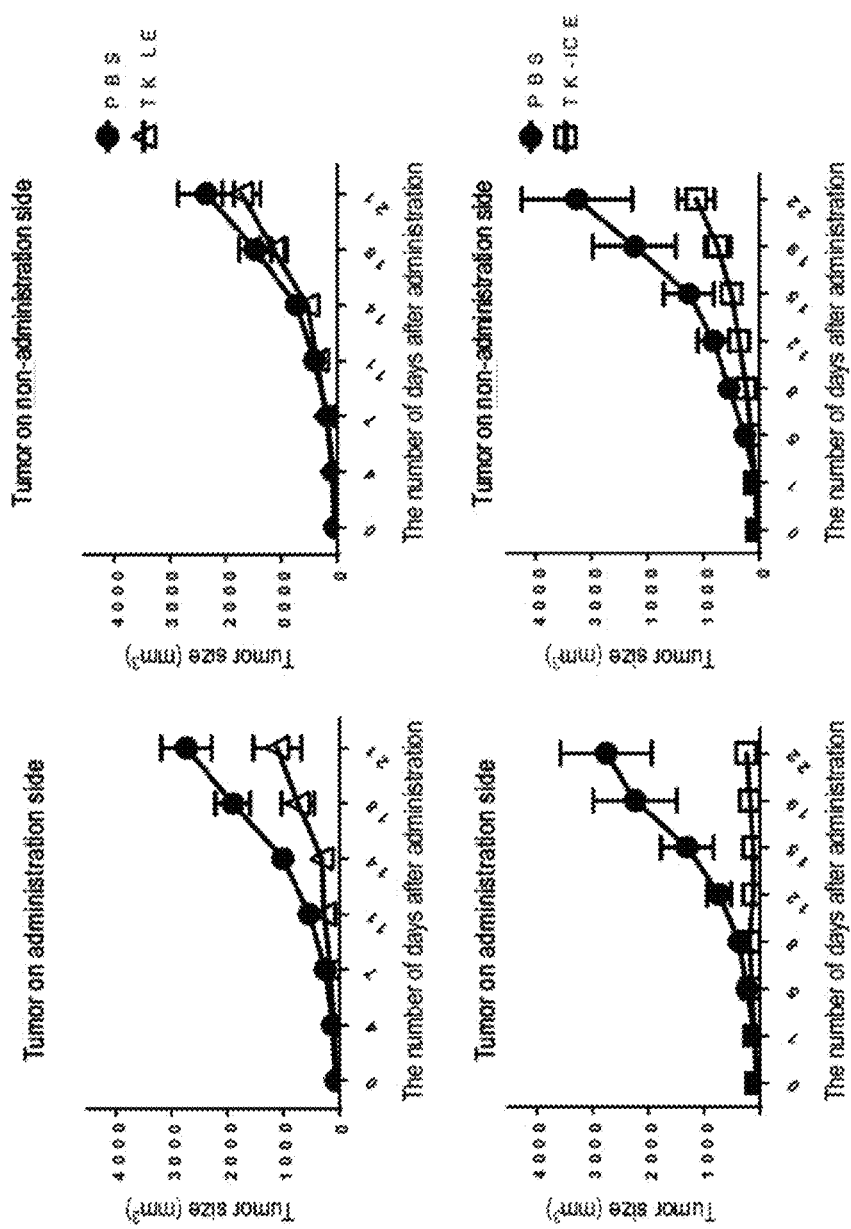

FIG. 19 is a diagram showing transitional change in tumor size (mm$^3$) after intratumoral administration of genetically recombinant vaccinia virus TK-ICE or TK-LE to bilaterally subcutaneously tumor-transplanted BALB/c mouse models obtained using mouse large intestine cancer cells CT26 in Example 9.

MODE OF CARRYING OUT THE INVENTION

In the present specification, the "enhancer for T-cells or B-cells having a memory function" is not particularly limited as long as the enhancer comprises a nucleic acid delivery vehicle, a nucleic acid encoding IL-7, and a nucleic acid encoding CCL19. This enhancer enables enhancement in T-cells or B-cells having a memory function. In the present specification, the "inducer for inducing a memory function in T-cells or B-cells" is not particularly limited as long as the inducer comprises a nucleic acid delivery vehicle, a nucleic acid encoding IL-7, and a nucleic acid encoding CCL19. This inducer enables induction of a memory function in T-cells or B-cells. Hereinafter, in the present specification, the "enhancer for T-cells or B-cells having a memory function" and the "inducer for inducing a memory function in T-cells or B-cells" are also collectively referred to as the "present enhancer or inducer".

In the present specification, the "malignant tumor recurrence inhibitor" is not particularly limited as long as the malignant tumor recurrence inhibitor comprises a nucleic acid delivery vehicle, a nucleic acid encoding IL-7, and a nucleic acid encoding CCL19. This malignant tumor recurrence inhibitor enables inhibition of malignant tumor recurrence. Hereinafter, in the present specification, the "malignant tumor recurrence inhibitor" is also referred to as the "present malignant tumor recurrence inhibitor".

Preferred examples of the nucleic acid encoding IL-7 and the nucleic acid encoding CCL19 can include a human-derived nucleic acid. Each of these nucleic acids can be appropriately selected according to the type of cells for introduction. Sequence information on each of the nucleic acids can be appropriately retrieved from a document known in the art or a database such as NCBI (ncbi.nlm.nih.gov/guide/). Examples of the nucleic acid encoding IL-7 can include the nucleotide sequence of a nucleic acid encoding the amino acid sequence set forth in SEQ ID NO: 1. The nucleotide sequence of a nucleic acid encoding an amino acid sequence having 80% or higher, preferably 85% or higher, more preferably 90% or higher, further preferably 95% or higher, most preferably 98% or higher sequence identity to the amino acid sequence set forth in SEQ ID NO: 1 may be used as long as the resulting IL-7 has the action of increasing a cell proliferation rate or a cell survival rate. Examples of the nucleic acid encoding CCL19 can include the nucleotide sequence of a nucleic acid encoding the amino acid sequence set forth in SEQ ID NO: 2. The nucleotide sequence of a nucleic acid encoding an amino acid sequence having 80% or higher, preferably 85% or higher, more preferably 90% or higher, further preferably 95% or higher, most preferably 98% or higher sequence identity to the amino acid sequence set forth in SEQ ID NO: 2 may be used as long as the resulting CCL19 has the action of migrating cells. The action of increasing a cell proliferation rate or a cell survival rate by IL-7 and the action of migrating cells by CCL19 can be confirmed by methods described in patent document 2.

In the present specification, the term "identity" means the degree of polypeptide or polynucleotide sequence similarity (which is determined by the matching of a query sequence with another sequence, preferably, of the same type (nucleic acid or protein sequence)). Preferred examples of the computer program method for calculating and determining the "identity" can include GCG BLAST (basic local alignment search tool) (Altschul et al., J. Mol. Biol. 1990, 215: 403-410; Altschul et al., Nucleic Acids Res. 1997, 25: 3389-3402; and Devereux et al., Nucleic Acid Res. 1984, 12: 387), BLASTN 2.0 (Gish W., blast.Wustl.edu, 1996-2002), FASTA (Pearson and Lipman, Proc. Natl. Acad. Sci. USA 1988, 85: 2444.2448), and GCG GelMerge which involves determining and aligning a pair of contigs with the longest overlap (Wibur and Lipman, SIAM J. Appl. Math. 1984, 44: 557-567; and Needleman and Wunsch, J. Mol. Biol. 1970, 48: 443-453).

The nucleic acid encoding IL-7 and/or the nucleic acid encoding CCL19 may be incorporated in a vector containing a control sequence such as a promoter or a terminator, and a selective marker sequence such as a drug resistance gene or a reporter gene. The vector may further contain a nucleic acid encoding suicide gene, or a nucleic acid encoding 2A peptide or IRES. The vector, the nucleic acid encoding suicide gene, and the nucleic acid encoding 2A peptide or IRES can be obtained or prepared with reference to patent documents 2 and 3. Examples of the promoter can include cytomegalovirus (CMV) IE (immediate early) gene promoter, SV40 early promoter, retrovirus promoter, metallothionein promoter, heat shock promoter, SRα promoter, NFAT promoter, and HIF promoter. Examples of the vector can include a retrovirus vector such as pMSGV vector (Tamada k et al., Clin Cancer Res 18: 6436-6445 (2002)) and pMSCV vector (manufactured by Takara Bio Inc.), and a vector derived from any of these vectors.

A nucleic acid encoding an additional immune function control factor such as IL-15, CCL21, IL-2, IL-4, IL-12, IL-13, IL-17, IL-18, IP-10, CCL4, Flt3L, interferon-γ, MIP-1α, GM-CSF, M-CSF, TGF-β, TNF-α, a checkpoint inhibitory antibody, or a fragment thereof may be contained together with the nucleic acid encoding IL-7 and the nucleic acid encoding CCL19. However, the present enhancer or inducer or the present malignant tumor recurrence inhibitor, even free from the nucleic acid encoding the additional immune function control factor, can sufficiently exert an effect as the present enhancer or inducer or the present malignant tumor recurrence inhibitor as long as the present enhancer or inducer or the present malignant tumor recurrence inhibitor contains at least the nucleic acid encoding IL-7 and the nucleic acid encoding CCL19 as nucleic acids encoding immune function control factors.

The "memory function" means a function of more rapidly and strongly activating T-cells or B-cells that have previously experienced stimulation with a tumor antigen and come into contact with malignant tumor cells again, as compared with naive T-cells or naive B-cells without previous stimulation with the tumor antigen, and thereby allowing the T-cells or the B-cells to exert high immune function against the malignant tumor cells. Examples of the T-cells or B-cells having a memory function can include central memory T-cells and memory B-cells. These T-cells or B-cells having a memory function can be confirmed by comprehensively evaluating positivity/negativity (+/−) to or expression intensity of each of CD44, CD62L, and CD127 (IL-7R). The CD molecule to be measured can be appropriately selected according to a subject such as a human or a mouse. Hereinafter, in the present application, the positivity and the negativity are also described as "+" and "−", respectively.

The "enhancement in T-cells or B-cells having a memory function" means increase in the ratio of the T-cells or B-cells having a memory function, increase in the absolute number of the T-cells or B-cells having a memory function, or enhancement in the memory function per cell of the T-cells or B-cells having a memory function, in a cell population including the T-cells or B-cells having a memory function.

The "induction of a memory function in T-cells or B-cells" means induction of naive T-cells or naive B-cells so as to have a memory function by acquiring immune memory in response to stimulation with a tumor antigen, induction of T-cells or B-cells already having a memory function so as to have a higher memory function, and increase in the number of T-cells or B-cells already having a memory function in vivo, in a cell population including the naive T-cells or the naive B-cells. Specific examples thereof can include induction of naive T-cells into central memory T-cells.

Preferred examples of the administration subject can include a mammal and mammalian cells. Among the mammals, more preferred examples thereof can include a human, a mouse, a dog, a rat, a guinea pig, a rabbit, a bird, a sheep, a pig, a cattle, a horse, a cat, a monkey, and a chimpanzee, particularly preferably a human.

The "nucleic acid delivery vehicle" can be at least one member selected from an immune cell, a virus, an anaerobe, a liposome, a mesenchymal stem cell (MSC), and a nanoparticle, two or more of which may be mixed and used.

In this context, the immune cell is not particularly limited as long as the cell is involved in immune response and can express IL-7 and CCL19 by the introduction of the nucleic acid encoding IL-7 and the nucleic acid encoding CCL19. An immune cell separated (collected) from a living body is preferred. Examples thereof can include a separated form of a lymphoid lineage cell such as a T-cell, a natural killer cell (NK cell), and a B-cell, an antigen-presenting cell such as a monocyte, a macrophage, and a dendritic cell, or a granulocyte such as a neutrophil, an eosinophil, a basophil, and a mast cell, and can preferably include a T-cell separated from a mammal such as a human, a dog, a cat, a pig, or a mouse, preferably a T-cell separated from a human. The separated T-cells may additionally include cells other than T-cells and can include the T-cells at a proportion of 50% or more, preferably 60% or more, more preferably 70% or more, further preferably 80% or more, most preferably 90% or more. The T-cells can be obtained by separating a cell population including the immune cell from a body fluid such as blood or bone marrow fluid, a tissue such as a spleen tissue, a thymic tissue, or a lymph node, or immune cells infiltrating a cancer tissue such as primary tumor, metastatic tumor, or cancerous ascites. In order to elevate the ratio of T-cells included in the cell population, the cell population thus separated may be further subjected to isolation or purification, if necessary, by a standard method to obtain the T-cells. Alternatively, T-cells prepared from ES cells or iPS cells may be utilized. Examples of such a T-cell can include an alpha-beta T-cell, a gamma-delta T-cell, a $CD8^+$ T-cell, a $CD4^+$ T-cell, a tumor-infiltrating T-cell, a memory T-cell, a naive T-cell, and a NK T-cell. The origin of the immune cell and the administration subject may be the same or different and is preferably the same. When the administration subject is a human, an autologous cell collected from a patient as the administration subject, or an allogeneic cell collected from another person may be used as the immune cell. Specifically, the donor and the recipient may be the same or different and is preferably the same.

The virus is not particularly limited as long as the virus can enclose the nucleic acid encoding IL-7 and the nucleic acid encoding CCL19 and is capable of infecting malignant tumor cells. An oncolytic virus is preferred. The oncolytic virus means a virus that rarely proliferates upon infection in normal cells, but proliferates upon infection in malignant tumor cells, and has the ability to kill the malignant tumor cells (cytotoxicity against malignant tumor cells). The oncolytic virus is reviewed in, for example, Molecular Therapy, Vol. 18, No. 2, February 2010, p. 233-234. This oncolytic virus is not particularly limited as long as the oncolytic virus has the ability to kill malignant tumor cells by infecting the malignant tumor cells. Examples thereof can include oncolytic vaccinia virus, oncolytic adenovirus, oncolytic herpes simplex virus, oncolytic reovirus, oncolytic measles virus, oncolytic Newcastle disease virus, oncolytic cowpox virus, oncolytic mumps virus, and oncolytic coxsackievirus. Examples of the oncolytic vaccinia virus that may be used include, but are not limited to, a virus described in Kim M K et al., Science Translational Medicine. 2013 May 15; 5 (185): 185ra63, Heo J, et al., Nature Medicine, 2013 (3):

329-36. doi: 10.1038/nm.3089. Epub 2013 Feb. 10., and International Publication No. WO 2012/094386. Examples of the oncolytic adenovirus that may be used include, but are not limited to, a virus described in Tedcastle A et al., Mol Ther. 2016; 24: 796-804, Marino N, Illingworth S, Kodialbail P, Patel A, Calderon H, Lear R, Fisher K D, Champion B R, Brown A C N. PLoS One 2017; 12 (5): e0177810, Freedman J D, et al., EMBO Mol Med 9: 1067-1087 (2017), Lang F F et al., Journal of Clinical Oncology (2018), James M. et al., The Journal of Oncology, 188 (6): 2391-7, 2012, and Japanese Patent Nos. 3867968 and 5574284. Examples of the oncolytic herpes simplex virus that may be used include, but are not limited to, a virus described in Mazzacurati et al., Mol Ther, 2015 January; 23 (1): 99-107, Hirooka Y, et al., BMC Cancer 2018, 18, 596, Nakatake R, et al., Cancer Sci. 2018 March, 109 (3); 600-610, and Andtbacka R H I, et al., J Clin Oncol. 2015; 33: 2780-2788. Examples of the oncolytic reovirus that may be used include, but are not limited to, a virus described in Mahalingam, et al., Cancers 2018, 10, 160. Examples of the oncolytic Newcastle disease virus that may be used include, but are not limited to, a virus described in Journal of Virology. 2016 June; 90 (11): 5343-5352. Examples of the oncolytic vesicular stomatitis virus that may be used include, but are not limited to, a virus described in Muik A. et al., Cancer Res; 74 (13); 3567-78. Some oncolytic viruses have a protein expression function added by genetic modification and may be allowed to express IL-7 and CCL19 described above instead of or in addition to such a protein.

The anaerobe is not particularly limited as long as the anaerobe can express IL-7 and CCL19 by introducing the nucleic acid encoding IL-7 and the nucleic acid encoding CCL19 into its cell. An anaerobic gram-positive bacterium having the ability to accumulate to malignant tumor cells is preferred. Examples thereof can include a bacterium of the genus *Bifidobacterium* such as bifidus, a bacterium of the genus *Lactobacillus*, and a bacterium of the genus *Listeria*. The anaerobe is known to accumulate easily to malignant tumor cells because the anaerobe grows easily in an environment containing less oxygen.

The liposome is not particularly limited as long as the liposome can deliver the nucleic acid encoding IL-7 and the nucleic acid encoding CCL19 to tumor cells and is a lipid nanocapsule constituted by a phospholipid bilayer. The liposome can be obtained by use of a commercially available product or by synthesis according to a routine method.

The MSC is not particularly limited as long as the MSC can express IL-7 and CCL19 by introducing the nucleic acid encoding IL-7 and the nucleic acid encoding CCL19 into the cell, and has the ability to accumulate to malignant tumor cells.

The nanoparticle is not particularly limited as long as the nanoparticle has the ability to be able to deliver the nucleic acid encoding IL-7 and the nucleic acid encoding CCL19 to tumor cells, and is in a particle form of nanometer order, preferably 5 to 800 nm in diameter. Examples thereof can include a metal nanoparticle such as a gold nanoparticle, and a silica nanoparticle. The nanoparticle can be obtained by use of a commercially available product or by synthesis according to a routine method.

The phrase "nucleic acid delivery vehicle has the ability to accumulate to malignant tumor cells" means that the nucleic acid delivery vehicle has the ability to accumulate specifically to malignant tumor cells. Specific examples of such ability can include a) the ability of the nucleic acid delivery vehicle to accumulate to malignant tumor cells by the action of a substance that recognizes a cell surface molecule of the malignant tumor cells, the substance being carried by the nucleic acid delivery vehicle, and b) the ability of the nucleic acid delivery vehicle to accumulate to malignant tumor cells by an EPR (enhanced permeability and retention) effect which exploits a vent of several hundreds of nm that is opened in the vascular wall of a tumor tissue and is wider by single digit or more than that of the vascular vessel of a normal tissue. Examples of the substance that recognizes a cell surface molecule of malignant tumor cells, carried by the nucleic acid delivery vehicle can include a chimeric antigen receptor (CAR) and a T-cell receptor (TCR). A receptor described in patent documents 2 and 3 can be used as the CAR or the TCR. Thus, examples of the nucleic acid delivery vehicle having the ability to accumulate to malignant tumor cells can include a CAR-expressing immune cell and a TCR-expressing immune cell. The chimeric antigen receptor (CAR) is an artificial chimeric protein in which single chain Fv (scFv) that recognizes a cell surface antigen of cancer cells is fused with a signal transduction region that induces the activation of T-cells.

The "ability to proliferate specifically in malignant tumor cells" means the ability to rarely proliferate in infected normal cells, but proliferate in infected malignant tumor cells. Examples thereof can include the ability of an oncolytic virus to proliferate specifically in malignant tumor cells. Thus, examples of the nucleic acid delivery vehicle having the ability to proliferate specifically in malignant tumor cells can include an oncolytic virus.

The "cytotoxicity against malignant tumor cells" means the ability to lyse or kill malignant tumor cells by damaging the malignant tumor cells. Malignant tumor cells are lysed or killed so that a malignant tumor antigen in the malignant tumor cells is released to the surroundings of the lysed or killed cells.

The "cell surface molecule that recognizes a malignant tumor antigen" can be any cell surface molecule that recognizes a malignant tumor antigen on the cell surface of malignant tumor. Examples thereof can include a chimeric antigen receptor (CAR) and a T-cell receptor (TCR). A receptor described in patent documents 2 and 3 can be used as the CAR or the TCR. Thus, examples of the immune cell having the cell surface molecule that recognizes a malignant tumor antigen can include a CAR-expressing immune cell and a TCR-expressing immune cell.

The malignant tumor antigen means a substance, such as a protein or a glycolipid, which is expressed more highly in malignant tumor cells than in normal cells or specifically expressed in malignant tumor cells. Examples of such a malignant tumor antigen can include an epitope peptide of a tumor-associated antigen, a cancer-testis antigen, an angiogenesis-associated antigen, or an antigen newly generated in malignant tumor by gene mutation (neoantigen) and can specifically include a protein such as WT1, MART-1, NY-ESO-1, MAGE-A1, MAGE-A3, MAGE-A4, Glypican-3, KIF20A, Survivin, AFP-1, gp100, MUC1, PAP-10, PAP-5, TRP2-1, SART-1, VEGFR1, VEGFR2, NEIL3, MPHOSPH1, DEPDC1, FOXM1, CDH3, TTK, TOMM34, URLC10, KOC1, UBE2T, TOPK, ECT2, MESOTHELIN, NKG2D, PIA, 5T4, B7-H6, BCMA, CD123, CD133, CD138, CD171, CD19, CD20, CD22, CD23, CD30, CD33, CD38, CD44, CEA, cMet, CS1, EGFR, EGFRvIII, EphA2, ErbB2, FAP, FR-α, HER2, IL13Ra2, MUC1, MUC16, NKG2D, PSCA, PSMA, ROR1, TARP, DLL3, PRSS21, Claudin18.2, Claudin18, CAIX, L1-CAM, FAP-α, CTAG1B, and FR-α, and a glycolipid such as GD2 and GM2.

The phrase "comprising a nucleic acid delivery vehicle, a nucleic acid encoding IL-7, and a nucleic acid encoding CCL19" also includes an aspect in which the nucleic acid encoding IL-7 and the nucleic acid encoding CCL19 are contained in the nucleic acid delivery vehicle. When the nucleic acid delivery vehicle is, for example, an immune cell, the nucleic acid encoding IL-7 and the nucleic acid encoding CCL19 can be contained in the immune cell. The immune cell may contain the nucleic acid encoding IL-7 and the nucleic acid encoding CCL19 in a state integrated into the genome or in a state not integrated into the genome (e.g., in an episomal state).

When the nucleic acid delivery vehicle is an immune cell, the present enhancer or inducer or the present malignant tumor recurrence inhibitor can be prepared by introducing the nucleic acid encoding IL-7 and the nucleic acid encoding CCL19 to the immune cell, i.e., introducing a foreign nucleic acid encoding IL-7 and nucleic acid encoding CCL19 (preferably a foreign nucleic acid encoding IL-7 and nucleic acid encoding CCL19 operably linked to downstream of a promoter) to the immune cell. The introduction method can be any method for introducing DNA to an immune cell. Examples thereof can include a method such as an electroporation method (Cytotechnology, 3, 133 (1990)), a calcium phosphate method (Japanese unexamined Patent Application Publication No. 2-227075), a lipofection method (Proc. Natl. Acad. Sci. U.S.A., 84, 7413 (1987)), and a viral infection method. Examples of the viral infection method can include a method which involves transfecting packaging cells such as GP2-293 cells (manufactured by Takara Bio Inc.), Plat-GP cells (manufactured by Cosmo Bio Co., Ltd.), PG13 cells (ATCC CRL-10686), or PA317 cells (ATCC CRL-9078) with a vector comprising a nucleic acid to be introduced and a packaging plasmid to prepare a recombinant virus, and infecting T-cells with the recombinant virus (patent document 2).

When the nucleic acid delivery vehicle is a virus, a "virus that has the nucleic acid encoding IL-7 and the nucleic acid encoding CCL19 and expresses IL-7 and CCL19" can be prepared by introducing the nucleic acid encoding IL-7 and the nucleic acid encoding CCL19 to the virus, i.e., introducing a foreign nucleic acid encoding IL-7 and nucleic acid encoding CCL19 (preferably a foreign nucleic acid encoding IL-7 and nucleic acid encoding CCL19 operably linked to downstream of a promoter) to the virus. The virus thus prepared can be used as the present enhancer or inducer or the present malignant tumor recurrence inhibitor.

Likewise, when the nucleic acid delivery vehicle is an anaerobe, a liposome, or a mesenchymal stem cell (MSC), a "anaerobe, liposome, or mesenchymal stem cell (MSC) that has the nucleic acid encoding IL-7 and the nucleic acid encoding CCL19 and expresses IL-7 and CCL19" can be prepared by introducing the nucleic acid encoding IL-7 and the nucleic acid encoding CCL19 to the anaerobe, the liposome, or the mesenchymal stem cell (MSC), i.e., introducing a foreign nucleic acid encoding IL-7 and nucleic acid encoding CCL19 (preferably a foreign nucleic acid encoding IL-7 and nucleic acid encoding CCL19 operably linked to downstream of a promoter) to the anaerobe, the liposome, or the mesenchymal stem cell (MSC). The anaerobe, the liposome, or the mesenchymal stem cell (MSC) thus prepared can be used as the present enhancer or inducer or the present malignant tumor recurrence inhibitor. Also, the "virus that has the nucleic acid encoding IL-7 and the nucleic acid encoding CCL19 and expresses IL-7 and CCL19", the "anaerobe that has the nucleic acid encoding IL-7 and the nucleic acid encoding CCL19 and expresses IL-7 and CCL19", the "liposome that has the nucleic acid encoding IL-7 and the nucleic acid encoding CCL19 and expresses IL-7 and CCL19", or the "mesenchymal stem cell (MSC) that has the nucleic acid encoding IL-7 and the nucleic acid encoding CCL19 and expresses IL-7 and CCL19" may be used as a malignant tumor proliferation inhibitor.

Another method for introducing the nucleic acid encoding IL-7 and the nucleic acid encoding CCL19 to the immune cell may be a method which involves integrating the nucleic acid encoding IL-7 and the nucleic acid encoding CCL19 into the genome of the immune cell by use of a gene editing technique known in the art such that these nucleic acids are expressible under the control of a suitable promoter. Examples of the gene editing technique known in the art can include a technique using an endonuclease such as zinc finger nuclease, TALEN (transcription activator-like effector nuclease), or CRISPR (clustered regularly interspaced short palindromic repeat)-Cas system.

In the case of preparing an "immune cell that contains the nucleic acid encoding IL-7 and the nucleic acid encoding CCL19 and has CAR as the cell surface molecule that recognizes a malignant tumor antigen, i.e., an immune cell that contains nucleic acids encoding CAR, IL-7, and CCL19 and expresses CAR, IL-7, and CCL19" as the present enhancer or inducer or the present malignant tumor recurrence inhibitor, this immune cell can be prepared by any of the following methods:

(1) a method of simultaneously or sequentially introducing two types of vectors, an IL-7-CCL19 expression vector containing the nucleic acid encoding IL-7 and the nucleic acid encoding CCL19, and a CAR expression vector containing the nucleic acid encoding CAR, to the immune cell;
(2) a method of simultaneously or sequentially introducing two types of vectors, a CAR-IL-7 expression vector containing the nucleic acid encoding CAR and the nucleic acid encoding IL-7, and a CAR-CCL19 expression vector containing the nucleic acid encoding CAR and the nucleic acid encoding CCL19, to the immune cell;
(3) a method of simultaneously or sequentially introducing two types of vectors, a CAR-IL-7 expression vector containing the nucleic acid encoding CAR and the nucleic acid encoding IL-7, and an IL-7-CCL19 expression vector containing the nucleic acid encoding IL-7 and the nucleic acid encoding CCL19, to the immune cell;
(4) a method of simultaneously or sequentially introducing two types of vectors, a CAR-CCL19 expression vector containing the nucleic acid encoding CAR and the nucleic acid encoding CCL19, and an IL-7-CCL19 expression vector containing the nucleic acid encoding IL-7 and the nucleic acid encoding CCL19, to the immune cell;
(5) a method of simultaneously or sequentially introducing two types of vectors, a CAR-IL-7 expression vector containing the nucleic acid encoding CAR and the nucleic acid encoding IL-7, and a CCL19 expression vector containing the nucleic acid encoding CCL19, to the immune cell;
(6) a method of simultaneously or sequentially introducing two types of vectors, a CAR-CCL19 expression vector containing the nucleic acid encoding CAR and the nucleic acid encoding CCL19, and an IL-7 expression vector containing the nucleic acid encoding IL-7, to the immune cell; and
(7) a method of simultaneously or sequentially introducing three types of vectors, a CAR expression vector containing the nucleic acid encoding CAR, an IL-7 expression vector containing the nucleic acid encoding IL-7, and a CCL19 expression vector containing the nucleic acid encoding CCL19, to the immune cell.

Likewise, in the case of preparing an "immune cell that contains the nucleic acid encoding IL-7 and the nucleic acid encoding CCL19 and has TCR as the cell surface molecule that recognizes a malignant tumor antigen, i.e., an immune cell that contains nucleic acids encoding TCR, IL-7, and CCL19 and expresses TCR, IL-7, and CCL19" as the present enhancer or inducer or the present malignant tumor recurrence inhibitor, this immune cell can be prepared by any of the following methods:

(1) a method of simultaneously or sequentially introducing two types of vectors, an IL-7-CCL19 expression vector containing the nucleic acid encoding IL-7 and the nucleic acid encoding CCL19, and a TCR expression vector containing the nucleic acid encoding TCR, to the immune cell;

(2) a method of simultaneously or sequentially introducing two types of vectors, a TCR-IL-7 expression vector containing the nucleic acid encoding TCR and the nucleic acid encoding IL-7, and a TCR-CCL19 expression vector containing the nucleic acid encoding TCR and the nucleic acid encoding CCL19, to the immune cell;

(3) a method of simultaneously or sequentially introducing two types of vectors, a TCR-IL-7 expression vector containing the nucleic acid encoding TCR and the nucleic acid encoding IL-7, and an IL-7-CCL19 expression vector containing the nucleic acid encoding IL-7 and the nucleic acid encoding CCL19, to the immune cell;

(4) a method of simultaneously or sequentially introducing two types of vectors, a TCR-CCL19 expression vector containing the nucleic acid encoding TCR and the nucleic acid encoding CCL19, and an IL-7-CCL19 expression vector containing the nucleic acid encoding IL-7 and the nucleic acid encoding CCL19, to the immune cell;

(5) a method of simultaneously or sequentially introducing two types of vectors, a TCR-IL-7 expression vector containing the nucleic acid encoding TCR and the nucleic acid encoding IL-7, and a CCL19 expression vector containing the nucleic acid encoding CCL19, to the immune cell;

(6) a method of simultaneously or sequentially introducing two types of vectors, a TCR-CCL19 expression vector containing the nucleic acid encoding TCR and the nucleic acid encoding CCL19, and an IL-7 expression vector containing the nucleic acid encoding IL-7, to the immune cell; and (7) a method of simultaneously or sequentially introducing three types of vectors, a TCR expression vector containing the nucleic acid encoding TCR, an IL-7 expression vector containing the nucleic acid encoding IL-7, and a CCL19 expression vector containing the nucleic acid encoding CCL19, to the immune cell.

In the case of preparing the "immune cell expressing TCR, IL-7, and CCL19", an immune cell expressing TCR specific for the desired tumor antigen is prepared in advance, and the immune cell expressing TCR, IL-7, and CCL19 may be prepared by any of the following methods using the TCR-expressing immune cell:

(1) a method of introducing an IL-7-CCL19 expression vector containing the nucleic acid encoding IL-7 and the nucleic acid encoding CCL19 to the TCR-expressing immune cell; and (2) a method of simultaneously or sequentially introducing two types of vectors, an IL-7 expression vector containing the nucleic acid encoding IL-7, and a CCL19 expression vector containing the nucleic acid encoding CCL19, to the TCR-expressing immune cell.

In addition, an "immune cell expressing CAR, TCR, IL-7, and CCL19" may be prepared as the present enhancer or inducer or the present malignant tumor recurrence inhibitor. Specific examples of the method therefor can include a preparation method of further allowing all or any of the vectors described in the "case of preparing an immune cell expressing CAR, IL-7, and CCL19" to contain the nucleic acid encoding TCR such that TCR is also expressed, a preparation method of further allowing all or any of the vectors described in the "case of preparing an immune cell expressing TCR, IL-7, and CCL19" to contain the nucleic acid encoding CAR such that CAR is also expressed, and a preparation method of introducing the vectors described in the "case of preparing an immune cell expressing CAR, IL-7, and CCL19" to the "TCR-expressing immune cell".

Furthermore, when the immune cell in the present enhancer or inducer or the present malignant tumor recurrence inhibitor has CAR, an "immune cell expressing a plurality of, preferably two types of CARs that recognize different malignant tumor antigens" may be prepared. Specific examples of the method therefor can include a preparation method of allowing the vectors described in the "case of preparing an immune cell expressing CAR, IL-7, and CCL19" to contain nucleic acids encoding a plurality of, preferably two types of CARs that recognize different malignant tumor antigens such that the plurality of, preferably the two types of CARs are expressed. Particularly, for example, a malignant tumor antigen X-recognizing CAR-IL-7 expression vector containing the nucleic acid encoding CAR that recognizes malignant tumor antigen X and the nucleic acid encoding IL-7, and a malignant tumor antigen Y-recognizing CAR-CCL19 expression vector containing the nucleic acid encoding CAR that recognizes malignant tumor antigen Y and the nucleic acid encoding CCL19 are prepared and introduced to the immune cell. The resulting immune cell can have higher tumor specificity because IL-7 and CCL19 are secreted to the surroundings of cells having the malignant tumor antigens X and Y.

When the nucleic acid delivery vehicle is an immune cell, a virus, an anaerobe, or a mesenchymal stem cell, a culture product that is obtained by culturing the immune cell, the virus, the anaerobe, or the mesenchymal stem cell and contains the immune cells may be used.

The "malignant tumor recurrence" for the malignant tumor recurrence inhibitor means the occurrence of malignant tumor again after malignant tumor treatment by general chemotherapy, radiotherapy, or surgical therapy, etc. The malignant tumor recurrence is preferably recurrence ascribable to malignant tumor cells having resistance to the ability of the nucleic acid delivery vehicle to accumulate to malignant tumor cells, or the ability of the nucleic acid delivery vehicle to proliferate specifically in malignant tumor cells.

In this context, examples of the "recurrence ascribable to malignant tumor cells having resistance to the ability to accumulate to malignant tumor cells" can include the case in which the nucleic acid delivery vehicle is an immune cell having a cell surface molecule that recognizes a malignant tumor antigen, and the malignant tumor recurrence is malignant tumor recurrence ascribable to malignant tumor cells having no malignant tumor antigen that is specifically recognized by the cell surface molecule, or having lost the malignant tumor antigen that is specifically recognized by the cell surface molecule. Examples of the "recurrence ascribable to malignant tumor cells having resistance to the ability of the nucleic acid delivery vehicle to proliferate specifically in malignant tumor cells" can include tumor recurrence ascribable to malignant tumor cells having no sensitivity to infection with an oncolytic virus for malignant tumor, or having lost the sensitivity to infection with an oncolytic virus for malignant tumor. The "recurrence ascribable to malignant tumor cells having resistance to the ability to accumulate to malignant tumor cells" can be confirmed, for example, by examining a malignant tumor antigen in malignant tumor cells of a tissue that has undergone recurrence.

The malignant tumor recurrence inhibitor can be used for administration to a subject having malignant tumor treated by immunotherapy. The malignant tumor recurrence inhibitor may be used for administration to a subject having malignant tumor treated by immunotherapy, day 100 or later after the treatment by immunotherapy for the purpose of inhibiting recurrence for a long period.

The present enhancer or inducer or the present malignant tumor recurrence inhibitor may contain a pharmaceutically acceptable additive. The present enhancer or inducer or the present malignant tumor recurrence inhibitor may further contain an instruction for its use. The present enhancer or inducer or the present malignant tumor recurrence inhibitor may be prepared into a pharmaceutical composition by containing a pharmaceutically acceptable additive. Hereinafter, the "pharmaceutical composition containing the present enhancer and a pharmaceutically acceptable additive", the "pharmaceutical composition containing the present inducer and a pharmaceutically acceptable additive", and the "pharmaceutical composition containing the present malignant tumor recurrence inhibitor and a pharmaceutically acceptable additive" are also collectively referred to as the "present pharmaceutical composition". Examples of the additive can include saline, buffered saline, a culture medium for cell culture, dextrose, injectable water, glycerol, ethanol and a combination thereof, a stabilizer, a solubilizer, a surfactant, a buffer, an antiseptic, a tonicity agent, a filler, and a lubricant.

The present enhancer or inducer, the present malignant tumor recurrence inhibitor, or the present pharmaceutical composition can be administered to a subject in need of treatment of malignant tumor or inhibition of its recurrence by use of a method known to those skilled in the art. Examples of the administration method can include intravenous, intratumoral, intradermal, subcutaneous, intramuscular, intraperitoneal, intraarterial, intramedullary, intracardiac, intraarticular, intrasynovial, intracranial, intraspinal, and subarachnoidal (spinal fluid) injection.

Examples of the method for administering the present enhancer or inducer, the present malignant tumor recurrence inhibitor, or the present pharmaceutical composition can include administration independently performed four times, three times, twice or once a day, every 2 days, every 3 days, every 4 days, every 5 days, every 6 days, once a week, every 8 days, every 9 days, every 10 days, twice a week, once a month or twice a month.

The dose of the present enhancer or inducer, the present malignant tumor recurrence inhibitor, or the present pharmaceutical composition can be appropriately determined according to the age, sex, health, and body weight, etc. of a subject. When the nucleic acid delivery vehicle is, for example, an immune cell, examples thereof can include $1\times10^3$ to $1\times10^9$ cells, preferably $1\times10^4$ to $1\times10^8$ cells, more preferably $1\times10^5$ to $1\times10^7$ cells, per kg of body weight to a human adult. When the nucleic acid delivery vehicle is an oncolytic virus, examples thereof can include approximately $10^2$ to $10^{10}$ plaque-forming units (PFU), preferably $10^5$ to $10^6$ plaque-forming units (PFU), per dosage to a human adult.

In the present specification, the malignant tumor may be malignant solid tumor or malignant blood tumor. Examples thereof can include a cancer such as glioma, melanoma, malignant mesothelioma, adenocarcinoma, squamous cell carcinoma, adenosquamous carcinoma, anaplastic cancer, large-cell cancer, small-cell cancer, skin cancer, thyroid gland cancer, breast cancer, prostate cancer, urinary bladder cancer, vaginal cancer, head and neck cancer, neck cancer, uterine cancer, liver cancer, kidney cancer, pancreatic cancer, spleen cancer, lung cancer, trachea cancer, bronchial cancer, large intestine cancer, colon cancer, small intestine cancer, stomach cancer, esophageal cancer, biliary tract cancer, gallbladder cancer, testis cancer, ovary cancer, and brain tumor, a cancer of a bone tissue, a cartilage tissue, an adipose tissue, a muscle tissue, a vascular tissue, or a hematopoietic tissues as well as a sarcoma such as chondrosarcoma, Ewing's sarcoma, malignant hemangioendothelioma, malignant schwannoma, osteosarcoma, and soft tissue sarcoma, a blastoma such as hepatoblastoma, medulloblastoma, nephroblastoma, neuroblastoma, pancreatoblastoma, pleuropulmonary blastoma, and retinoblastoma, germ cell tumor, lymphoma, leukemia, and myeloma.

The present enhancer or inducer, the present malignant tumor recurrence inhibitor, or the present pharmaceutical composition can be used in combination with an additional antitumor agent. Also, a method using the present enhancer or inducer, the present malignant tumor recurrence inhibitor, or the present pharmaceutical composition may be combined with a cancer treatment method using radiation. Examples of the additional antitumor agent can include an alkylating drug such as cyclophosphamide, bendamustine, ifosfamide, and dacarbazine, an antimetabolic drug such as pentostatin, fludarabine, cladribine, methotrexate, 5-fluorouracil, 6-mercaptopurine, and enocitabine, a molecular targeting drug such as rituximab, cetuximab, and trastuzumab, a kinase inhibitor such as imatinib, gefitinib, erlotinib, afatinib, dasatinib, sunitinib, and trametinib, a proteasome inhibitor such as bortezomib, a calcineurin inhibitory drug such as cyclosporin and tacrolimus, an anticancer antibiotic such as idarubicin and doxorubicin-mitomycin C, a vegetable alkaloid such as irinotecan and etoposide, a platinum-containing drug such as cisplatin, oxaliplatin, and carboplatin, a hormone therapeutic such as tamoxifen and bicalutamide, and an immune-regulatory drug such as interferon, nivolumab, and pembrolizumab.

Examples of the method using the present enhancer or inducer, the present malignant tumor recurrence inhibitor, or the present pharmaceutical composition in combination with the additional antitumor agent can include a method using the additional antitumor agent and then using the present enhancer or inducer, the present malignant tumor recurrence inhibitor, or the present pharmaceutical composition, a method concurrently using the present enhancer or inducer, the present malignant tumor recurrence inhibitor, or the present pharmaceutical composition and the additional antitumor agent, and a method using the present enhancer or inducer, the present malignant tumor recurrence inhibitor, or the present pharmaceutical composition and then using the additional antitumor agent. In the case of using the present enhancer or inducer, the present malignant tumor recurrence inhibitor, or the present pharmaceutical composition and the additional antitumor agent in combination, a therapeutic effect on a cancer is further improved while their respective adverse reactions can be reduced by decreasing their respective frequencies of administration or doses.

References such as academic documents and patent applications cited herein are incorporated herein by reference in their entirety to the same extent as each specifically described.

EXAMPLES

Hereinafter, the present invention will be more specifically described with reference to Examples. However, the technical scope of the present invention is not limited by these examples.

(Preparation of Anti-Human CD20 CAR-IL-7/CCL19-Expressing T-Cells and Anti-Human CD20 CAR-Expressing T-Cells)

The "T-cells expressing anti-human CD20 CAR, mouse IL-7, and mouse CCL19 (anti-human CD20 CAR-IL-7/CCL19-expressing T-cells; also referred to as "7×19" in the following Examples or drawings)" and the "anti-human CD20 CAR-expressing T-cells; also referred to "Conn." in the following Examples or drawings)" used in Examples mentioned later were prepared in accordance with the methods described in patent document 3 and the article of Tamada et al. (Nature Biotechnology doi: 10.1038/nbt.4086). Hereinafter, the preparation method will be briefly described. The "T-cells expressing anti-human CD20 CAR, mouse IL-7, and mouse CCL19" are T-cells having anti-human CD20 CAR as the cell surface molecule that recognizes a malignant tumor cell antigen, and comprises the nucleic acid encoding IL-7 and the nucleic acid encoding CCL19.

For the anti-human CD20 CAR-IL-7/CCL19-expressing T-cells, first, an anti-human CD20 CAR-IL-7-CCL19 expression pMSGV vector containing the nucleic acid encoding anti-human CD20 CAR, the nucleic acid encoding mouse IL-7, and the nucleic acid encoding mouse CCL19 was prepared in advance. Subsequently, the vector was introduced using retrovirus to mouse T-cells separated from the spleens and lymph nodes of CD90.1-positive (CD90.1$^+$) and CD90.2-negative (CD90.2$^-$) congenic mice (manufactured by The Jackson Laboratory) using Pan T Cell Isolation Kit II (manufactured by Miltenyi Biotec) to prepare the anti-human CD20 CAR-IL-7/CCL19-expressing T-cells. Meanwhile, the T-cells expressing anti-human CD20 CAR (anti-human CD20 CAR-expressing T-cells) were prepared by preparing an anti-human 20 CAR expression pMSGV vector in advance, and introducing the vector to the separated mouse T-cells using retrovirus. The separated mouse T-cells without gene introduction (non-transduced T cells) are also referred to as "non-transduced" in the following Examples or drawings. In this context, a pMSGV vector was used as the retrovirus vector for introducing the nucleic acid encoding anti-human CD20 CAR, the nucleic acid encoding IL-7, and the nucleic acid encoding CCL19 to the mouse T-cells separated as described above. Hence, in the case of culturing the mouse T-cells thus harboring the nucleic acids for proliferation, some mouse T-cells contain the retrovirus vector in their cytoplasms, whereas the nucleic acid encoding anti-human CD20 CAR, the nucleic acid encoding IL-7, and the nucleic acid encoding CCL19 are integrated into the genomes of most of mouse T-cells. The mouse T-cells express anti-human CD20 CAR, IL-7, and CCL19 from a foreign recombinant construct when the nucleic acid encoding anti-human CD20 CAR, the nucleic acid encoding IL-7, and the nucleic acid encoding CCL19 are integrated in their genomes.

The culture of the T-cells employed RPMI-1640 culture medium supplemented with 10% fetal calf serum (FCS), 100 U/mL penicillin, 100 μg/mL streptomycin, 50 μM 2-mercaptoethanol, 25 mM HEPES, and 2 mM L-glutamine.

Example 1

<Localization of T-Cells>

Figure 1:
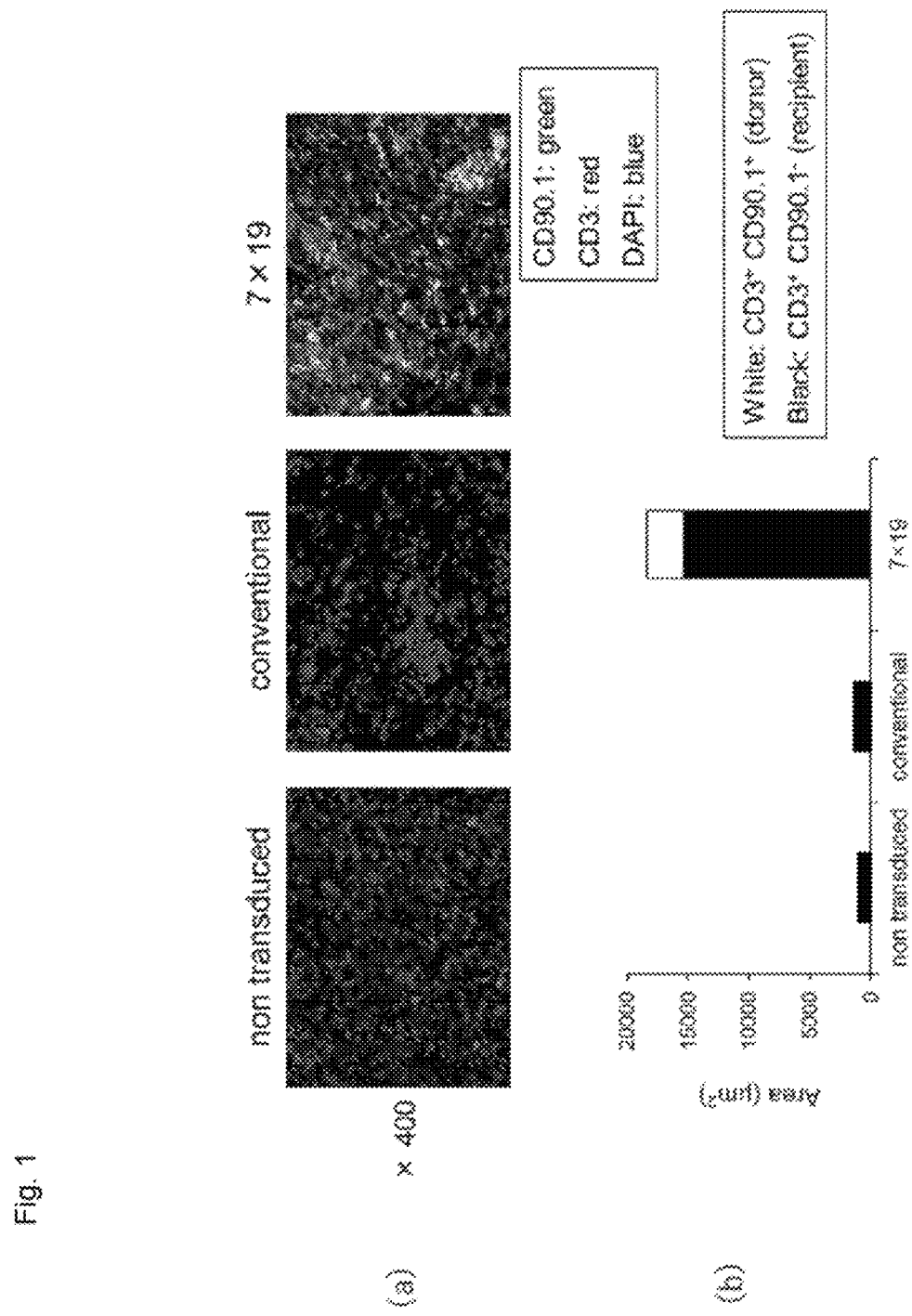
FIG. 1(a) is a diagram showing results about Example 1 in which the localization of T-cells in malignant tumor tissues were observed under a microscope by staining with a labeled antibody.
FIG. 1(b) is a graph showing the areas ($\mu m^2$) of administered donor T-cells and endogenous T-cells of a recipient by the image analysis processing of the results observed in FIG. 1(a).

In order to examine the antitumor effect of the CAR-IL-7/CCL19-expressing T-cells, whether host (recipient)-derived endogenous T-cells would infiltrate tumor tissues, as in administered donor T-cells, was examined. First, 2.5×10$^6$ cells of 3LL-hCD20 (mouse lung cancer-derived cells 3LL allowed to express human CD20 by gene recombination) were subcutaneously inoculated to each of 7- to 10-week-old C57BL/6 mice (manufactured by Japan SLC, Inc.) (day 0). Then, on day 7, an anticancer agent cyclophosphamide (CPA; 100 mg/kg) was intraperitoneally administered thereto. On day 10, 1×10$^6$ anti-human CD20 CAR-expressing T-cells or anti-human CD20 CAR-IL-7/CCL19-expressing T-cells produced from the CD90.1-positive (CD90.1$^+$) and CD90.2-negative (CD90.2$^-$) congenic mice, or separated mouse T-cells without gene introduction as described above were intravenously administered thereto. On day 19, tumor tissues were excised from the mice. A biotin-labeled anti-CD90.1 antibody (clone OX-7 manufactured by BioLegend, Inc.; binding to the donor T-cells) and an anti-CD3 antibody (clone 17A2; manufactured by Tonbo Biosciences Inc.; binding to both the donor T-cells and the recipient endogenous T-cells) were used in combination in primary staining, and Alexa Fluor 488-conjugated streptavidin (manufactured by Thermo Fisher Scientific, Inc.; green) and Alexa Fluor 647-conjugated anti-rat IgG2b (manufactured by Abcam PLC; red) were used in secondary staining. The nuclei were stained with DAPI (manufactured by Thermo Fisher Scientific Inc.; blue). Observation under a microscope was performed at ×400. The results are shown in FIG. 1(a). The secondary staining indicates cells bound with the biotin-labeled anti-CD90.1 antibody by green color, and cells bound with the anti-CD3 antibody by red color. Therefore, the anti-human CD20 CAR-IL-7/CCL19-expressing T-cells as the donor T-cells were yellow (green color+red color; CD90.1$^+$+CD3$^+$), and the recipient endogenous T-cells were red (CD90.1$^-$+CD3$^+$). In FIG. 1(a), the cells are indicated by grayscale.

FIG. 1(b) shows results of quantifying each positive region labeled in FIG. 1(a) using Hybrid Cell Count program (manufactured by Keyence Corp.). In FIG. 1(b), the filled column depicts the area of the recipient (host) endogenous T-cells (red in the right image of FIG. 1(a)), and the open column depicts the area of the administered donor T-cells (yellow in the right image of FIG. 1(a)). FIGS. 1(a) and 1(b) demonstrated that the administration of the anti-human CD20 CAR-IL-7/CCL19-expressing T-cells enhances the local accumulation of not only the administered T-cells but the recipient (host) endogenous T-cells to tumor, in other words, enhances the local accumulation of even the endogenous T-cells to tumor by locally secreting IL-7 and CCL19 to the tumor.

Example 2

<Involvement of T-Cells in Antitumor Effect>

Figure 2:
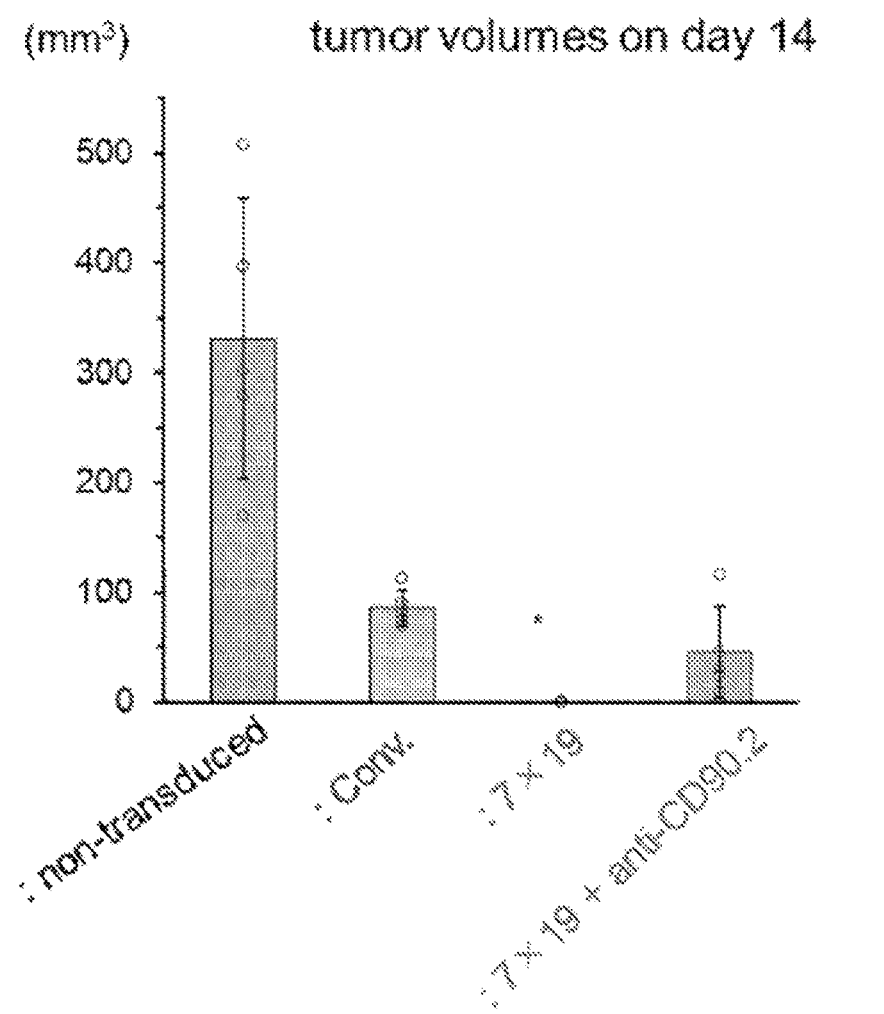
FIG. 2 is a graph of malignant tumor volumes ($mm^3$) examined on day 14 after administration when anti-human CD20 CAR-IL-7/CCL19-expressing T-cells (7×19) or an anti-CD90.2 antibody (anti-CD90.2) together with the T-cells were administered to mice in Example 2.

2.5×10$^6$ cells of 3LL-hCD20 were subcutaneously inoculated to each of C57BL/6 mice (day 0). Then, on day 3, 1×10$^6$ anti-human CD20 CAR-expressing T-cells (Conventional: Conv.) or anti-human CD20 CAR-IL-7/CCL19-expressing T-cells (7×19) produced from the CD90.1-positive (CD90.1$^+$) and CD90.2-negative (CD90.2$^-$) congenic mice were intravenously administered thereto. An anti-CD90.2 antibody (anti-CD90.2; prepared using a hybridoma purchased from ATCC by the present inventors), an antibody against CD90.2 (Thy1.2) expressed in the endogenous T-cells, was intraperitoneally administered twice a week from day 1. The first two doses were set to 1 mg/mouse, and the subsequent doses were set to 0.5 mg/mouse. FIG. 2 shows mean±SD of tumor volumes of day 14 in each group (n=5). o depicts the value of each mouse.

As shown in FIG. 2, the administration of the anti-human CD20 CAR-IL-7/CCL19-expressing T-cells suppressed the proliferation of malignant tumor, and the tumor disappeared because of a very high antitumor effect. However, the administration of the anti-CD90.2 antibody reduced the antitumor effect by approximately 50%. These results demonstrated that the recipient endogenous T-cells are also involved in the antitumor effect brought about by the anti-human CD20 CAR-IL-7/CCL19-expressing T-cells, in other words, not only the anti-human CD20 CAR-IL-7/CCL19-expressing T-cells themselves but the recipient endogenous T-cells are largely involved in the antitumor effect brought about by the anti-human CD20 CAR-IL-7/CCL19-expressing T-cells.

Example 3

<Memory Potential of Recipient Endogenous T-Cells>

The anti-human CD20 CAR-IL-7/CCL19-expressing T-cells were evaluated for acquirement of a memory function by donor CAR-T-cells and endogenous T-cells and increase in the number of cells having a memory function, using memory cell markers CD44 and CD62L.

$2.5 \times 10^6$ cells of 3LL-hCD20 were subcutaneously inoculated to each of C57BL/6 mice (day 0). Then, on day 3, $1 \times 10^6$ anti-human CD20 CAR-expressing T-cells (Conv.) or anti-human CD20 CAR-IL-7/CCL19-expressing T-cells (7×19) produced from the CD90.1-positive (CD90.1$^+$) and CD90.2-negative (CD90.2$^-$) congenic mice as described above were intravenously administered thereto. On day 28, spleen cells were collected and used in the next analysis.

The donor T-cells were identified as CD90.1-positive cells (CD90.1$^+$), and the recipient T-cells were identified as CD90.2-positive cells (CD90.2$^+$). The expression of the memory T-cell markers (CD44 and CD62L) and CAR in CD4-positive and CD8-positive T-cells was detected by flow cytometry. The numerical values of dot plots or histograms represent the proportion of cells in each gate. The results are shown in FIG. 3.

The acquirement of the function of memory potential, i.e., reactivity with stimulation, was examined by the production of IFN-γ. First, the spleen cells collected on day 28 were stimulated by coculture with 3LL-hCD20 or the parent line 3LL expressing no hCD20, treated with mitomycin C (manufactured by Kyowa Kirin Co., Ltd.) at 37° C. for 90 minutes. The production of IFN-γ was examined by intracellular cytokine staining. The results are shown in FIG. 4. The numerical values in the histograms of FIG. 4(a) represent the ratio of IFN-γ-positive cells to CD90.1-positive donor T-cells. FIG. 4(b) shows results of detecting IFN-γ-positive cells in CD90.2-positive and endogenous CD8-positive T-cells by flow cytometry. The numerical values of the dot plots represent the proportions of cells in 4 quadrants.

Figure 3:
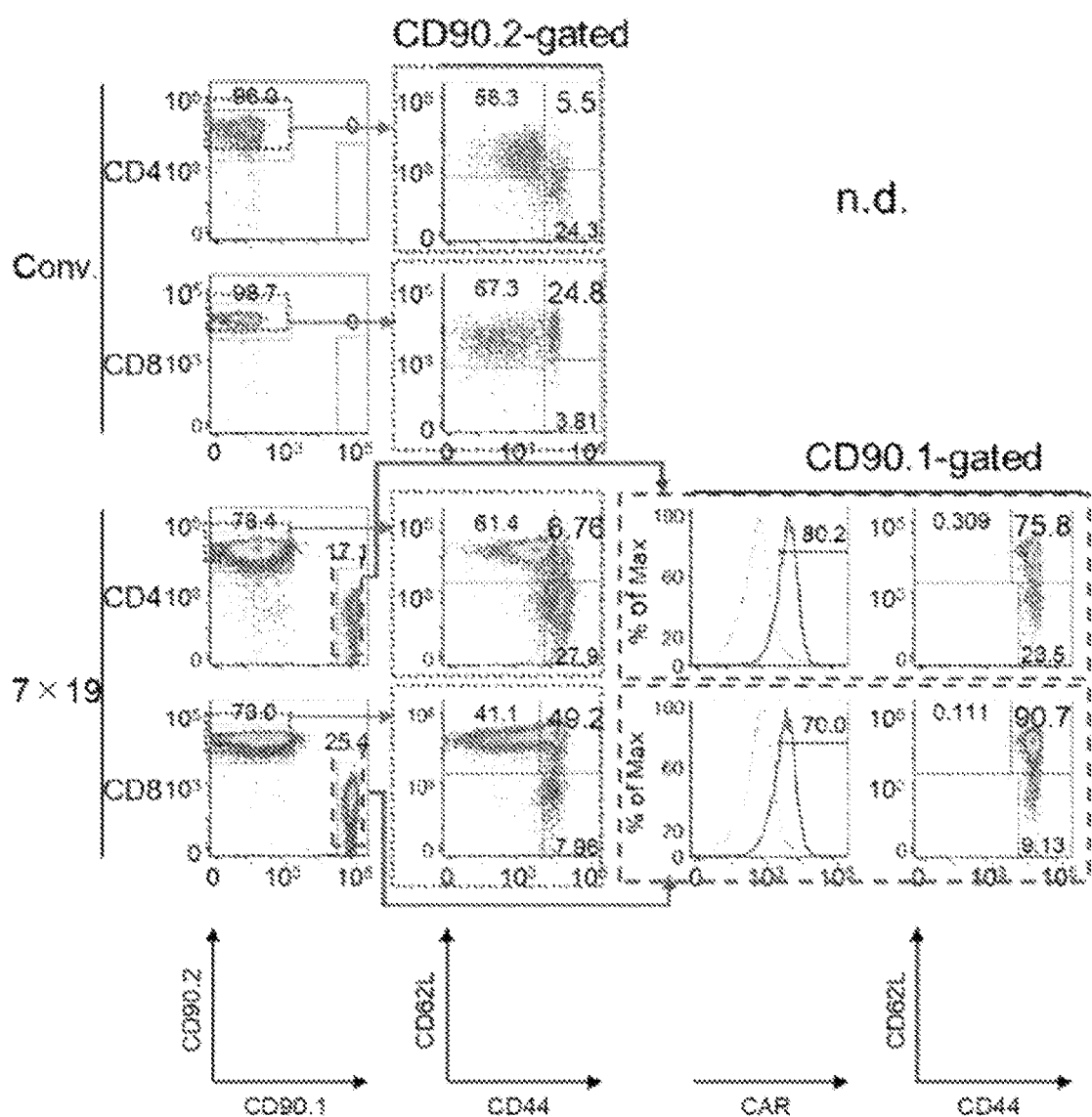
FIG. 3 is a graph showing results about Example 3 in which administered donor T-cells and endogenous T-cells of a recipient were examined for their memory potential.
Figure 5A:
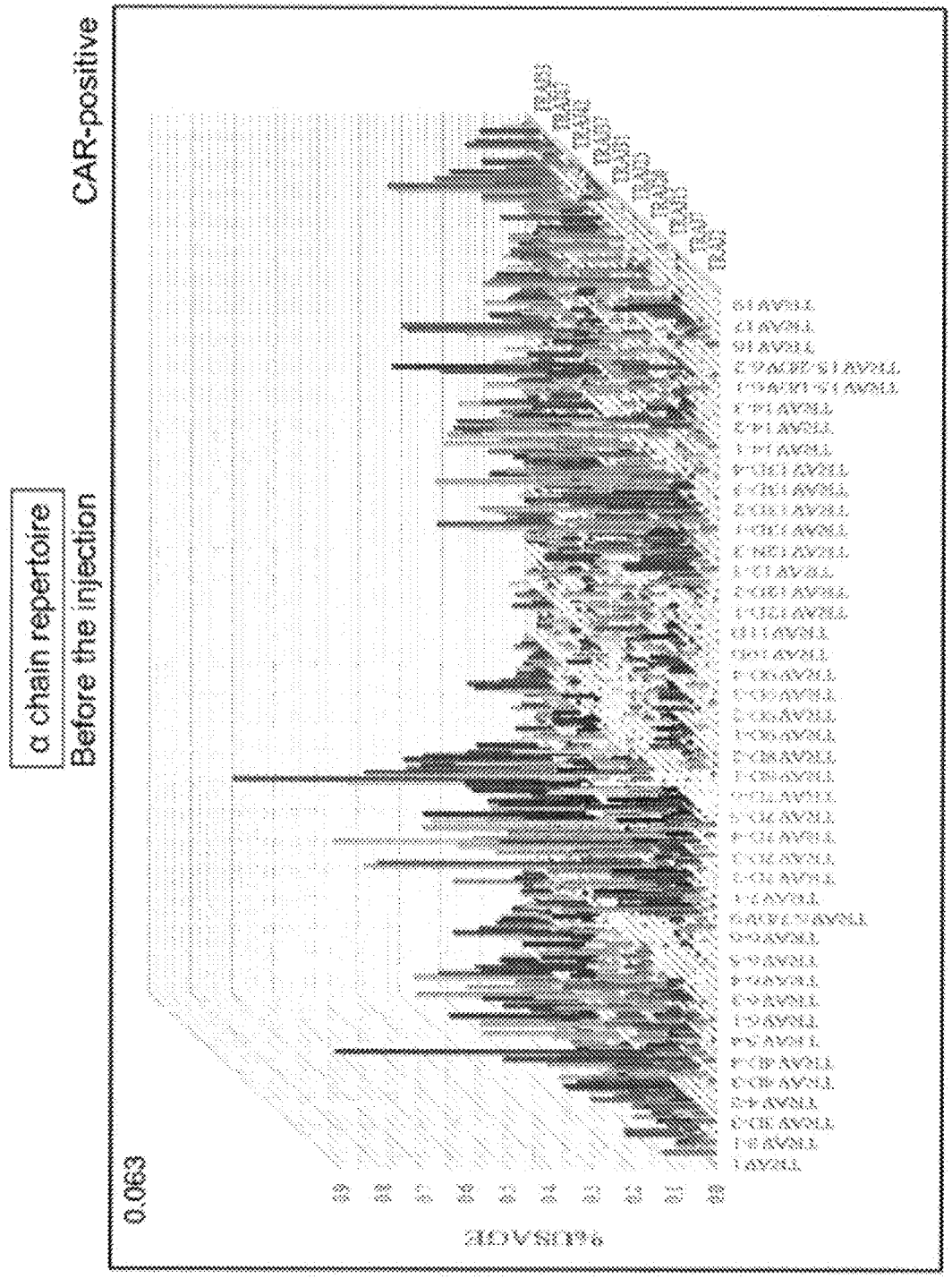
FIG. 5A is a graph showing results about Example 4 in which change in T-cell receptor (TCR) repertoire before treatment with CAR-IL-7/CCL19-expressing T-cells (α chain: before treatment, CAR-positive) was examined.
Figure 5B:
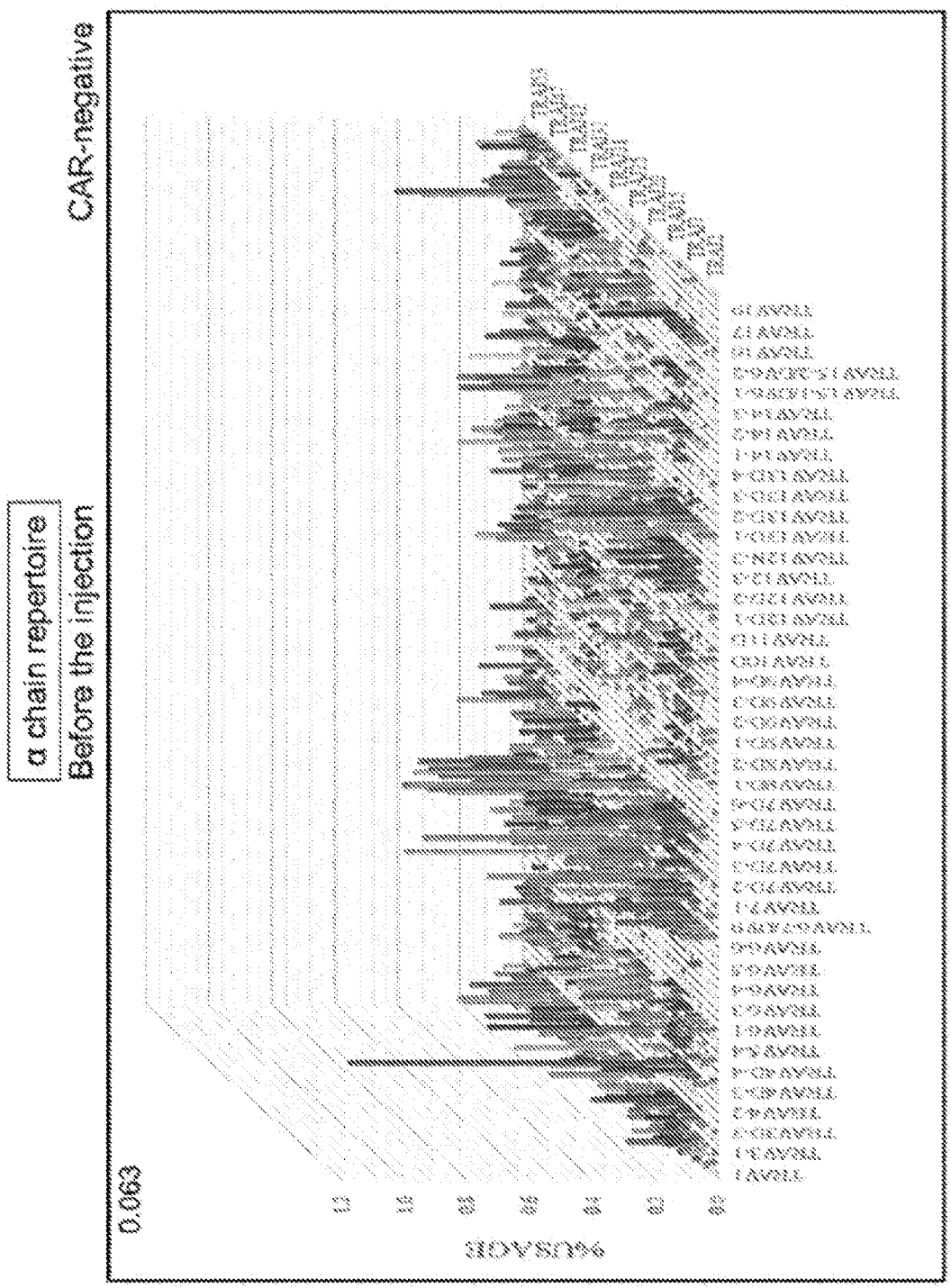
FIG. 5B is a graph showing results about Example 4 in which change in T-cell receptor (TCR) repertoire before treatment with CAR-IL-7/CCL19-expressing T-cells (α chain: before treatment, CAR-negative) was examined.
Figure 5D:
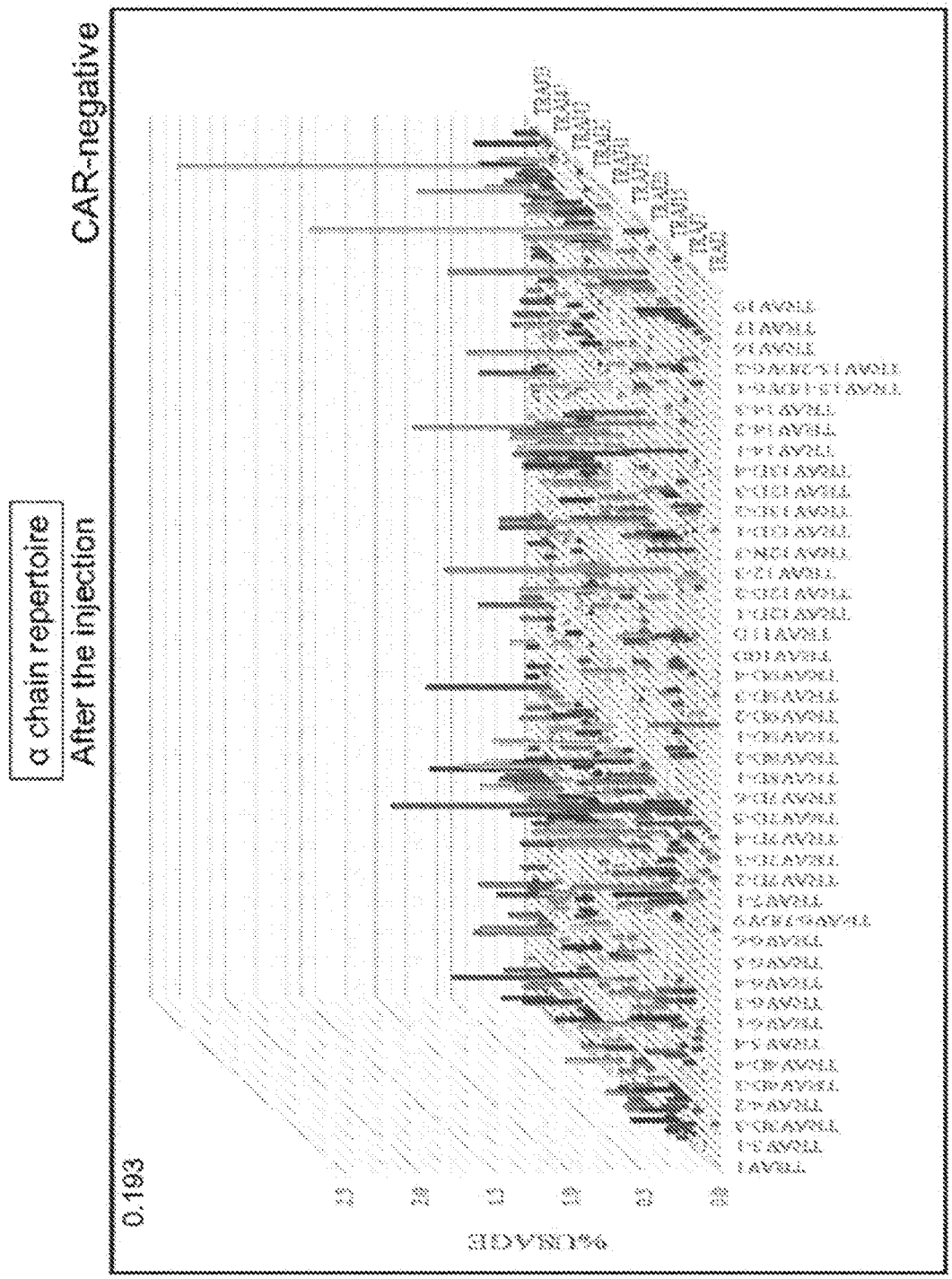
FIG. 5D is a graph showing results about Example 4 in which change in T-cell receptor (TCR) repertoire after treatment with CAR-IL-7/CCL19-expressing T-cells (α chain: after treatment, CAR-negative) was examined.
Figure 6A:
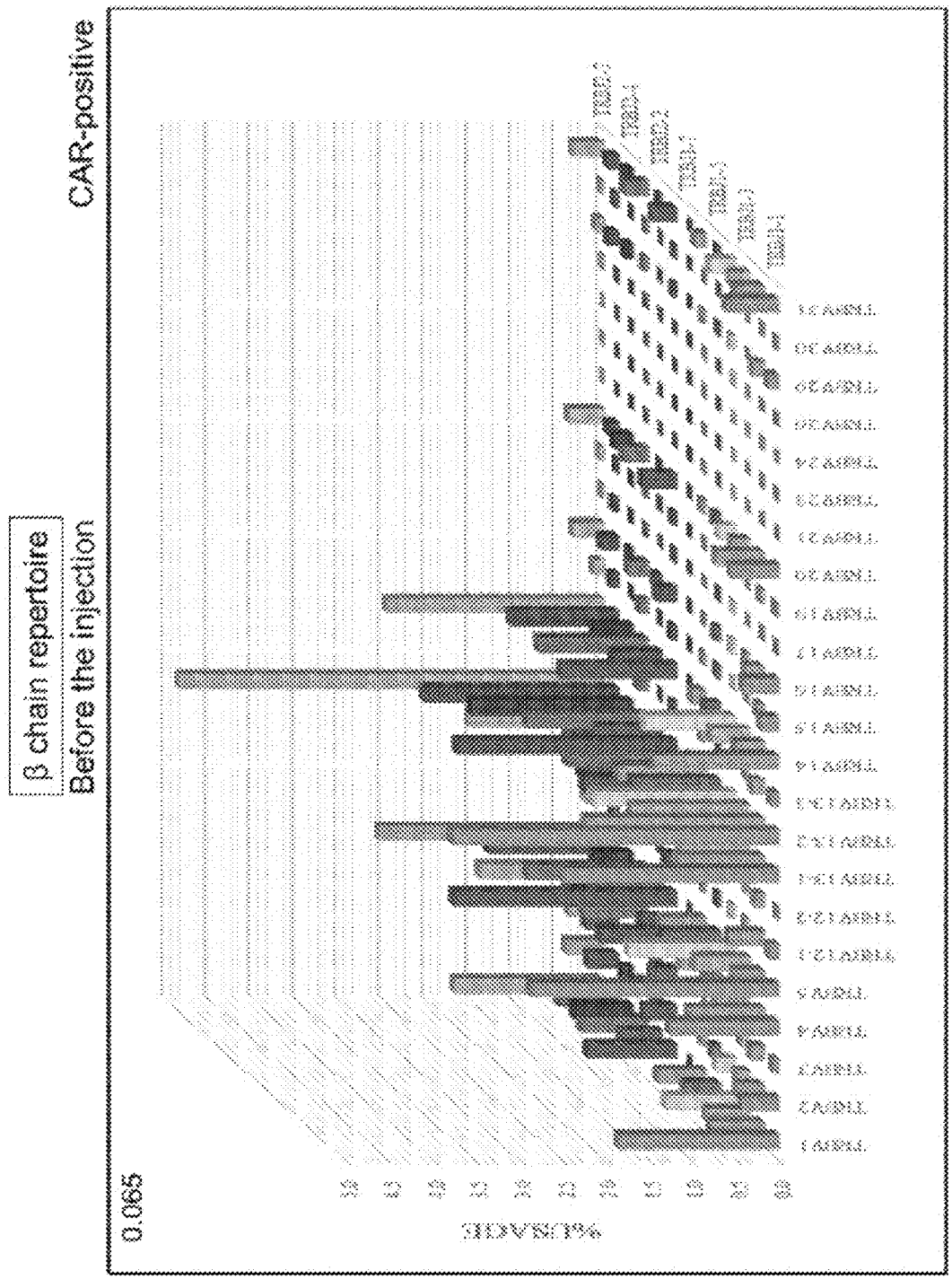
FIG. 6A is a graph showing results about Example 4 in which change in T-cell receptor (TCR) repertoire before treatment with CAR-IL-7/CCL19-expressing T-cells (β chain: before treatment, CAR-positive) was examined.
Figure 6B:
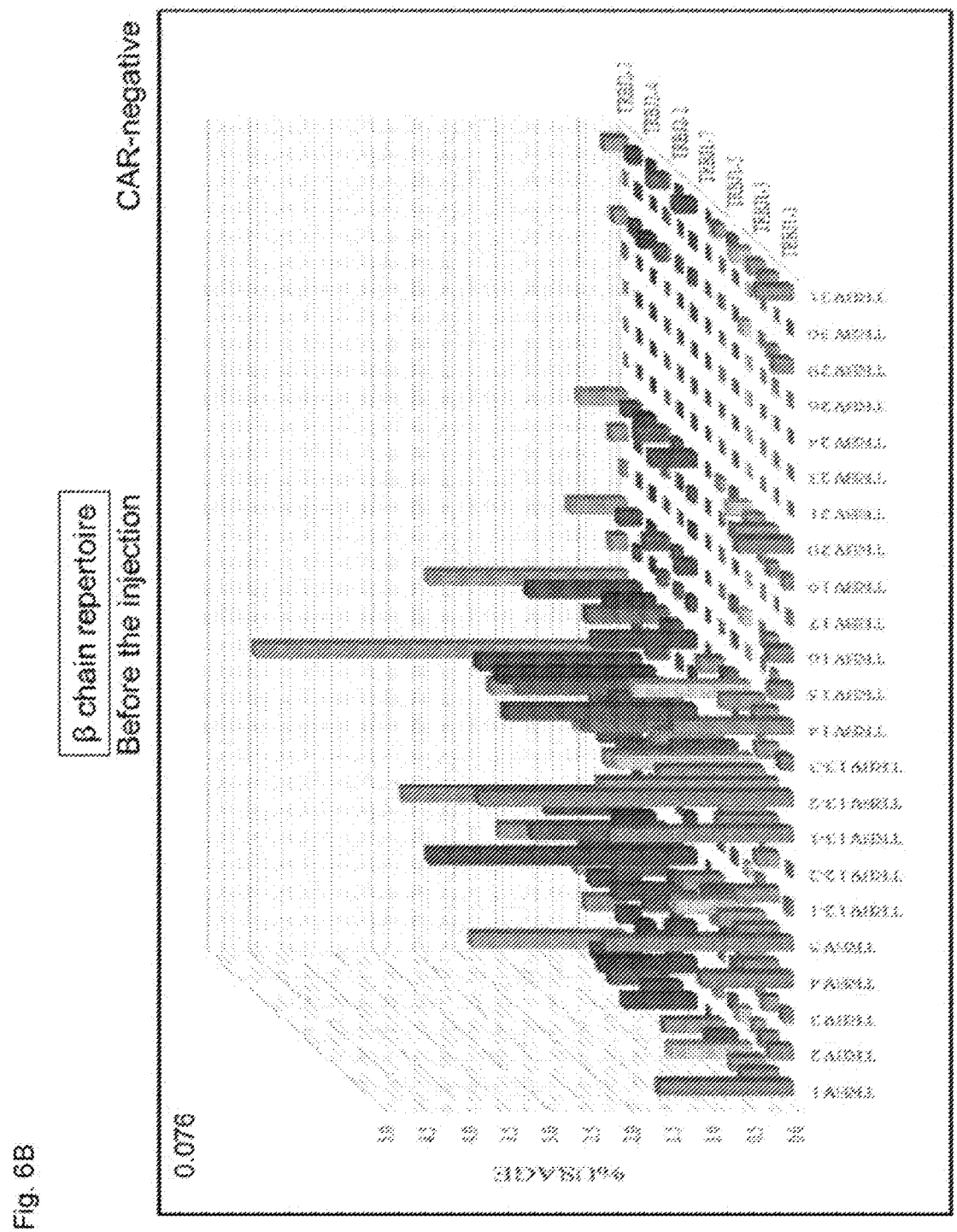
FIG. 6B is a graph showing results about Example 4 in which change in T-cell receptor (TCR) repertoire before treatment with CAR-IL-7/CCL19-expressing T-cells (β chain: before treatment, CAR-negative) was examined.
Figure 6C:
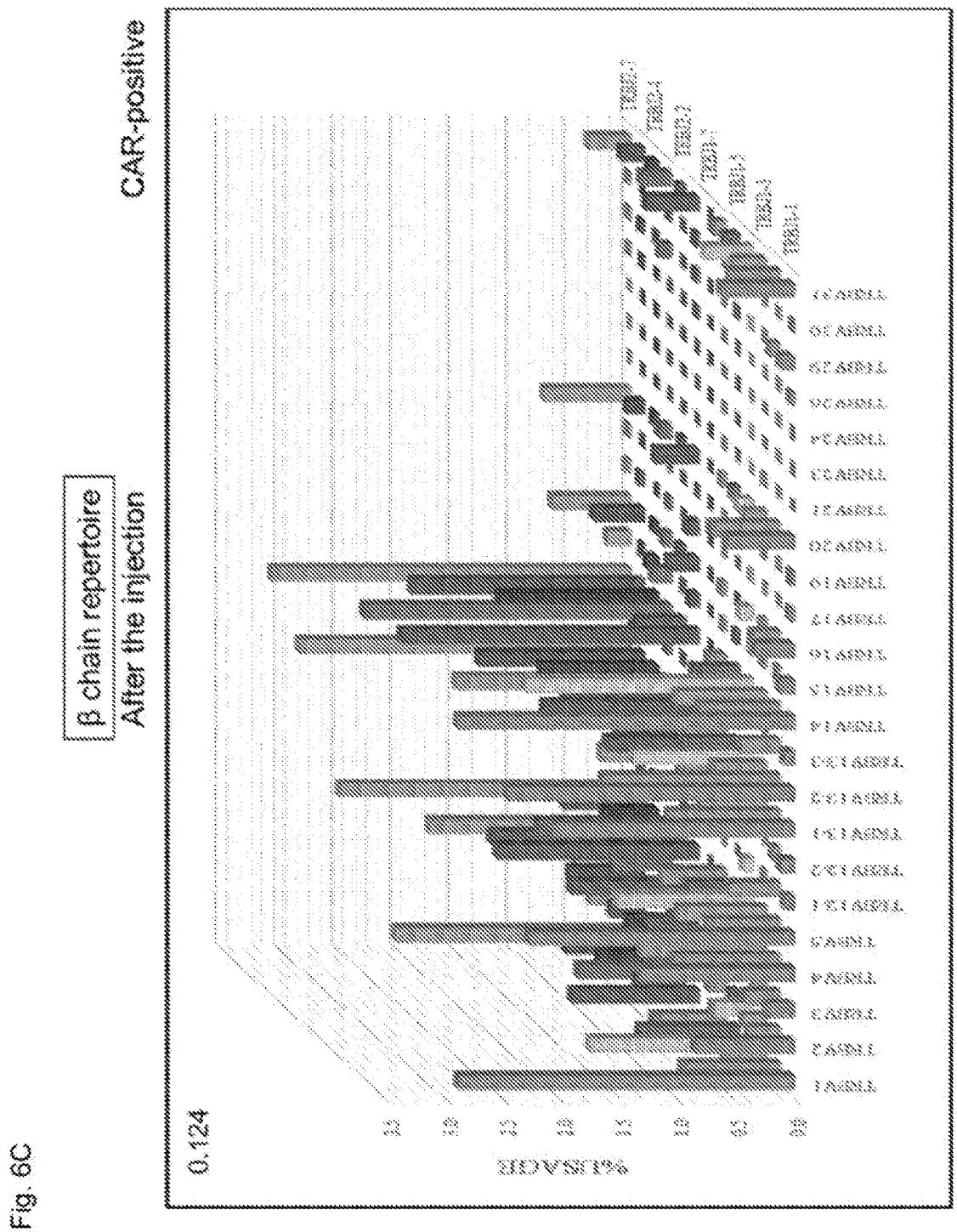
FIG. 6C is a graph showing results about Example 4 in which change in T-cell receptor (TCR) repertoire after treatment with CAR-IL-7/CCL19-expressing T-cells (β chain: after treatment, CAR-positive) was examined.
Figure 6D:
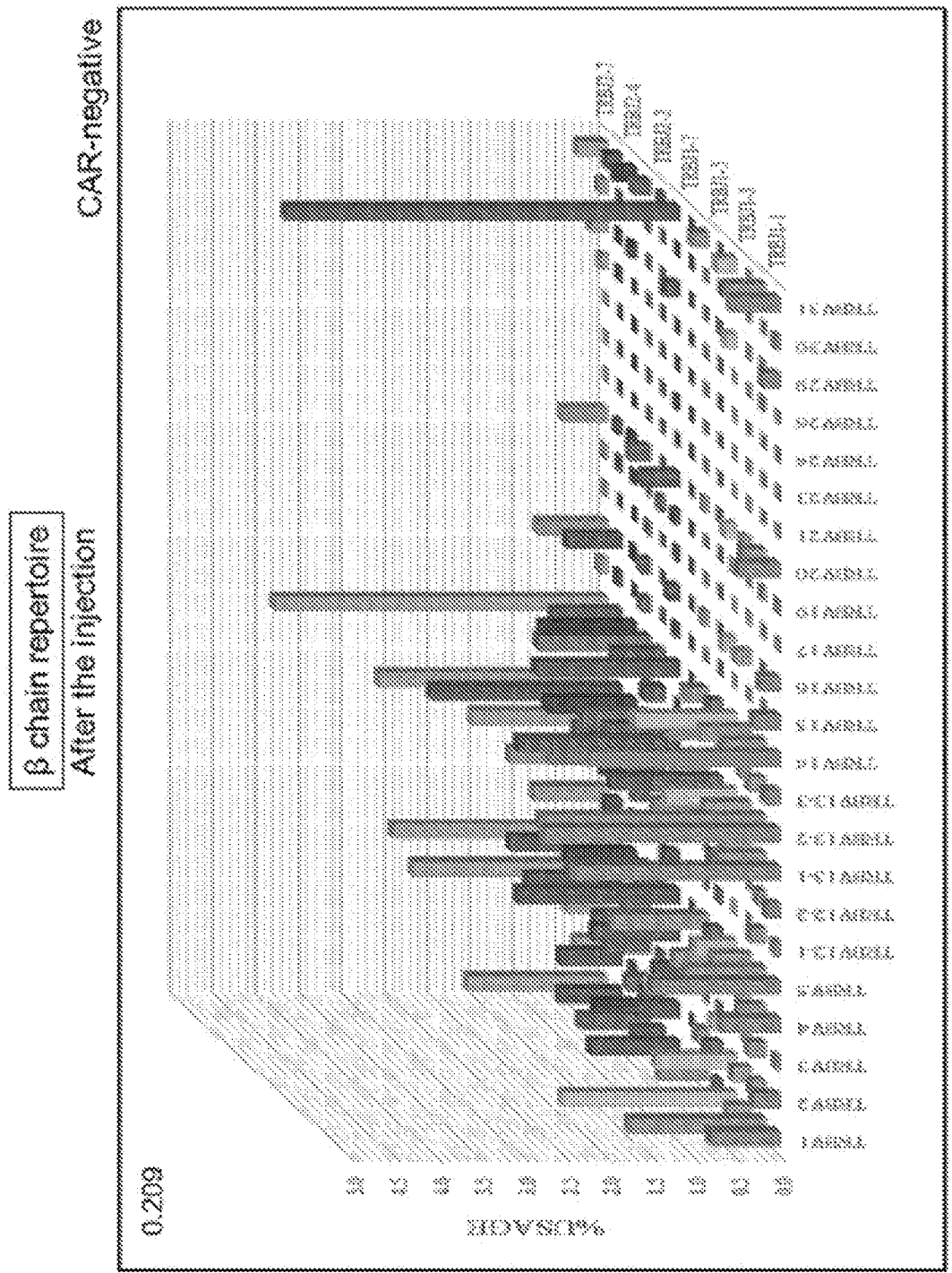
FIG. 6D is a graph showing results about Example 4 in which change in T-cell receptor (TCR) repertoire after treatment with CAR-IL-7/CCL19-expressing T-cells (β chain: after treatment, CAR-negative) was examined.

As shown in FIG. 3, in the case of administering the anti-human CD20 CAR-expressing T-cells (Conv.), the CD90.2-gated cells (recipient endogenous T-cells) included central memory T-cells (memory T-cell marker CD44-positive and CD62L-positive cells) at 5.5% of CD4-positive cells and 24.8% of CD8-positive cells. On the other hand, in the case of administering the anti-human CD20 CAR-IL-7/CCL19-expressing T-cells (7×19), the CD90.2-gated cells (recipient endogenous T-cells) included central memory T-cells at 6.76% of CD4-positive cells and 49.2% of CD8-positive cells. The ratio of central memory T-cells was increased in both the cases. These results demonstrated that the administration of the anti-human CD20 CAR-IL-7/CCL19-expressing T-cells (7×19), i.e., the co-secretion of IL-7 and CCL19 from single cells, can activate the recipient endogenous T-cells while inducing the differentiation of the recipient endogenous T-cells into central memory T-cells to increase the number of central memory T-cells and also increase the ratio of central memory T-cells to a spleen cell group. In other words, it is evident that the anti-human CD20 CAR-IL-7/CCL19-expressing T-cells can be used as an inducer for T-cells having a memory function in an administration subject, or an enhancer for T-cells having a memory function in an administration subject.

On the other hand, the CD90.1-gated cells (donor T-cells) included central memory T-cells at 75.8% of CD4-positive cells and 90.7% of CD8-positive cells, confirming that the donor T-cells themselves were induced into the central memory T-cells. In the case of using Conv., the CD90.1-gated cells were 0%, and the CD90.1-positive cells were not detected (n.d.) because Conv. expressed neither IL-7 nor CCL19 and exhibited a low survival rate of CAR-expressing T-cells.

As shown in FIG. 4, the donor cells included 90.5% CD4-positive cells and 93.6% CD8-positive cells producing IFN-γ by stimulation with 3LL. Also, among the recipient endogenous T-cells (expressing no CAR-T), while 0.957% of CD4-positive cells produced IFN-γ by the Conv. treatment, 14.9% of CD4 positive cells produced IFN-γ by the 7×19 treatment. These results demonstrated that by the secretion of IL-7 and CCL19 using the anti-human CD20 CAR-IL-7/CCL19-expressing T-cells, both the donor T-cells and the recipient cells produce IFN-γ by stimulation and acquire a memory function.

Example 4

<Change in Gene Expression Pattern of T-Cell Receptor>

In order to examine the diversity of T-cell epitopes, change in T-cell receptor (TCR) repertoire between before and after treatment with the CAR-IL-7/CCL19-expressing T-cells was examined. $5 \times 10^5$ cells of P815-hCD20 (mouse mastocytoma cells P815 allowed to express human CD20 by gene recombination) were subcutaneously inoculated to DBA/2 mice (n=5) (day 0). Then, on day 10, cyclophosphamide (CPA; 100 mg/kg) and $1 \times 10^6$ anti-human CD20 CAR-IL-7/CCL19-expressing T-cells were intravenously administered thereto to treat the tumor. On day 140 after the administration of P815 tumor cells, spleen cells were collected from mice completely cured by the treatment of the tumor as described above (tumor-rejected mice), and cultured with P815-hCD20 or the parent line P815 expressing no hCD20 (hCD20-negative: hCD20$^-$) for 4 days for the proliferation of CAR-positive T-cells or CAR-negative T-cells sorted using a cell sorter (SH800; manufactured by Sony Corp.). Then, for TCR repertoire analysis, CD8-positive and CAR-positive (CD8$^+$CAR$^-$) or CD8-positive and CAR-negative (CD8$^+$CAR$^-$) population was sorted using a flow cytometer. A CD8-positive and CAR-positive or CD8-positive and CAR-negative population before administration to mice was sorted as a control. The TCR repertoire was analyzed with a next-generation sequencer, and the frequency of use of V and J regions in α and β chains was indicated by 3-D graph. The results are shown in FIGS.

5A to 5D and 6A to 6D. FIGS. 5A to 5D show the results about the α chain, and FIGS. 6A to 6D show the results about the β chain. FIGS. 5A, 5B, 6A, and 6B show the results obtained before administration of cells of each line, and FIGS. 5C, 5D, 6C, and 6D show the results obtained after administration of cells of each line. The upper left numerical values in the diagrams represent diversity indexes calculated by the Pielou's index of evenness (a higher number indicates a less diversity) and mean that a lower numerical value indicates a higher diversity.

The T-cell receptor is an antigen receptor molecule expressed on the cell membranes of T-cells. The T-cell receptor exists as a heterodimer consisting of an α chain and a β chain or a γ chain and a δ chain, and is known to activate T-cells by recognizing an antigen molecule bound with major histocompatibility complex (MHC).

As is evident from the diversity indexes shown in FIGS. 5A to 5D and 6A to 6D, the diversity indexes value was increased for both the α chain and the β chains by the administration of the anti-human CD20 CAR-IL-7/CCL19-expressing T-cells. Thus, the diversity of TCR was reduced not only in the administered anti-human CD20 CAR-IL-7/CCL19-expressing T-cells but in the recipient endogenous T-cells, demonstrating that T-cells presumably having a memory function against tumor antigen by locally secreting IL-7 and CCL19 to tumor while destroying the tumor cells are selectively increased in number.

Example 5

<Inhibition of Tumor Recurrence—1>

Figure 7A:
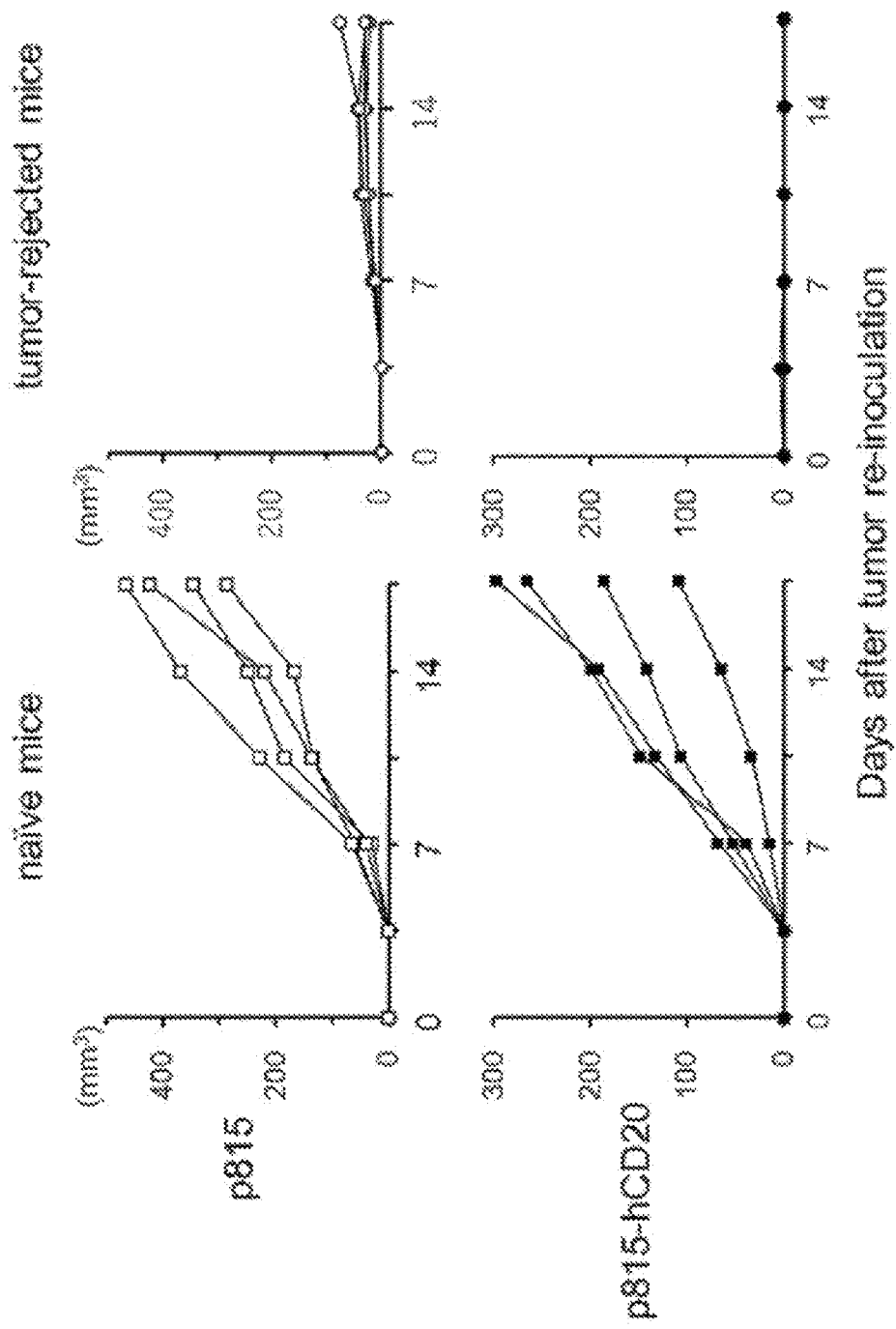
FIG. 7A is a diagram showing results of measuring tumor volumes in Example 5 in which P815-hCD20 or the parent line P815 expressing no hCD20 was inoculated to each of right and left lateral regions of the abdomens of tumor-rejected mice or control naive mice on day 140 after inoculation of P815-hCD20.
Figure 7B:
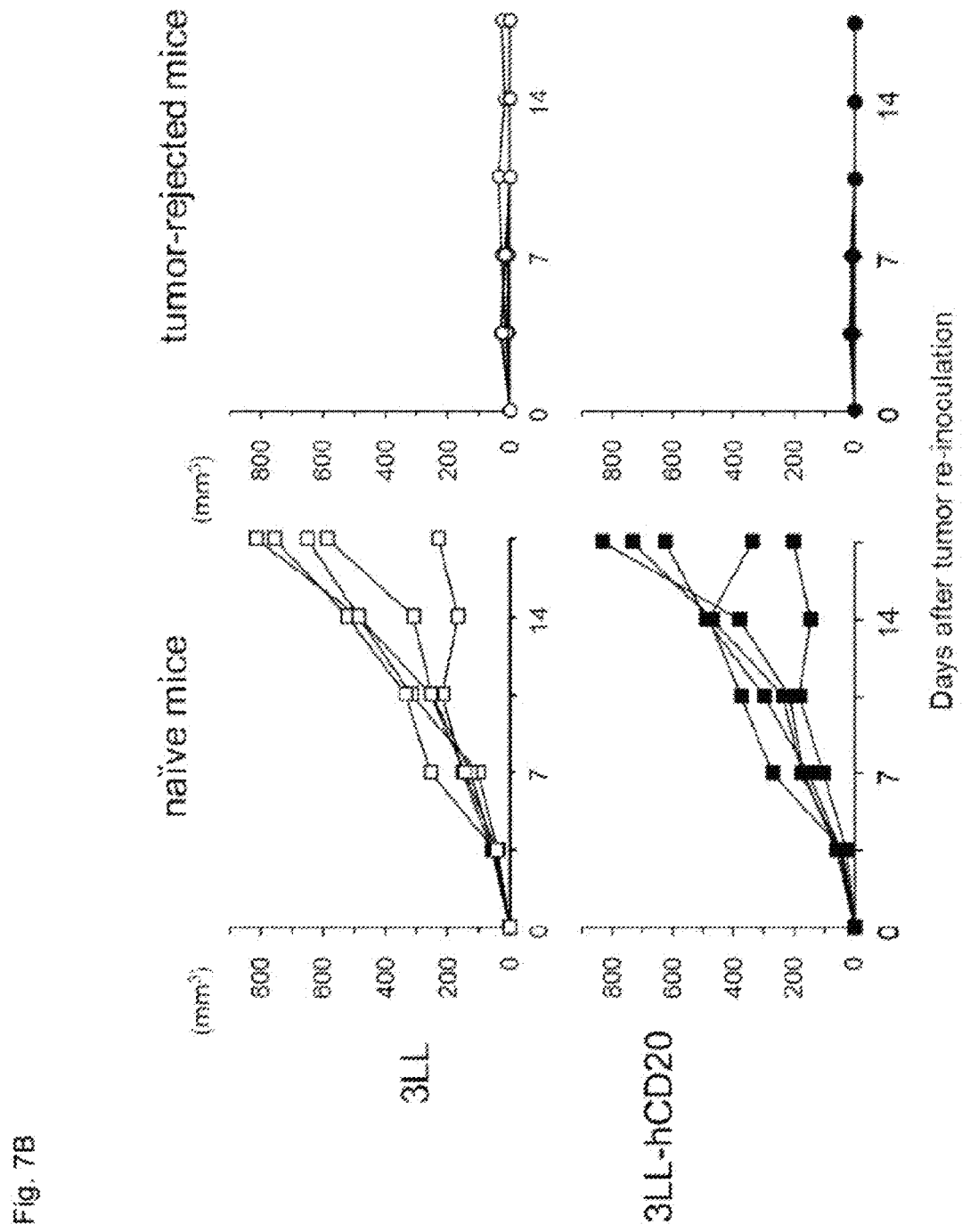
FIG. 7B is a diagram showing results of measuring tumor volumes in Example 5 in which 3LL-hCD20 or the parent line 3LL expressing no hCD20 was inoculated to each of right and left lateral regions of the abdomens of tumor-rejected mice or control naive mice on day 140 after inoculation of 3LL-hCD20.

Cancer recurrence models exploiting an animal were prepared by the following method: first, the tumor-specific memory response of recipient T-cells was examined in mice treated with the anti-human CD20 CAR-IL-7/CCL19-expressing T-cells. $5 \times 10^5$ cells of P815-hCD20 were subcutaneously inoculated to each of 7- to 10-week-old cancer-bearing mice (DBA/2; n=4; manufactured by Japan SLC, Inc.). Then, on day 10, an anticancer agent cyclophosphamide (CPA; 100 mg/kg) was intraperitoneally administered thereto. On day 14, $1 \times 10^6$ anti-human CD20 CAR-IL-7/CCL19-expressing T-cells were intravenously inoculated thereto. On day 140 after the inoculation of P815-hCD20, P815-hCD20 or the parent line P815 expressing no hCD20 was inoculated to each of right and left lateral regions of the abdomens of tumor-rejected mice or control naive mice. Tumor volumes were measured twice a week. The results are shown in FIG. 7A. Similar analysis was also conducted using C57BL/6 mice inoculated with 3LL-hCD20 or the parent line 3LL expressing no hCD20 instead of the P815-hCD20. The results are shown in FIG. 7B. The parent lines P815 and 3LL express no human CD20 and therefore serve as malignant tumor cells having no malignant tumor antigen that is specifically recognized by the cell surface molecule of the anti-human CD20 CAR-IL-7/CCL19-expressing T-cells.

The abscissa of FIG. 7A depicts the number of days from the day on which P815-hCD20 or P815 was initially administered (day 0) for the naive mice, and the number of days from the day on which P815-hCD20 was inoculated again on day 140 after the initial inoculation of P815-hCD20 (day 0) for the tumor-rejected mice. The abscissa of FIG. 7B depicts the number of days from the day on which 3LL-hCD20 or 3LL was initially administered (day 0) for the naive mice, and the number of days from the day on which 3LL-hCD20 was inoculated again (day 0) for the tumor-rejected mice. The ordinates of FIGS. 7A and 7B depict tumor volumes ($mm^3$).

As shown in the lower graphs of FIGS. 7A and 7B, no tumor was formed in the tumor-rejected mice inoculated with P815-hCD20 or 3LL-hCD20. These results demonstrated that the treatment of tumor with the anti-human CD20 CAR-IL-7/CCL19-expressing T-cells can inhibit tumor recurrence ascribable to tumor cells having an antigen that is recognized by CAR. As shown in the upper graphs of FIGS. 7A and 7B, surprisingly, tumor formation was markedly inhibited in the tumor-rejected mice inoculated with the parent line P815 or 3LL having no CD20 on the cell surface, as compared with the naive mice. These results demonstrated that the treatment with the anti-human CD20 CAR-IL-7/CCL19-expressing T-cells can also inhibit tumor formation ascribable to tumor cells having no antigen that is recognized by CAR, in other words, tumor recurrence ascribable to tumor cells having no antigen that is recognized by CAR. Such an event in which the administration of the anti-human CD20 CAR-IL-7/CCL19-expressing T-cells influences the immune function of an administration subject and inhibits recurrence by allowing the administration subject to continue to reject tumor derived from the parent line expressing no antigen targeted by CAR for a long period was unexpected from the viewpoint of the target molecule-specific reactivity of CAR-T-cells. When taken together with the results about change in gene expression pattern of the T-cell receptor in Example 4, the administration of the anti-human CD20 CAR-IL-7/CCL19-expressing T-cells caused destruction of tumor cells, and as a result, the recipient endogenous T-cells seemed to react with the tumor antigen originally carried by the tumor cells to induce a long-term memory function. This suggest that the administration of the anti-human CD20 CAR-IL-7/CCL19-expressing T-cells destroys tumor cells while locally secreting IL-7 and CCL19 to tumor, thereby inhibiting malignant tumor recurrence by very efficiently inducing an epitope spreading phenomenon and inducing and enhancing a memory function. For the above cancer recurrence models, first, P815-hCD20, P815, 3LL-hCD20, or 3LL was subcutaneously inoculated, and on day 140, the cells of each line were inoculated to each of right and left lateral regions of the abdomen. Hence, the administration of the anti-human CD20 CAR-IL-7/CCL19-expressing T-cells not only inhibited malignant tumor recurrence but may inhibit malignant tumor metastasis. Thus, the anti-human CD20 CAR-IL-7/CCL19-expressing T-cells are probably also available as a "malignant tumor metastasis inhibitor".

Example 6

<Inhibition of Tumor Recurrence—2>

Figure 8:
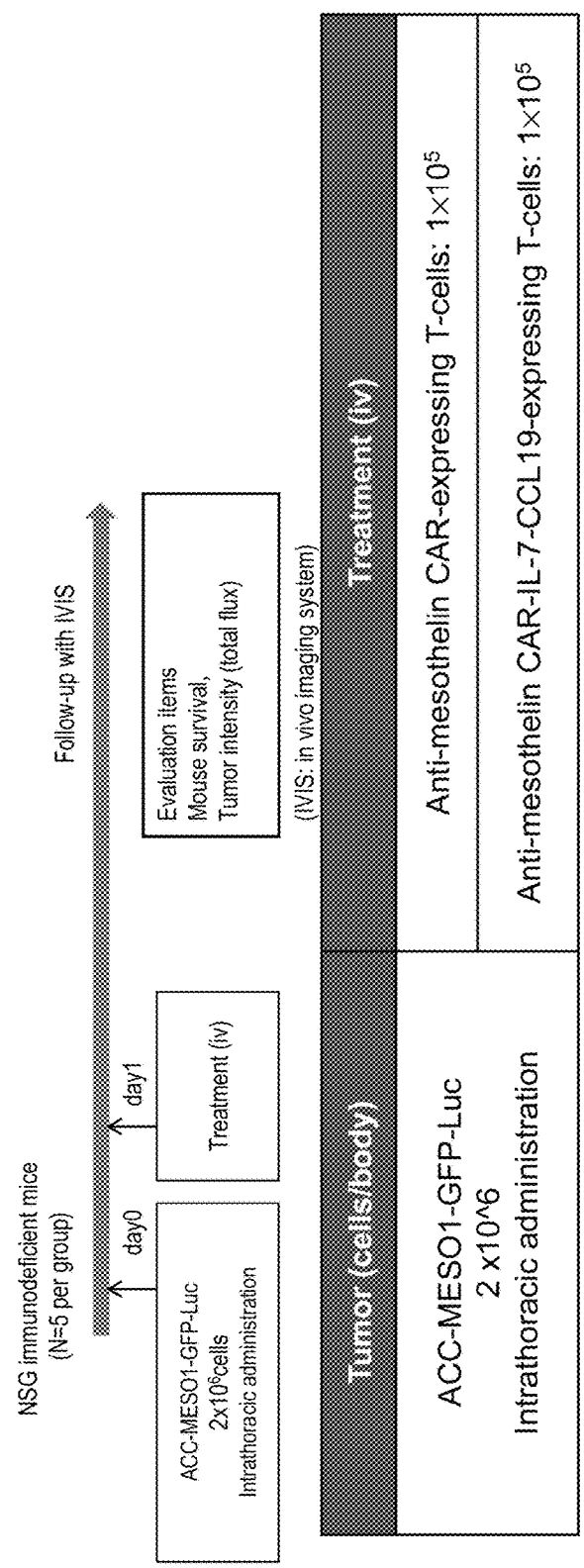
FIG. 8 is a diagram showing an experimental protocol for confirming a tumor recurrence inhibitory effect in Example 6.

In order to confirm a tumor recurrence inhibitory effect, tumor was formed by administering a human malignant pleural mesothelioma cell line to mice, and then, the presence or absence of tumor recurrence for 143 days was examined by the presence or absence of administration of the anti-human mesothelin CAR-IL-7/CCL19-expressing T-cells. FIG. 8 shows a specific experimental protocol. Methods for preparing "ACC-MESO1-GFP-Luc", "anti-mesothelin CAR-expressing T-cells", "anti-mesothelin CAR-IL-7/CCL19-expressing T-cells" shown in FIG. 8, and a method for activating T-cells are as follows.

(Preparation of ACC-MESO1-GFP-Luc Line)

A gene of green fluorescence protein-luciferase (GFP-Luc) was introduced using lentivirus to human malignant mesothelioma cell line ACC-MESO1, a mesothelin-positive tumor cell line kindly provided by Professor Yoshitaka Sekido from Aichi Cancer Center Research Institute.

On day 0, ACC-MESO1 was seeded at $1 \times 10^3$ cells/well to a 96-well plate. The culture medium used was RPMI1640 (manufactured by Gibco) supplemented with 10% FBS. On day 1, RediFect Red-FLuc-GFP (manufactured by PerkinElmer, Inc.), lentivirus particles for luminescent cell preparation, was added thereto at MOI 100 to start transduction. In order to enhance gene introduction efficiency, hexadimethrine bromide (manufactured by Sigma-Aldrich Co. LLC) was added to this culture medium such that the final concentration was 4 μg/mL. 24 hours after the virus addition (on day 2), the culture medium containing the virus was removed, and the culture medium was replaced with a fresh one. After continuation of culture, only cells expressing GFP were sorted using SH800 (manufactured by Sony Corp.) and used as the ACC-MESO1-GFP-Luc line.

(Preparation of Anti-Human Mesothelin CAR-IL-7-CCL19-Expressing T-Cells, and Anti-Human Mesothelin CAR-Expressing T-Cells)

The anti-human mesothelin CAR-IL-7-CCL19-expressing T-cells, and the anti-human mesothelin CAR-expressing T-cells (conventional CAR-expressing T-cells) were prepared on the basis of the methods described in Japanese Patent Application No. 2017-247109 and International Publication No. WO 2016/056228. As briefly described, a third-generation CAR construct (SEQ ID NO: 6) was prepared which had anti-human mesothelin single chain Fv consisting of the amino acid sequence of a heavy chain variable region set forth in SEQ ID NO: 3, the amino acid sequence of a linker set forth in SEQ ID NO: 4, and the amino acid sequence of a light chain variable region set forth in SEQ ID NO: 5, a human CD8 transmembrane region, and a human CD28-4-1BB-CD3ζ intracellular signal motif in this order. A gene of a construct having human IL-7 set forth in SEQ ID NO: 1, subsequent picornavirus-derived 2A peptide (F2A) set forth in SEQ ID NO: 7, human CCL19 set forth in SEQ ID NO: 2, and herpes virus-derived thymidine kinase gene (HSV-tk) in this order at the C terminus of the construct was prepared and inserted to pMSGV1 retroviral expression vector (Tamada k et al., Clin Cancer Res 18: 6436-6445 (2002)) to prepare pMSGV1 retroviral expression vector for the expression of human IL-7/CCL19 and HSV-tk. The obtained pMSGV1 retroviral expression vector was introduced to mouse T-cells using retrovirus to prepare the anti-human mesothelin CAR-IL-7-CCL19-expressing T-cells. Likewise, pMSGV1 retroviral expression vector for the expression of the third-generation CAR construct having anti-human mesothelin single chain Fv, a human CD8 transmembrane region, and a human CD28-4-1BB-CD3ζ intracellular signal motif in this order was introduced instead of the pMSGV1 retroviral expression vector for the expression of human IL-7/CCL19 and HSV-tk to mouse T-cells using retrovirus to prepare the anti-human mesothelin CAR-expressing T-cells (conventional anti-human mesothelin CAR-expressing T-cells). The signal peptide used was a signal peptide set forth in SEQ ID NO: 8.

(Activation of T-Cells)

On day 0, the culture of $2 \times 10^6$ peripheral blood mononuclear cells collected from healthy human donors, together with 200 IU/mL IL-2 (manufactured by PeproTech, Inc.) was started at 37° C. in a 6-well plate for cell culture on which 25 μL/mL RetroNectin (manufactured by Takara Bio Inc.) and 5 μg/mL anti-human CD3 monoclonal antibody (manufactured by Invitrogen Corp., 5 μg/mL) were immobilized, using a 5% $CO_2$ incubator. The culture solution used contained OpTmizer CTS (manufactured by Gibco) supplemented with 2 mM L-glutamine (manufactured by Gibco), 1% penicillin-streptomycin (manufactured by Wako Pure Chemical Industries, Ltd.) and 2.5 μg/mL fungizone (manufactured by Bristol-Myers Squibb Company). After culture for 3 days, T-cells on day 3 were confirmed under a microscope to be activated and morphologically changed.

(Observation of Tumor Recurrence)

Figure 9A:
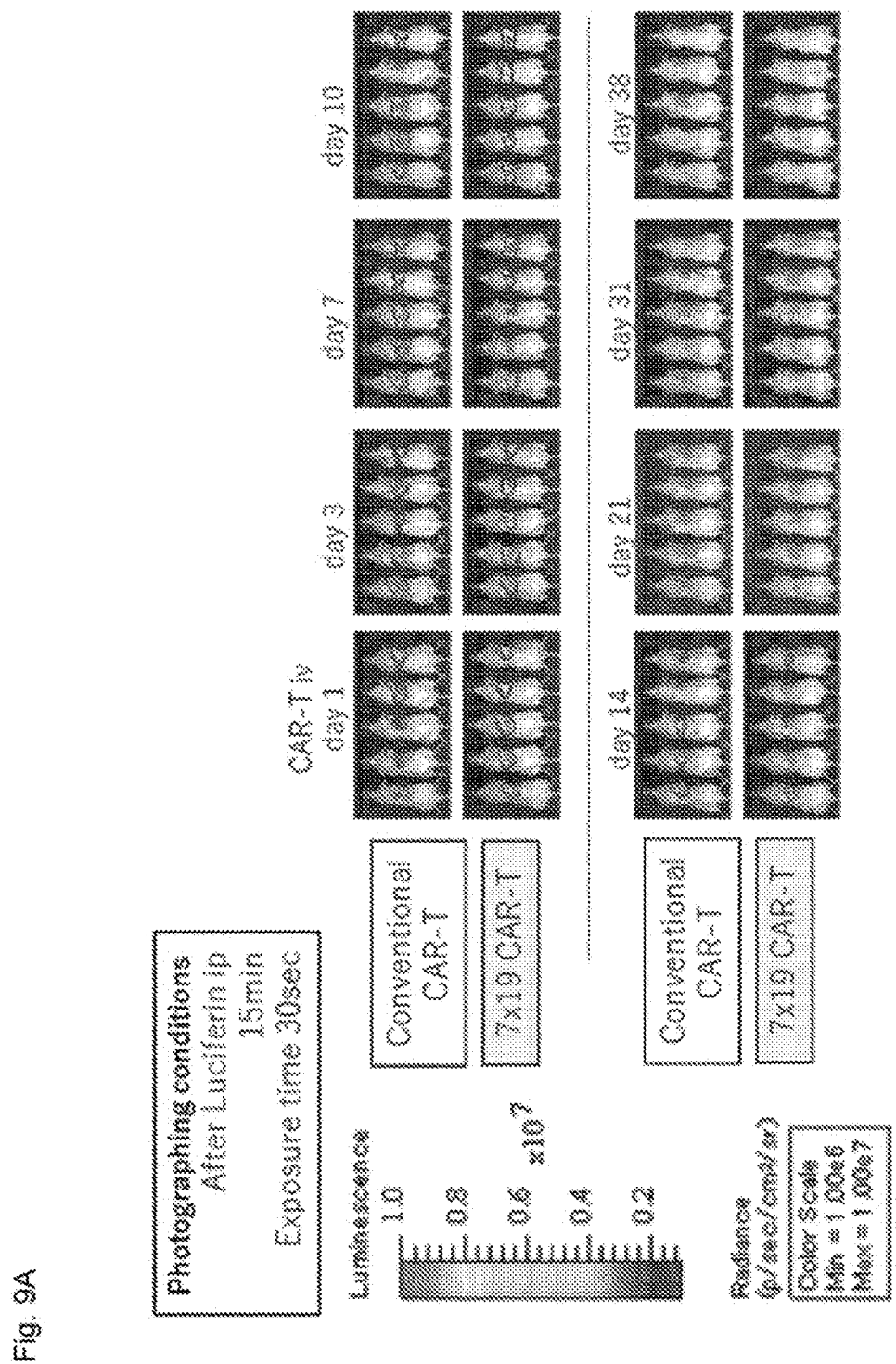
FIG. 9A is a diagram showing results about Example 6 in which after administration of ACC-MESO1-GFP-Luc mentioned later, mice of days 1, 3, 7, 10, 14, 21, 31, and 38 in a group given anti-human mesothelin CAR-IL-7-CCL19-expressing T-cells (7×19 CAR-T) and a group given conventional anti-human mesothelin CAR-expressing T-cells (conventional CAR-T) on day 1 were photographed for an exposure time of 30 seconds.
Figure 9B:
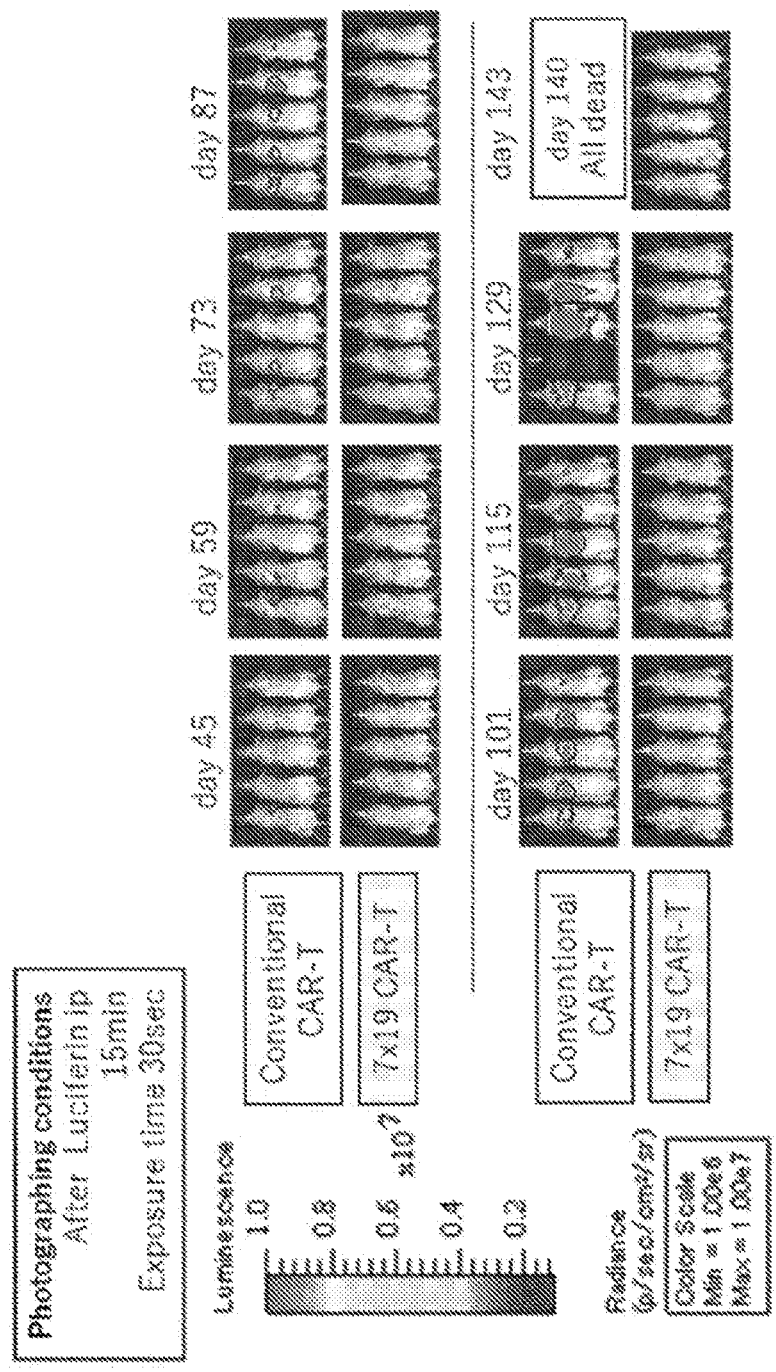
FIG. 9B is a diagram showing results about Example 6 in which after administration of ACC-MESO1-GFP-Luc mentioned later, mice of days 45, 59, 73, 87, 101, 115, 129, and 143 in a group given anti-human mesothelin CAR-IL-7-

First, on day 0, the ACC-MESO1-GFP-Luc was intrathoracically administered at $2 \times 10^6$ cells/mouse to 8-week-old female NSG immunodeficient mice. On day 1, intrathoracic tumor engraftment was confirmed using an in vivo imaging system (IVIS). On day 1, the conventional CAR-expressing T-cells, the anti-human mesothelin CAR-IL-7-CCL19-expressing T-cells, and the T-cells activated by the method, which had been prepared from healthy donor peripheral blood mononuclear cells (PBMC) and cryopreserved, were thawed. The conventional anti-human mesothelin CAR-expressing T-cells and the anti-human mesothelin CAR-IL-7-CCL19-expressing T-cells had a CAR expression rate of 49.6% and 32.5%, respectively. Therefore, the activated T-cells were added to the conventional anti-human mesothelin CAR-expressing T-cells to match their CAR expression rates. Then, a group given $1 \times 10^5$ cells of the conventional anti-human mesothelin CAR-expressing T-cells (N=5), and a group given $1 \times 10^5$ cells of the anti-human mesothelin CAR-IL-7-CCL19-expressing T-cells (N=5) were provided. The administration of the conventional anti-human mesothelin CAR-expressing T-cells and the anti-human mesothelin CAR-IL-7-CCL19-expressing T-cells was performed by intravenous administration through the tail veins. On day 3 or later, tumor fluorescence intensity was measured (total flux (photons/sec) using IVIS. The results are shown in FIGS. 9A and 9B. FIG. 10 graphically shows the relationship between the number of days from administration and mouse survival rates in the results described above. FIG. 11 graphically shows the relationship between the number of days from administration and the total amount of fluorescence (photons/second) in the results described above. In FIGS. 9A, 9B, 10, and 11, the mice given the anti-human mesothelin CAR-IL-7-CCL19-expressing T-cells are indicated by "7×19 CAR-T", and the mice given the conventional anti-mesothelin CAR-expressing T-cells are indicated by "Conventional CAR-T". In this Example 6, NSG immunodeficient mice defective in endogenous T-cells were used as recipients. Therefore, the influence of recipient endogenous T-cells was eliminated, and the effect of the administered anti-human mesothelin CAR-IL-7-CCL19-expressing T-cells themselves was evaluated.

As shown in FIGS. 9A, 9B, 10, and 11, tumor fluorescence intensity was rarely observed in both 7×19 CAR-T and Conventional CAR-T on or around day 21. Then, no tumor fluorescence was observed in 7×19 CAR-T up to day 143, confirming that recurrence was completely inhibited. On the other hand, tumor fluorescence became observable in Conventional CAR-T on or around day 45, and tumor fluorescence intensity was elevated on day 115, with one dead on day 129 and the remaining four also dead on day 143. These results demonstrated that malignant tumor recurrence can be inhibited by administering the CAR-IL-7-CCL19-expressing T-cells, i.e., locally secreting IL-7 and CCL19 to tumor while destroying tumor cells.

Example 7

<Memory Potential of Recipient Endogenous T-Cells>

Examples described above employed T-cells having CAR as the cell surface molecule that recognizes a malignant tumor antigen. The memory potential of recipient endogenous T-cells was examined using T-cells having a T-cell receptor (TCR) instead of CAR as the cell surface molecule that recognizes a malignant tumor antigen.

(Preparation of P1A-Specific TCR/IL-7/CCL19/eGFP-Expressing T-Cells)

T-cells expressing TCR specific for the tumor antigen P1A of P815, mouse IL-7, mouse CCL19, and GFP were prepared in accordance with the method described in patent document 3. The preparation method will be briefly described below.

An IL-7-F2A-CCL19 DNA fragment encoding mouse IL-7 (without a stop codon), subsequent picornavirus-derived 2A peptide (F2A), and mouse CCL19 was artificially synthesized (Life Technologies Corp.). The IL-7-F2A-CCL19 DNA fragment thus synthesized was inserted to the multicloning site of pMSGV retroviral expression vector (patent document 3) having a F2A-eGFP sequence by restriction enzyme (NCOI and ECORI) treatment and ligation to obtain pMSGV vector comprising an IL-7-F2A-CCL19-F2A-eGFP DNA fragment (SEQ ID NO: 9) (IL-7× CCL19-eGFP expression vector). Also, pMSGV vector comprising eGFP and comprising neither IL-7 nor CCL19 (eGFP control vector) was prepared as a control. In SEQ ID NO: 9, nucleotides 1 to 462 correspond to a nucleic acid encoding IL-7 (nucleotides 1 to 75 correspond to a nucleic acid encoding a signal sequence of IL-7), nucleotides 463 to 537 correspond to a nucleic acid encoding F2A, nucleotides 538 to 861 correspond to a nucleic acid encoding CCL19 (nucleotides 538 to 612 correspond to a nucleic acid encoding a signal sequence of CCL19), nucleotides 868 to 942 correspond to a nucleic acid encoding F2A, nucleotides 946 to 1662 correspond to a nucleic acid encoding eGFP, and nucleotides 1663 to 1665 correspond to a stop codon.

Spleen cells were collected from transgenic mice expressing TCR specific for H-2L$^d$-restricted tumor antigen P1A of P815 (Sarma, S., Y. Guo, Y. Guilloux, C. Lee, X.-F. Bai, Y. Liu. 1999. J. Exp. Med. 189:811.) obtained from Y. Liu. Spleen cell-derived mouse T-cells expressing TCR specific for the tumor antigen P1A of P815 (P1A-specific TCR-T-cells) were obtained therefrom. Subsequently, retrovirus harboring the IL-7×CCL19-eGFP expression vector or the eGFP control vector was prepared, and cells obtained by activating the spleen cells (3×10$^6$ cells/well) including the P1A-specific TCR-T-cells with P1A peptide for 48 hours were transduced with the retrovirus to obtain P1A-specific TCR/IL-7/CCL19/eGFP-expressing T-cells (7×19 P1A-CTL) or P1A-specific TCR/eGFP-expressing T-cells (conv. P1A-CTL). The transduction with each expression vector was confirmed by flow cytometry analysis of detecting eGFP as a surrogate marker. The eGFP expression level of the obtained T-cells of each line was 70 to 80% in all the experiments.

FIGS. 12(a) and 12(b) show results of analyzing the ratio of CD8$^+$GFP$^+$ cells to spleen cells and the absolute number of CD8$^+$GFP$^+$ cells in mice treated with the P1A-specific TCR/IL-7/CCL19/eGFP-expressing T-cells or the P1A-specific TCR/eGFP-expressing T-cells by flow cytometry. The treatment with the P1A-specific TCR/IL-7/CCL19/eGFP-expressing T-cells was confirmed to increase the ratio of CD8$^+$GFP$^+$ cells to spleen cells and the absolute number of CD8$^+$GFP$^+$ cells.

FIGS. 13(a) and 13(b) show results of analyzing the expression of CD44 in CD8$^+$ spleen cells of naive BDA/2 mice and CD8$^+$GFP$^-$ or CD8$^+$GFP$^+$ spleen cells of mice treated with the P1A-specific TCR/IL-7/CCL19/eGFP-expressing T-cells by flow cytometry. FIG. 13(a) shows the representative number of CD44$^+$ cells. FIG. 13(b) shows the proportion of CD44$^+$ cells. As shown in FIGS. 13(a) and 13(b), not only the administered T-cells (GFP$^+$ gated) but the recipient endogenous T-cells (GFP$^-$ gated) had the proportion of CD44$^+$ cells increased by two or more times as compared with the naive T-cells. Thus, the P1A-specific TCR/IL-7/CCL19/eGFP-expressing T-cells were confirmed to have the action of imparting memory potential to recipient intrinsic T-cells, i.e., the action of inducing a memory function in recipient intrinsic T-cells and enhancing the memory function in the recipient intrinsic T-cells.

In order to further confirm the acquirement of the function of memory potential, i.e., reactivity with stimulation, this acquirement was examined by the production of IFN-γ. T-cells were magnetically isolated from spleen cells and cocultured for approximately 5 days with mucosal mast cells (MMC) treated with P815. FIG. 14 shows results of detecting the concentration of IFN-γ in a supernatant of the culture medium by ELISA (enzyme-linked immunosorbent assay). As shown in FIG. 14, the P1A-specific TCR/IL-7/CCL19/eGFP-expressing T-cells were confirmed to be rich in the production of IFN-γ. Thus, the P1A-specific TCR/IL-7/CCL19/eGFP-expressing T-cells were confirmed to improve the antitumor activity of the recipient endogenous T-cells. This suggested that the P1A-specific TCR/IL-7/CCL19/eGFP-expressing T-cells induce a recurrence inhibitory effect in recipients.

Example 8

<Virus Expressing IL-7 and CCL19>

Examples described above employed an immune cell as the nucleic acid delivery vehicle. Enhancement in T-cells or B-cells having a memory function or inhibition of malignant tumor recurrence in an administration subject must be achieved without the use of the immune cell as long as IL-7 and CCL19 are locally secreted to tumor. Accordingly, analysis was conducted using a virus instead of the immune cell as the nucleic acid delivery vehicle.

(Preparation of Genetically Recombinant Vaccinia Virus Expressing Mouse IL-7 and Mouse CCL19)

A genetically recombinant vaccinia virus expressing mouse IL-7 and mouse CCL19 was prepared by the following method in accordance with the method described in patent document 3 and International Publication No. WO 2011/125469. A blue fluorescent protein (BFP) gene region was amplified with DNA of pTagBFP-N vector (FP172, Evrogen) as a template using two primers (5'-ATG GCC GGA CCG GCC ACC GGT CGC CAC CAT GAG CGA G-3': SEQ ID NO: 10) and (5'-TCG AAT TCG CTA GCG GCC GCT TAA TTA AGC TTG TGC CCC AG-3': SEQ ID NO: 11). The PCR product was cleaved with restriction enzymes SfiI and EcoRI, and the resultant was cloned into the corresponding restriction site of pTK-SP-LG vector (International Publication No. WO 2011/125469) to construct pTK-SP-BFP in which the BFP gene was linked under synthetic vaccinia virus promoter (Hammond J M. et al., Journal of Virological Methods. 1997; 66 (1): 135-138). Subsequently, pAmCyan1-N1 vector (manufactured by Takara Bio Inc.) was cleaved with restriction enzymes AgeI and NotI, and the resulting fluorescence protein AmCyan1 fragment was cloned into a site, treated with the same restriction enzymes thereas, of pTK-SP-BFP to construct pTK-SP-AmCyan1.

pMSGV plasmid comprising a DNA fragment encoding mouse IL-7, subsequent picornavirus-derived 2A peptide (F2A), mouse CCL19, F2A, and eGFP (patent document 3) was cleaved with restriction enzyme BamHI, treated for blunt end, and then cleaved with NcoI. The obtained mouse IL-7-F2A-mouse CCL19-F2A-eGFP fragment was cloned into a site obtained by the cleavage of pTK-SP-AmCyan1 with NheI and treatment for blunt end, followed by cleavage with NcoI to construct transfer vector plasmid pTK-SP-mouse IL-7-F2A-mouse CCL19-F2A-eGFP.

A firefly luciferase gene region was amplified with DNA of pGL4.20 (manufactured by Promega Corp.) as a template using two primers (5'-GCT CCG GAC GCC ACC ATG GAA GAT GCC AAA AAC-3' (SEQ ID NO: 12) and 5'-GCG AAT TCC ACG GCG ATC TTG CCG CCC TTC T-3' (SEQ ID NO: 13)). The PCR product was cleaved with restriction enzymes BspEI and EcoRI, and the obtained Luc fragment, and a fragment comprising a portion of eGFP, obtained by the cleavage of pTK-SP-mouse IL-7-F2A-mouse CCL19-F2A-eGFP with restriction enzymes EcoRI and BsrGI were simultaneously cloned into a site of pTK-SP-mouse IL-7-F2A-mouse CCL19-F2A-eGFP cleaved with restriction enzymes BspEI and BsrGI to construct transfer vector plasmid pTK-SP-Luc-F2A-eGFP.

In order to recover a recombinant vaccinia virus having the viral genome shown in FIG. 15(a) or 15(b), CV1 cells cultured at 80% confluency in a 6-well dish were infected with vaccinia virus (LC16mO) at MOI=0.02 to 0.1. After adsorption at room temperature for 1 hour, transfer vector plasmid DNA (pTK-SP-mouse IL-7-F2A-mouse CCL19-F2A-eGFP or pTK-SP-Luc-F2A-eGFP) mixed with FuGENE HD (manufactured by Promega Corp.) was added to the cells according to the manual so that the cells incorporated the DNA. The cells were cultured at 37° C. for 2 to 5 days. The cells were recovered, frozen and thawed, then sonicated, appropriately diluted and inoculated into almost confluent BSC1 cells. Eagle MEM culture medium containing 0.8% methylcellulose and 5% FBS was added thereto, and the cells were cultured at 37° C. for 2 to 5 days. The culture medium was removed, and BFP-expressing plaques were scraped off with a pipette tip and suspended in Opti-MEM culture medium (manufactured by Invitrogen Corp.). This operation was further repeated three or more times using BSC1 cells to purify the plaques. The suspension of the plaques collected after the plaque purification was sonicated. Then, genomic DNA was extracted from a 200 µL aliquot thereof using High Pure Viral Nucleic Acid Kit (manufactured by F. Hoffmann-La Roche, Ltd.) according to the manual and subjected to screening by PCR. PCR was performed using two primers (5'-ATT TCT CCG TGA TAG GTA TCG ATG-3' (SEQ ID NO: 14) and 5'-AAC GGT TTA CGT TGA AAT GTC C-3'SEQ ID NO: 15), and clones with a predetermined size of a PCR product detected were directly sequenced to confirm the nucleotide sequence of the PCR product. A virus clone having no problem in the nucleotide sequence was selected and amplified in A549 cells, followed by virus titer measurement in RK13 cells. The obtained virus was subjected as genetically recombinant vaccinia virus LC16mO TK-SP-mouse IL-7-F2A-mouse CCL19-F2A-eGFP (TK-ICE; FIG. 15(a)) or LC16mO TK-SP-Luc-F2A-eGFP (TK-LE; FIG. 15(b)) to the following experiment.

A549 cells ($1 \times 10^3$ cells/well) or CT26 cells ($5 \times 10^4$ cells/well) were seeded to a 24-well plate and cultured at 37° C. Then, the A549 cells and the CT26 cells were infected with TK-ICE or TK-LE at MOI=0.1 and MOI=10, respectively (n=3). 24, 48, and 72 hours after the infection, the cells were observed under a fluorescence microscope (manufactured by Olympus Corp.) (FIG. 16), and supernatants were recovered therefrom. The supernatant recovered from the cells of each line 24, 48, or 72 hours later were diluted 100-fold, and the amounts of IL-7 and CCL19 secreted in 0.5 mL of the supernatant were measured using DuoSet ELISA Mouse IL-7 (DY407 manufactured by R&D Systems, Inc.), DuoSet ELISA Mouse CCL-19 (DY440 manufactured by R&D Systems, Inc.), and DuoSet Ancillary Reagent Kit 2 (DY008 manufactured by R&D Systems, Inc.). The measurement results are shown in FIG. 17.

As shown in FIGS. 16 and 17, eGFP fluorescence emission from the A549 cells and the CT26 cells 24, 48, or 72 hours after the infection was at the same level between TK-ICE and TK-LE. The eGFP fluorescence emission was detected in almost all the A549 cells 48 hours after the infection. The eGFP fluorescence emission was increased in the CT26 cells with a lapse of time. IL-7 and CCL19 were detected from 24 hours after the infection in the A549 cells and CT26 cells infected with TK-ICE. The amounts of IL-7 and CCL19 in the A549 cells reached almost a plateau 48 hours after the infection. The amounts of IL-7 and CCL19 in the CT26 cells were elevated with a lapse of time. On the other hand, the amounts of IL-7 and CCL19 were equal to or lower than the detection limits in the cells infected with TK-LE. From these results, TK-ICE was confirmed to secrete IL-7 and CCL19 while destroying tumor cells.

Example 9

<Antitumor Effect>

In Example 8, the genetically recombinant vaccinia virus TK-ICE prepared as described above was confirmed to secrete IL-7 and CCL19 while destroying cancer cells by infecting the tumor cells. Accordingly, the genetically recombinant vaccinia virus TK-ICE was examined for its antitumor effect.

As shown in FIG. 18, mouse large intestine cancer CT26 cells ($5 \times 10^5$ cells) were subcutaneously transplanted to right and left abdominal parts of each of BALB/c mice and allowed to grow. Subsequently, each genetically recombinant vaccinia virus (3 to $5 \times 10^7$ plaque-forming units (PFU)) was intratumorally administered a total of three times (days 0, 2, and 4) to a larger one selected from tumors formed in the right and left abdominal parts. Then, the antitumor effect of the virus was studied by tumor diameter measurement in the right and left abdominal parts. The tumor on the administration side before the first dosage was 43 to 102 mm$^3$, and the tumor on the non-administration side before the first dosage was 24 to 82 mm$^3$. The results are shown in FIG. 19.

From the result of FIG. 19, the proliferation of the tumor on the administration side was suppressed in the group given TK-LE expressing neither IL-7 nor CCL19 (N=7) as compared with a PBS administration group (N=8), whereas no tumor suppressive effect was seen in the non-administration group. By contrast, the suppression of tumor proliferation was seen not only in the tumor on the administration side but in the tumor on the non-administration side in the group given TK-ICE expressing IL-7 and CCL19 (N=4) as compared with a PBS administration group (N=4). The genetically recombinant vaccinia virus administered to tumor on one side of the abdominal parts was confirmed to be not migrated to tumor on the other side, by a method for noninvasively detecting a virus by administering a substrate (luciferin) for a luminescent enzyme (luciferase) expressed in tumor cells infected with TK-LE, and confirming the presence or absence of luminescence (not shown). This suggests that the destruction of tumor cells by TK-ICE as well as the local secretion of IL-7 and CCL19 to tumor triggers tumor immunity in an administration subject while enhancing the memory function of endogenous T-cells, thereby confirming not only disappearance of tumor on the administration side but suppression of tumor proliferation on the non-administration side, and inhibiting the recurrence of the malignant tumor.

The invention claimed is:

1. A composition comprising a nucleic acid delivery vehicle, a nucleic acid encoding interleukin-7 (IL-7), and a nucleic acid encoding chemokine (C-C motif) ligand 19 (CCL19), wherein the nucleic acid delivery vehicle comprises an oncolytic virus.

2. A pharmaceutical composition comprising the composition according to claim 1 and a pharmaceutically acceptable additive.

3. The composition according to claim 1, wherein the oncolytic virus is selected from the group consisting of oncolytic vaccinia virus, oncolytic adenovirus, oncolytic herpes simplex virus, oncolytic reovirus, oncolytic measles virus, oncolytic Newcastle disease virus, oncolytic cowpox virus, oncolytic mumps virus, and oncolytic coxsackievirus.

4. The composition according to claim 1, wherein the composition has $10^5$ to $10^6$ plaque-forming units (PFU) of the oncolytic virus.

5. The composition according to claim 1, wherein the malignant tumor is malignant solid tumor.

6. The composition according to claim 1, wherein the malignant tumor is malignant blood tumor.

7. The composition according to claim 1, wherein the malignant tumor is selected from the group consisting of glioma, melanoma, malignant mesothelioma, adenocarcinoma, squamous cell carcinoma, adenosquamous carcinoma, anaplastic cancer, large-cell cancer, small-cell cancer, skin cancer, thyroid gland cancer, breast cancer, prostate cancer, urinary bladder cancer, vaginal cancer, head and neck cancer, neck cancer, uterine cancer, liver cancer, kidney cancer, pancreatic cancer, spleen cancer, lung cancer, trachea cancer, bronchial cancer, large intestine cancer, colon cancer, small intestine cancer, stomach cancer, esophageal cancer, biliary tract cancer, gallbladder cancer, testis cancer, ovary cancer, and brain tumor, a cancer of a bone tissue, a cartilage tissue, an adipose tissue, a muscle tissue, a vascular tissue, or a hematopoietic tissues as well as a sarcoma such as chondrosarcoma, Ewing's sarcoma, malignant hemangioendothelioma, malignant schwannoma, osteosarcoma, and soft tissue sarcoma, a blastoma such as hepatoblastoma, medulloblastoma, nephroblastoma, neuroblastoma, pancreatoblastoma, pleuropulmonary blastoma, and retinoblastoma, germ cell tumor, lymphoma, leukemia, and myeloma.

8. The composition according to claim 1, wherein the composition or the oncolytic virus comprises a nucleic acid encoding a suicide gene.

9. A method of decreasing malignant tumor recurrence in a subject comprising: administering to the subject a composition comprising a nucleic acid delivery vehicle, a nucleic acid encoding interleukin-7 (IL-7), and a nucleic acid encoding chemokine (C-C motif) ligand 19 (CCL19), wherein the nucleic acid delivery vehicle comprises an oncolytic virus.

10. The method according to claim 9, wherein the composition further comprises a pharmaceutically acceptable additive.

11. The method according to claim 9, wherein the oncolytic virus is selected from the group consisting of oncolytic vaccinia virus, oncolytic adenovirus, oncolytic herpes simplex virus, oncolytic reovirus, oncolytic measles virus, oncolytic Newcastle disease virus, oncolytic cowpox virus, oncolytic mumps virus, and oncolytic coxsackievirus.

12. The method according to claim 9, wherein the composition has $10^5$ to $10^6$ plaque-forming units (PFU) per dosage of the oncolytic virus.

13. The method according to claim 9, wherein the malignant tumor is malignant solid tumor.

14. The method according to claim 9, wherein the malignant tumor is malignant blood tumor.

15. The method according to claim 9, wherein the malignant tumor is selected from the group consisting of glioma, melanoma, malignant mesothelioma, adenocarcinoma, squamous cell carcinoma, adenosquamous carcinoma, anaplastic cancer, large-cell cancer, small-cell cancer, skin cancer, thyroid gland cancer, breast cancer, prostate cancer, urinary bladder cancer, vaginal cancer, head and neck cancer, neck cancer, uterine cancer, liver cancer, kidney cancer, pancreatic cancer, spleen cancer, lung cancer, trachea cancer, bronchial cancer, large intestine cancer, colon cancer, small intestine cancer, stomach cancer, esophageal cancer, biliary tract cancer, gallbladder cancer, testis cancer, ovary cancer, and brain tumor, a cancer of a bone tissue, a cartilage tissue, an adipose tissue, a muscle tissue, a vascular tissue, or a hematopoietic tissues as well as a sarcoma such as chondrosarcoma, Ewing's sarcoma, malignant hemangioendothelioma, malignant schwannoma, osteosarcoma, and soft tissue sarcoma, a blastoma such as hepatoblastoma, medulloblastoma, nephroblastoma, neuroblastoma, pancreatoblastoma, pleuropulmonary blastoma, and retinoblastoma, germ cell tumor, lymphoma, leukemia, and myeloma.

16. The method according to claim 9, further comprising administering an additional antitumor agent.

17. The method according to claim 9, further comprising a radiation cancer treatment.

18. The method according to claim 9, wherein the composition or the oncolytic virus comprises a nucleic acid encoding a suicide gene.

* * * * *

UNITED STATES PATENT AND TRADEMARK OFFICE
CERTIFICATE OF CORRECTION

PATENT NO. : 11,617,765 B2
APPLICATION NO. : 16/754645
DATED : April 4, 2023
INVENTOR(S) : Tamada et al.

It is certified that error appears in the above-identified patent and that said Letters Patent is hereby corrected as shown below:

On the Title Page

At Item (73): Replace "Totori University" with --Tottori University--.

Signed and Sealed this
Thirteenth Day of August, 2024

Katherine Kelly Vidal
*Director of the United States Patent and Trademark Office*

SEQUENCE LISTING

<160> NUMBER OF SEQ ID NOS: 15

<210> SEQ ID NO 1
<211> LENGTH: 177
<212> TYPE: PRT
<213> ORGANISM: artificial
<220> FEATURE:
<223> OTHER INFORMATION: human IL-7 AA
<220> FEATURE:
<221> NAME/KEY: MISC_FEATURE
<223> OTHER INFORMATION: Inventor: Tamada, Koji
    Inventor: Sakoda, Yukimi
    Inventor: Adachi, Keishi
    Inventor: Nakamura, Takafumi

<400> SEQUENCE: 1

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 2
<211> LENGTH: 98
<212> TYPE: PRT
<213> ORGANISM: artificial
<220> FEATURE:
<223> OTHER INFORMATION: human CCL19 AA

<400> SEQUENCE: 2

Met Ala Leu Leu Leu Ala Leu Ser Leu Leu Val Leu Trp Thr Ser Pro
1               5                   10                  15

Ala Pro Thr Leu Ser Gly Thr Asn Asp Ala Glu Asp Cys Cys Leu Ser
            20                  25                  30

Val Thr Gln Lys Pro Ile Pro Gly Tyr Ile Val Arg Asn Phe His Tyr
        35                  40                  45

Leu Leu Ile Lys Asp Gly Cys Arg Val Pro Ala Val Val Phe Thr Thr
    50                  55                  60

Leu Arg Gly Arg Gln Leu Cys Ala Pro Pro Asp Gln Pro Trp Val Glu
65                  70                  75                  80

Arg Ile Ile Gln Arg Leu Gln Arg Thr Ser Ala Lys Met Lys Arg Arg

```
                    85                  90                  95

Ser Ser

<210> SEQ ID NO 3
<211> LENGTH: 128
<212> TYPE: PRT
<213> ORGANISM: artificial
<220> FEATURE:
<223> OTHER INFORMATION: VH07_aa

<400> SEQUENCE: 3

Gln Val Gln Leu Gln Gln Ser Gly Pro Gly Leu Val Thr Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Met Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Met Met Thr Tyr Tyr Gly Met Asp Val
            100                 105                 110

Trp Gly Gln Gly Thr Thr Val Thr Val Ser Ser Gly Ile Leu Gly Ser
        115                 120                 125

<210> SEQ ID NO 4
<211> LENGTH: 15
<212> TYPE: PRT
<213> ORGANISM: artificial
<220> FEATURE:
<223> OTHER INFORMATION: linker 15_aa

<400> SEQUENCE: 4

Gly Gly Gly Gly Ser Gly Gly Gly Ser Gly Gly Gly Gly Ser
1               5                   10                  15

<210> SEQ ID NO 5
<211> LENGTH: 116
<212> TYPE: PRT
<213> ORGANISM: artificial
<220> FEATURE:
<223> OTHER INFORMATION: VL07_aa

<400> SEQUENCE: 5

Gln Pro Val Leu Thr Gln Ser Ser Ser Leu Ser Ala Ser Pro Gly Ala
1               5                   10                  15

Ser Ala Ser Leu Thr Cys Thr Leu Arg Ser Gly Ile Asn Val Gly Pro
            20                  25                  30

Tyr Arg Ile Tyr Trp Tyr Gln Gln Lys Pro Gly Ser Pro Pro Gln Tyr
        35                  40                  45

Leu Leu Asn Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Val
65                  70                  75                  80

Leu Leu Ile Ser Gly Leu Arg Ser Glu Asp Glu Ala Asp Tyr Tyr Cys
                85                  90                  95
```

```
Met Ile Trp His Ser Ser Ala Ala Val Phe Gly Gly Gly Thr Gln Leu
            100                 105                 110

Thr Val Leu Ser
        115

<210> SEQ ID NO 6
<211> LENGTH: 283
<212> TYPE: PRT
<213> ORGANISM: artificial
<220> FEATURE:
<223> OTHER INFORMATION: hCD8-hCD28-h4-1BB-hCD3

<400> SEQUENCE: 6

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg Ser Lys Arg Ser Arg Leu Leu His Ser Asp Tyr Met
                85                  90                  95

Asn Met Thr Pro Arg Arg Pro Gly Pro Thr Arg Lys His Tyr Gln Pro
            100                 105                 110

Tyr Ala Pro Pro Arg Asp Phe Ala Ala Tyr Arg Ser Arg Phe Ser Val
        115                 120                 125

Val Lys Arg Gly Arg Lys Lys Leu Leu Tyr Ile Phe Lys Gln Pro Phe
    130                 135                 140

Met Arg Pro Val Gln Thr Thr Gln Glu Glu Asp Gly Cys Ser Cys Arg
145                 150                 155                 160

Phe Pro Glu Glu Glu Glu Gly Gly Cys Glu Leu Arg Val Lys Phe Ser
                165                 170                 175

Arg Ser Ala Asp Ala Pro Ala Tyr Gln Gln Gly Gln Asn Gln Leu Tyr
            180                 185                 190

Asn Glu Leu Asn Leu Gly Arg Arg Glu Glu Tyr Asp Val Leu Asp Lys
        195                 200                 205

Arg Arg Gly Arg Asp Pro Glu Met Gly Gly Lys Pro Arg Arg Lys Asn
    210                 215                 220

Pro Gln Glu Gly Leu Tyr Asn Glu Leu Gln Lys Asp Lys Met Ala Glu
225                 230                 235                 240

Ala Tyr Ser Glu Ile Gly Met Lys Gly Glu Arg Arg Arg Gly Lys Gly
                245                 250                 255

His Asp Gly Leu Tyr Gln Gly Leu Ser Thr Ala Thr Lys Asp Thr Tyr
            260                 265                 270

Asp Ala Leu His Met Gln Ala Leu Pro Pro Arg
        275                 280

<210> SEQ ID NO 7
<211> LENGTH: 25
<212> TYPE: PRT
<213> ORGANISM: artificial
<220> FEATURE:
<223> OTHER INFORMATION: F2A_aa

<400> SEQUENCE: 7
```

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 8
<211> LENGTH: 19
<212> TYPE: PRT
<213> ORGANISM: artificial
<220> FEATURE:
<223> OTHER INFORMATION: signal peptide_aa

<400> SEQUENCE: 8

Met Asp Trp Thr Trp Arg Ile Leu Phe Leu Val Ala Ala Thr Gly
1               5                   10                  15

Ala His Ser

<210> SEQ ID NO 9
<211> LENGTH: 1665
<212> TYPE: DNA
<213> ORGANISM: artificial
<220> FEATURE:
<223> OTHER INFORMATION: Mouse Il-7-F2A-mouseCCL19-F2A-eGFP

<400> SEQUENCE: 9
atggtccacg tctccttcag atacatcttc ggcatccccc ccctgatcct ggtcctcctg      60
cctgtcacct ccagcgaatg tcatatcaag acaaagagg gcaaggctta tgagagcgtc     120
ctgatgatct ccattgatga gctggataag atgaccggca ccgacagcaa ctgtcccaac     180
aatgagccca acttctttag aaagcacgtg tgtgacgata ccaaggaggc tgccttcctg     240
aacagggccg ccagaaagct gaagcagttc ctgaagatga catttccga ggagttcaac     300 gtgcacctcc tcaccgtgag ccagggcacc cagacactgg tcaattgcac ctccaaggag     360
gagaagaacg tgaaagagca gaaaaagaat gatgcttgtt tcctcaagag ctgctgaggg     420
gagatcaaga cctgttggaa taagatcctg aaaggcagca tcggcagcgg agtcaagcaa     480
accctgaact cgacctgct gaaactggcc ggagatgtgg agagcaatcc cggccctatg     540
gcccccagag tcacccctct gctggccttc agcctgctcg tgctgtggac cttccccgct     600
ccacccctgg gcggcgccaa tgatgctgag gactgttgcc tctccgtgac ccagaggccc     660
atccctggaa acatcgtcaa agccttcagg tacctgctca acgaagacgg atgtagggtg     720
cctgccgtgg tgttcacaac actgagaggc taccagctct gcgcccctcc tgatcagccc     780
tgggtcgaca gaatcatcag aaggctgaag aagtccagcg ccaagaacaa aggcaatagc     840
acaaggagaa gccctgtgag cgaattcgga agcggagtga acagactttt gaattttgac     900
cttctcaagt tggcgggaga cgtggagtcc aaccctggac catgcatggt gagcaagggc     960
gaggagctgt tcaccggggt ggtgcccatc ctggtcgagc tggacggcga cgtaaacgc    1020 cacaagttca gcgtgtccgg cgagggcgag ggcgatgcca cctacggcaa gctgaccctg    1080
aagttcatct gcaccaccgg caagctgccc gtgccctggc ccaccctcgt gaccaccctg    1140
acctacggcg tgcagtgctt cagccgctac cccgaccaca tgaagcagca cgacttcttc    1200
aagtccgcca tgcccgaagg ctacgtccag gagcgcacca tcttcttcaa ggacgacggc    1260
aactacaaga cccgcgccga ggtgaagttc gagggcgaca ccctggtgaa ccgcatcgag    1320
ctgaagggca tcgacttcaa ggaggacggc aacatcctgg ggcacaagct ggagtacaac    1380
tacaacagcc acaacgtcta tatcatggcc gacaagcaga agaacggcat caaggtgaac    1440

```
ttcaagatcc gccacaacat cgaggacggc agcgtgcagc tcgccgacca ctaccagcag    1500 aacacccca tcggcgacgg ccccgtgctg ctgcccgaca accactacct gagcacccag     1560
tccgccctga gcaaagaccc caacgagaag cgcgatcaca tggtcctgct ggagttcgtg    1620
accgccgccg ggatcactct cggcatggac gagctgtaca agtaa                    1665
```

<210> SEQ ID NO 10
<211> LENGTH: 37
<212> TYPE: DNA
<213> ORGANISM: artificial
<220> FEATURE:
<223> OTHER INFORMATION: primer

<400> SEQUENCE: 10

```
atggccggac cggccaccgg tcgccaccat gagcgag                              37
```

<210> SEQ ID NO 11
<211> LENGTH: 41
<212> TYPE: DNA
<213> ORGANISM: artificial
<220> FEATURE:
<223> OTHER INFORMATION: primer

<400> SEQUENCE: 11

```
tcgaattcgc tagcggccgc ttaattaagc ttgtgcccca g                         41
```

<210> SEQ ID NO 12
<211> LENGTH: 33
<212> TYPE: DNA
<213> ORGANISM: artificial
<220> FEATURE:
<223> OTHER INFORMATION: primer

<400> SEQUENCE: 12

```
gctccggacg ccaccatgga agatgccaaa aac                                  33
```

<210> SEQ ID NO 13
<211> LENGTH: 31
<212> TYPE: DNA
<213> ORGANISM: artificial
<220> FEATURE:
<223> OTHER INFORMATION: primer

<400> SEQUENCE: 13

```
gcgaattcca cggcgatctt gccgcccttc t                                    31
```

<210> SEQ ID NO 14
<211> LENGTH: 24
<212> TYPE: DNA
<213> ORGANISM: artificial
<220> FEATURE:
<223> OTHER INFORMATION: primer

```
<400> SEQUENCE: 14
atttctccgt gataggtatc gatg                                    24

<210> SEQ ID NO 15
<211> LENGTH: 22
<212> TYPE: DNA
<213> ORGANISM: artificial
<220> FEATURE:
<223> OTHER INFORMATION: primer

<400> SEQUENCE: 15
aacggtttac gttgaaatgt cc                                      22
```